(12) United States Patent
Kirn

(10) Patent No.: US 9,180,149 B2
(45) Date of Patent: Nov. 10, 2015

(54) SYSTEMIC TREATMENT OF METASTATIC AND/OR SYSTEMICALLY-DISSEMINATED CANCERS USING GM-CSF-EXPRESSING POXVIRUSES

(75) Inventor: David Kirn, Mill Valley, CA (US)

(73) Assignee: SILLAJEN BIOTHERAPEUTICS, INC., San Francisco, CA (US)

( * ) Notice: Subject to any disclaimer, the term of this patent is extended or adjusted under 35 U.S.C. 154(b) by 253 days.

(21) Appl. No.: 11/470,951

(22) Filed: Sep. 7, 2006

(65) Prior Publication Data

US 2007/0065411 A1 Mar. 22, 2007

Related U.S. Application Data

(60) Provisional application No. 60/714,679, filed on Sep. 7, 2005.

(51) Int. Cl.
| | |
|---|---|
| A61K 35/768 | (2015.01) |
| C07K 14/535 | (2006.01) |
| A01K 67/027 | (2006.01) |
| A61K 49/00 | (2006.01) |
| A61K 39/00 | (2006.01) |
| C12N 15/86 | (2006.01) |
| A61K 38/00 | (2006.01) |

(52) U.S. Cl.
CPC ............ *A61K 35/768* (2013.01); *A01K 67/0271* (2013.01); *A61K 49/0008* (2013.01); *C07K 14/535* (2013.01); *A01K 2207/20* (2013.01); *A01K 2227/105* (2013.01); *A01K 2267/0331* (2013.01); *A01K 2267/0393* (2013.01); *A61K 38/00* (2013.01); *A61K 2039/54* (2013.01); *C12N 15/86* (2013.01); *C12N 2710/24111* (2013.01); *C12N 2710/24132* (2013.01); *C12N 2710/24143* (2013.01)

(58) Field of Classification Search
CPC .......... A61K 35/768; A61K 2039/545; C07K 14/535; C12N 15/8636; C12N 2710/24111; C12N 2710/214132; C12N 2710/24143
USPC .............................. 424/93.6; 435/235.1, 320.1
See application file for complete search history.

(56) References Cited

U.S. PATENT DOCUMENTS

| | | | |
|---|---|---|---|
| 4,554,101 A | 11/1985 | Hopp | |
| 4,683,195 A | 7/1987 | Mullis et al. | |
| 4,683,202 A | 7/1987 | Mullis | |
| 4,684,611 A | 8/1987 | Schilperoort et al. | |
| 4,800,159 A | 1/1989 | Mullis et al. | |
| 4,879,236 A | 11/1989 | Smith et al. | |
| 4,883,750 A | 11/1989 | Whiteley et al. | |
| 4,946,773 A | 8/1990 | Maniatis et al. | |
| 4,952,500 A | 8/1990 | Finnerty et al. | |
| 5,073,627 A | 12/1991 | Curtis et al. | |
| 5,151,509 A | 9/1992 | Kotwal et al. ............... | 536/23.2 |
| 5,279,721 A | 1/1994 | Schmid | |
| 5,284,760 A | 2/1994 | Feinstone et al. | |
| 5,302,523 A | 4/1994 | Coffee et al. | |
| 5,322,783 A | 6/1994 | Tomes et al. | |
| 5,354,670 A | 10/1994 | Nickoloff et al. | |
| 5,366,878 A | 11/1994 | Pederson et al. | |
| 5,384,253 A | 1/1995 | Krzyzek et al. | |
| 5,389,514 A | 2/1995 | Taylor | |
| 5,399,363 A | 3/1995 | Liversidge et al. | |
| 5,464,765 A | 11/1995 | Coffee et al. | |
| 5,466,468 A | 11/1995 | Schneider et al. | |
| 5,538,877 A | 7/1996 | Lundquist et al. | |
| 5,538,880 A | 7/1996 | Lundquist et al. | |
| 5,543,158 A | 8/1996 | Gref et al. | |
| 5,550,318 A | 8/1996 | Adams et al. | |
| 5,563,055 A | 10/1996 | Townsend et al. | |
| 5,580,859 A | 12/1996 | Felgner et al. | |
| 5,589,466 A | 12/1996 | Felgner et al. | |
| 5,591,616 A | 1/1997 | Hiei et al. | |
| 5,610,042 A | 3/1997 | Chang et al. | |
| 5,633,016 A | 5/1997 | Johnson | |
| 5,635,377 A | 6/1997 | Pederson et al. | |
| 5,641,515 A | 6/1997 | Ramtoola | |
| 5,656,465 A | 8/1997 | Panicali et al. ............... | 435/456 |
| 5,656,610 A | 8/1997 | Shuler et al. | |
| 5,702,932 A | 12/1997 | Hoy et al. | |
| 5,719,054 A | 2/1998 | Boursnell et al. ............ | 435/456 |
| 5,736,524 A | 4/1998 | Content et al. | |
| 5,739,169 A | 4/1998 | Ocain et al. .................. | 514/658 |
| 5,762,938 A | 6/1998 | Paoletti et al. ............ | 424/199.1 |
| 5,780,448 A | 7/1998 | Davis | |
| 5,789,166 A | 8/1998 | Bauer et al. | |
| 5,789,215 A | 8/1998 | Berns et al. | |

(Continued)

FOREIGN PATENT DOCUMENTS

| | | |
|---|---|---|
| CA | 2105277 | 9/1992 |
| CA | 2305269 | 4/1999 |

(Continued)

OTHER PUBLICATIONS

Broyles et al, J. Virol.78(4):2137-2141, 2004.*
Chen et al, J. Immunol. 24(1):46-57, 2001.*
Kurata et al, J. Allergy Clin. Immunol. 103 (5 Pt. 2):S471-484, 1999.*
Perera et al, PNAS 98(9):5146-5151, 2001.*
Peplinski et al, Surgery 118:185-191, 1995.*
Bartlett et al., "The vaccinia virus N1L protein is an intracellular homodimer that promotes virulence," *J. Gen. Virol.*, 83:1965-1976, 2002.
McIntosh and Smith, "Vaccinia virus glycoprotein A34R is required for infectivity of extracellular enveloped virus," *J. Virol.*, 70:272-281, 1996.
Symons et al., "A study of the vaccinia virus interferon-gamma receptor and its contribution to virus virulence," *J. Gen. Virol.*, 83:1953-1964, 2002.
Wolffe et al., "Deletion of the vaccinia virus B5R gene encoding a 42-kilodalton membrane glycoprotein inhibits extracellular virus envelope formation and dissemination," *J. Virol.*, 67,4732-4741, 1993.
Office Communication, issued in European Application No. 06 814 307.2, dated Mar. 19, 2009.

(Continued)

*Primary Examiner* — Kevin Hill
(74) *Attorney, Agent, or Firm* — Morgan, Lewis & Bockius LLP

(57) ABSTRACT

The present invention concerns methods and compositions for the treatment of cancer and cancer cells using intravascular administration of a vaccinia virus. In some embodiments, methods and compositions involve a replicative vaccinia virus that encodes GM-CSF.

15 Claims, 14 Drawing Sheets

(56) References Cited

U.S. PATENT DOCUMENTS

| | | | |
|---|---|---|---|
| 5,798,208 A | 8/1998 | Crea | |
| 5,798,339 A | 8/1998 | Brandes | |
| 5,801,005 A | 9/1998 | Cheever et al. | 435/7.24 |
| 5,824,311 A | 10/1998 | Greene et al. | 424/138.1 |
| 5,824,348 A | 10/1998 | Fujiu et al. | |
| 5,830,650 A | 11/1998 | Crea | |
| 5,830,880 A | 11/1998 | Sedlacek et al. | 514/44 |
| 5,840,873 A | 11/1998 | Nelson et al. | |
| 5,843,640 A | 12/1998 | Patterson et al. | |
| 5,843,650 A | 12/1998 | Segev | |
| 5,843,651 A | 12/1998 | Stimpson et al. | |
| 5,843,663 A | 12/1998 | Stanley et al. | |
| 5,846,225 A | 12/1998 | Rosengart et al. | |
| 5,846,233 A | 12/1998 | Lilley et al. | |
| 5,846,708 A | 12/1998 | Hollis et al. | |
| 5,846,709 A | 12/1998 | Segev | |
| 5,846,717 A | 12/1998 | Brow et al. | |
| 5,846,726 A | 12/1998 | Nadeau et al. | |
| 5,846,729 A | 12/1998 | Wu et al. | |
| 5,846,783 A | 12/1998 | Wu et al. | |
| 5,846,945 A | 12/1998 | McCormick | 514/44 |
| 5,849,481 A | 12/1998 | Urdea et al. | |
| 5,849,483 A | 12/1998 | Shuber | |
| 5,849,486 A | 12/1998 | Heller et al. | |
| 5,849,487 A | 12/1998 | Hase et al. | |
| 5,849,497 A | 12/1998 | Steinman | |
| 5,849,546 A | 12/1998 | Sousa et al. | |
| 5,849,547 A | 12/1998 | Cleuziat et al. | |
| 5,851,770 A | 12/1998 | Babon et al. | |
| 5,851,772 A | 12/1998 | Mirzabekov et al. | |
| 5,853,990 A | 12/1998 | Winger et al. | |
| 5,853,992 A | 12/1998 | Glazer et al. | |
| 5,853,993 A | 12/1998 | Dellinger et al. | |
| 5,856,092 A | 1/1999 | Dale et al. | |
| 5,858,652 A | 1/1999 | Laffler et al. | |
| 5,861,244 A | 1/1999 | Wang et al. | |
| 5,863,732 A | 1/1999 | Richards | |
| 5,863,753 A | 1/1999 | Haugland et al. | |
| 5,866,331 A | 2/1999 | Singer et al. | |
| 5,866,337 A | 2/1999 | Schon | |
| 5,866,366 A | 2/1999 | Kallender | |
| 5,871,740 A | 2/1999 | Smith | 424/186.1 |
| 5,871,986 A | 2/1999 | Boyce | |
| 5,882,864 A | 3/1999 | An et al. | |
| 5,900,481 A | 5/1999 | Lough et al. | |
| 5,905,024 A | 5/1999 | Mirzabekov et al. | |
| 5,910,407 A | 6/1999 | Vogelstein et al. | |
| 5,912,124 A | 6/1999 | Kumar | |
| 5,912,145 A | 6/1999 | Stanley | |
| 5,912,148 A | 6/1999 | Eggerding | |
| 5,916,776 A | 6/1999 | Kumar | |
| 5,916,779 A | 6/1999 | Pearson et al. | |
| 5,919,626 A | 7/1999 | Shi et al. | |
| 5,919,630 A | 7/1999 | Nadeau et al. | |
| 5,922,574 A | 7/1999 | Minter | |
| 5,925,517 A | 7/1999 | Tyagi et al. | |
| 5,928,870 A | 7/1999 | Lapidus et al. | |
| 5,935,819 A | 8/1999 | Eichner et al. | |
| 5,935,825 A | 8/1999 | Nishimura et al. | |
| 5,939,291 A | 8/1999 | Loewy et al. | |
| 5,942,391 A | 8/1999 | Zhang et al. | |
| 5,945,100 A | 8/1999 | Fick | |
| 5,969,094 A | 10/1999 | Compans et al. | |
| 5,981,274 A | 11/1999 | Tyrrell et al. | |
| 5,994,624 A | 11/1999 | Trolinder et al. | |
| 6,093,700 A | 7/2000 | Mastrangelo et al. | 514/44 |
| 6,177,076 B1 | 1/2001 | Lattime et al. | 424/93.6 |
| 6,265,189 B1 | 7/2001 | Paoletti et al. | 435/70.1 |
| 6,355,252 B1 | 3/2002 | Smith et al. | 424/232.1 |
| 6,475,999 B1 | 11/2002 | Mastrangelo et al. | 514/44 |
| 6,521,449 B1 | 2/2003 | Polack et al. | 435/320.1 |
| 7,208,313 B2 | 4/2007 | McCart et al. | 435/320.1 |
| 7,326,529 B2 | 2/2008 | Ali et al. | |
| 7,588,767 B2 | 9/2009 | Szalay et al. | |
| 7,588,771 B2 | 9/2009 | Szalay et al. | |
| 8,105,578 B2 | 1/2012 | Roberts et al. | |
| 2002/0086022 A1 | 7/2002 | Davis | |
| 2002/0146702 A1 | 10/2002 | Vielkind | |
| 2003/0025141 A1 | 2/2003 | Grimm | 257/301 |
| 2003/0086906 A1 | 5/2003 | Mastrangelo et al. | 424/93.2 |
| 2003/0206886 A1* | 11/2003 | Lattime et al. | 424/93.2 |
| 2004/0091995 A1 | 5/2004 | Schlom et al. | 435/235.1 |
| 2005/0031617 A1 | 2/2005 | Ma et al. | |
| 2005/0031643 A1 | 2/2005 | Szalay et al. | 424/199.1 |
| 2005/0207974 A1 | 9/2005 | Deng et al. | |
| 2006/0051370 A1 | 3/2006 | Szalay et al. | 424/199.1 |
| 2007/0025981 A1 | 2/2007 | Szalay et al. | 424/130.1 |
| 2007/0065411 A1 | 3/2007 | Kirn | |
| 2008/0286237 A1 | 11/2008 | Kirn | 435/6 |
| 2009/0004723 A1 | 1/2009 | Kirn | 435/236 |
| 2009/0047307 A1 | 2/2009 | Harrop et al. | |
| 2009/0053244 A1 | 2/2009 | Chen et al. | |
| 2010/0303714 A1 | 12/2010 | Kirn | |

FOREIGN PATENT DOCUMENTS

| | | | | |
|---|---|---|---|---|
| CA | 2370187 | 10/2000 | | |
| CA | 2388807 | 5/2001 | | |
| CA | 2375189 | 2/2010 | | |
| WO | WO 87-06270 | 10/1987 | | |
| WO | WO 89-09284 | 10/1989 | | |
| WO | WO 94-09699 | 5/1994 | | |
| WO | WO 95-06128 | 3/1995 | | |
| WO | WO 99/29343 | 6/1999 | | |
| WO | WO 00/62735 | 10/2000 | | |
| WO | WO 00/73479 | * 12/2000 | | C12N 15/863 |
| WO | WO 2004/014314 | 2/2004 | | |
| WO | WO 2008/043576 | 4/2008 | | |
| WO | WO 2008/047242 | 4/2008 | | |
| WO | WO 2008/113078 | 9/2008 | | |

OTHER PUBLICATIONS

Thorne et al., "Rational strain selection and engineering creates a broad spectrum, systemically effective oncolytic poxvirus, JX-963," *The Journal of Clinical Investigation*, 117(11):3350-3358, 2007.

Adams et al., "Clinical studies of human papilloma vaccines in pre-invasive and invasive cancer," *Vaccine*, 19(17-19):2549-56, 2001.

Alcami and Smith, "A soluble Receptor for Interleukin-1beta encoded by Vaccinia Virus: A Novel Mechanism of Virus Modulation of the Host Response to Infection," *Cell*, 71(1):153-67, 1992.

Alcami and Smith., "The vaccinia virus soluble interferon-gamma receptor is a homodimer,"*J Gen Virol.*, 83(Pt 3):545-9, 2002.

Alcami et al., "Poxviruses: Capturing Cytokines and Chemokines," *Sem Virol*, 5:419-427, 1998.

Alcami et al., "The vaccinia virus soluble alpha/beta interferon (IFN) receptor bnds to the cell surface and protects cells from the anivral effect of IFN," *J Virology*, 74(23):11230-11239, 2000.

Alcami et al., "Vaccinia virus strains Lister, USSR and Evans express soluble and cell-surface tumour necrosis factor receptors," *J Gen Virol*, 80(Pt 4):949-59, 1999.

Alimonti et al., "TAP expression provides a general method for improving the recognition of malignant cells in vivo," *Nature Biotech*, 18(5):515-520, 2000.

Andoh et al., "Sodium butyrate enhances complement-mediated cell injury via down-regulation of decay-accelerating factor expression in colonic cancer cells," *Cancer Immunol Immunother*, 50(12):663-672, 2002.

Arakawa et al., "Clinical trial of attenuated vaccinia virus AS strain in the treatment of advanced adenocarcinoma," *J Cancer Res Clin Oncol*, 113:95-98, 1987.

Austin-Ward and Villaseca, "Gene therapy and its applications," *Rev Med Chil*, 126(7):838-845, 1998.

Berwin et al., "Virally induced lytic cell death elicits the release of immunogenic GRP94/gp96,"*J Biol Chem*, 276(24):21083-8, 2001.

Blanchard et al., "Modified vaccinia virus Ankara undergoes limited replication in human cell and lacks several immunomodulatory proteins: implications for use as a human vaccine," *J Gen Virol.*, 79(Pt 5):1159-67, 1998.

Blanchard et al., "Vaccinia virus strain modified virus ankara: characterization of cytokine receptor profile, virological features, and use

(56) References Cited

OTHER PUBLICATIONS as an immunological reagent," *Conf Adv AIDS Vaccine Dev*, 108 (Poster 3): May 4-7, 1997. (Abstract).
Blasco and Moss, "Role of cell-associated enveloped vaccinia virus in cell-to-cell spread," *J Virology*, 66(7):4170-4179, 1992.
Blasco et al., "Dissociation of progeny vaccinia virus from the cell membrane is regulated by a viral envelope glycoprotein: effect of a point mutation in the lectin homology domain of the A34R gene," *J Virology*, 67(6):3319-3325, 1993.
Bowie et al., "A46R and A52R from vaccinia virus are antagonist of host IL-1 and toll-like receptor signaling," *Proc Natl Acad Sci USA*, 97(18):10162-10167, 2000.
Boyd et al., "Adenovirus E1B 19 kDa and Bcl-2 proteins interact with a common set of cellular proteins," *Cell*, 79:341-351, 1994.
Bukowski et al., "Signal transduction abnormalities in T lymphocytes from patients with advanced renal carcinoma: clinical relevance and effects of cytokine therapy," *Clin Cancer Res*, 4(10):2337-2347, 1998.
Buller and Palumbo, "Poxvirus Pathogenesis," *Microbiol Rev*, 55:80-122, 1991.
Burke, "Cytokines (IFNs, TNF-alpha, IL-2 and IL-12) and animal models of cancer," *Cytokines Cell Mol Ther*, 5(1):51-61, 1999.
Cantrell et al., "Cloning, sequence, and expression of a human granulocyte/macrophage colony-stimulating factor," *Proc. Natl Acad. Sci. USA*, 82:6250-6254, 1985.
Caragine et al., "A tumor-expressed inhibitor of the early but not late complement lytic pathway enhances tumor growth in a rat model of human breast cancer," *Cancer Res*, 62(4):1110-1115, 2002.
Chen et al., "Low-dose vaccinia virus-mediated cytokine gene therapy of glioma," *J Immunother*, 24:46-57, 2001.
Christodoulides et al., "Immunization with recombinant class 1 outer-membrane protein from *Neisseria meningitidis*: influence of liposomes and adjuvants on antibody avidity, recognition of native protein and the induction of a bactericidal immune response against meningococci," *Microbiology*, 144(Pt 11):3027-3037, 1998.
Colamonici et al., "Vaccinia virus B18R gene encodes a type I interferon-binding protein that blocks interferon alpha transmembrane signaling," *J Biol Chem*, 270:15974-15978, 1995.
Cunnion, "Tumor necrosis factor receptors encoded by poxviruses," *Mol Genet Metab*, 67(4):278-82, 1999.
Davidson et al., "Intralesional cytokine therapy in cancer: a pilot study of GM-CSF infusion in mesothelioma," *J Immunother*, 21(5):389-398, 1998.
Dobbelstein and Shenk, "Protection against apoptosis by the vaccinia virus SPI-2 (B13R) gene product," *J Virology*, 70:6479-6485, 1996.
Doehn amd Jocham, "Technology evaluation: TG-1031, Transgene SA," *Curr Opin Mol Ther*, 106-11,2000.
Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci. USA*, 90:3539-3543, 1993.
Durrant and Spendlove, "Immunization against tumor cell surface complement-regulatory proteins," *Curr Opin Investig Drugs*, 2(7):959-966, 2001.
Eliopoulos et al., "The control of apoptosis and drug resistance in ovarian cancer: influence of p53 and Bcl-2," *Oncogene*, 11(7):1217-1228, 1995.
Feng et al., "Induction of CD8+ T-lymphocyte responses to a secreted antigen of *Mycobacterium tuberculosis* by an attenuated vaccinia virus," *Immunol Cell Biol.*, 79(6):569-75, 2001.
Gardner et al., "Vaccinia virus semaphorin A39R is a 50-55 kDa secreted glycoprotein that affects the outcome of infection in a murine intradermal model," *J Gen Virol*, 82(Pt 9):2083-93, 2001.
Gnant et al., "Systemic administration of a recombinant vaccinia virus expressing the cytosine deaminase gene and subsequent treatment with 5-fluorocytosine leads to tumor-specific gene expression and prolongation of survival in mice," *Cancer Res*, 59(14):3396-3403, 1999.
Goebel et al., "The complete DNA sequence of vaccinia virus," *Virology*, 179(1):247-266 and 517-563, 1990.

Gomella et al., "Phase i study of intravesical vaccinia virus as a vector for gene therapy of bladder cancer," *J Urol*, 166:1291-5, 2001.
Graham et al., "The T1/35kDa Family of Poxvirus-Secreted Proteins Bind Chemokines and Modulate Leukocyte Influx to Virus-Infected Tissues," *Virology*, 229(1):12-24, 1997.
Gross et al., "BCL-2 family members and the mitochondria in apoptosis," *Genes Dev*, 13(15):1899-1911, 1999.
Hanibuchi et al., "Therapeutic efficacy of mouse-human chimeric anti-ganglioside GM2 monoclonal antibody against multiple organ micrometastases of human lung cancer in NK cell-depleted SCID mice," *Int J Cancer*, 78(4):480-485, 1998.
Hawkins et al., "Oncolytic biotherapy: a novel therapeutic plafform," *Lancet Oncol*, 3(1):17-26, 2002.
He et al., "Viral recombinant vaccines to the E6 and E7 antigens of HPV-16," *Virology*, 270(1):146-161, 2000.
Heise et al., "Efficacy of a replication-competent adenovirus (ONYX-015) following intratumoral injection: intratumoral spread and distribution effects," *Cancer Gene Ther*, 6(6):499-504, 1999.
Heise et al., "ONYX-015, an E1B gene-attenuated adenovirus, causes tumor-specific cytolysis and antitumoral efficacy that can be augmented by standard chemotherapeutic agents," *Nat Med*, 3:639-45, 1997.
Hellstrand et al., "Histamine and cytokine therapy," *Acta Oncol*, 37(4):347-353, 1998.
Hermiston, "Gene delivery from replication-selective viruses: arming guided missiles in the war against cancer," *J Clin Invest*, 105:1169-1172, 2000.
Holzer et al., "Highly efficient induction of protective immunity by a vaccinia virus vector defective in late gene expression," *Journal of Virology*, 73(6):4536-4542, 1999.
Homey et al., "Chemokines: Agents for the Immunotherapy of Cancer?," *Nature Rev Immunol*, 2:175-184, 2002.
Hui and Hashimoto, "Pathways for potentiation of immunogenicity during adjuvant-assisted immunizations with *Plasmodium falciparum* major merozoite surface protein 1," *Infect Immun*, 66(11):5329-5336, 1998.
Ikeda et al., "Oncolytic virus therapy of multiple tumors in the brain requires suppression of innate and elicited antiviral responses," *Nat Med*, 5(8):881-887, 1999.
Isaacs et al., "Vaccinia virus complement-control protein prevents antibody-dependent complement-enhanced neutralization of infectivity and contributes to virulence," *Proc. Natl. Acad Sci. USA*, 89(2):628-32, 1992.
Kantor et al., "Antitumor activity and immune responses induced by a recombinant carcinoembryonic antigen-vaccinia virus vaccine," *J Natl Cancer Inst*, 84(14):1084-1091, 1992.
Kawakita et al., "Poxvirus vectors for gene transfer," *Acta Urologica Japonica*, 43(11):835-838, 1997.
Kay et al., "Transient immunomodulation with anti-CD40 ligand antibody and CTLA41g enhances persistence and secondary adenovirus-mediated gene transfer into mouse liver," *Proc Natl Acad Sci USA*, 97(9):4686-4691, 1997.
Kettle, "Vaccinia virus serpin B12R (SPI-2) inhibits interleukin 1-beta converting enzyme and protects virus-infected cells from TNF- and Fas-mediated apoptosis, but does not prevent IL-1-beta induced fever," *J. Gen. Vir.*, 78:677-685, 1997.
Kim et al.,"167 . Both Oncolysis and Tumor Immunity Are Involved in an Antitumoral Efficacy by Intratumoral Injection of Recombinant Vaccinia Virus (TK Deleted, hGM-CSF Inserted Wyeth Strain) in a VX2 Rabbit Model," *Mol. Therapy*, 11:67, 2005.
Kim et al., "Systemic Armed Oncolytic and Immunologic Therapy for Cancer with JX-594, a Targeted Poxvirus Expressing GM-CSF," *Mol Ther*, 14:361-70, 2006.
Kirn et al., "Replication-selective virotherapy for cancer: biological principles, risk management and future direction," *Nat Med*, 7(7):781-787, 2001.
Kirn et al., "Systemic Oncolytic and Immunologic Therapy for Cancer with JX-594, a Targeted Poxvirus Expressing GM-CSF," *Mol. Ther.*, 13:S244-S245, 2006.
Kirn et al., "The emerging fields of suicide gene therapy and virotherapy," *Trends Mol Med*, 8(4):S68-S73, 2002.

(56) References Cited

OTHER PUBLICATIONS

Law et al., "Antibody-sensitive and antibody-resistant cell-to-cell spread by vaccinia virus: role of the A33R protein in antibody-resistant spread," *J Gen Virol.*, 83(Pt 1):209-22, 2002.
Lee et al., "406. Enhancedc Vaccinia-meditated Antitumor Response after Specific Inhibiton of the Cellular Immune Response," *Mol. Ther.*, 1:S156-S157, 2000.
Loparev et al., "A third distinct tumor necrosis factor receptor of orthopoxviruses," *Proc Natl Acad Sci USA*, 95:3789-3791, 1998.
Marshall et al., "Phase I study in advanced cancer patients of a diversified prime-and-boost vaccination protocol using recombinant vaccinia virus and recombinant nonreplicating avipox virus to elicit anti-carcinoembryonic antigen immune responses," *J Clin Oncol*, 18(23):3964-73, 2000.
Mastrangelo and Lattime, "Virotherapy clinical trials for regional disease: in situ immune modulation using recombinant poxvirus vectors," *Cancer Gene Ther.*, 9:1013-1021, 2002.
Mastrangelo et al., "Intralesional Vaccinia/GM-CSF Recombinant Virus in the Treatment of Metastatic Melanoma," *Adv. Exp. Med Biol.*, 465:391-400, 2000.
Mastrangelo et al., "Intratumoral recombinant GM-CSF-encoding virus as gene therapy in patients with cutaneous melanoma," *Cancer Gene Ther.*, 6:409-422, 1998.
Mathew et al., "A mutational analysis of the vaccinia virus B5R protein," *J Gen Virol.*, 82(Pt 5):1199-213, 2001.
McCart et al., "Complex interactions between the replicating oncolytic effect and the enzyme/prodrug effect of vaccinia-mediated tumor regression," *Gene Ther*, 7(14):1217-1223, 2000.
McCart et al., "Systemic cancer therapy with a tumor-selective vaccinia virus mutant lacking thymidine kinase and vaccinia growth factor genes," *Cancer Res.*, 61:8751-8757, 2001.
McFadden and Murphy, "Host-related immunomodulators encoded by poxviruses and herpesviruses," *Curr Opin Microbiol*, 3(4):371-8, 2000.
Moss, "Poxviridae and Their Replication," In: *Fields Virology*, Fields et al. (ed.), Raven Publ, New York, pp. 953-985, 1996.
Mossman et al., "Myxoma virus M-T7, a secreted homolog of the interferon-gamma receptor, is a critical virulence factor for the development of myxomatosis in European rabbits," *Virology*, 215(1):17-30, 1996.
Mukherjee et al., "Replication-restricted vaccinia as a cytokine gene therapy vector in cancer: persistent transgene expression despite antibody generation," *Cancer Gene Ther*, 7(5):663-670, 2000.
Mullen and Tanabe, "Viral Oncolysis 2002," *The Oncologist*, 7:106-119, 2002.
Ng et al., "The vaccinia virus A41L protein is a soluble 30 kDa glycoprotein that affects virus virulence," *J Gen Virol.*, 82(Pt 9):2095-105, 2001.
Nielsen et al., "Adenovirus-mediated p53 gene therapy and paclitaxel have synergistic efficacy in models of human head and neck, ovarian, prostate, and breast cancer," *Clin Cancer Res*, 4(4):835-846, 1998.
Nielsen et al., "Adenovirus-mediated p53 therapy synergizes with paclitaxel against human ovarian, mammary, prostate, head and neck, and liver cancer," *Cancer Gene Therapy*, 4(6):S12, 1997.
Parato et al., "Recent Progress in the Battle between Oncolytic Viruses and Tumours," *Nat Rev Cancer*, 5, 965-76, 2005.
Pietras et al., "Remission of human breast cancer xenografts on therapy with humanized monoclonal antibody to HER-2 receptor and DNA-reactive drugs," *Oncogene*, 17(17):2235-2249, 1998.
Price et al. "The vaccinia virus B9R protein is a 6 kDa intracellular protein that is non-essential for virus replication and virulence," *J Gen Virol.*, 83(Pt 4):873-8, 2002.
Price et al., "Vaccinia virus gene B7R encodes an 18-kDa protein that is resident in the endoplasmic reticulum and affects virus virulence," *Virology*, 1;267(1):65-79, 2000.
Puhlmann et al., "Thymidine Kinase-Deleted Vaccinia Virus Expressing Purine Nucleoside Phosphorylase as a Vector for Tumor-Directed Gene Therapy," *Hum Gene Ther.*, 10: 649-57, 1999.
Puhlmann et al., "Vaccinia as a vector for tumor-directed gene therapy: biodistribution of a thymidine kinase-deleted mutant," *Cancer Gene Ther*, 7(1):66-73, 2000.
Qin et al., "Interferon-beta gene therapy inhibits tumor formation and causes regression of established tumors in immune-deficient mice," *Proc Natl Acad Sci USA*, 95(24):14411-14416, 1998.
Reading et al., "Vaccinia virus CrmE encodes a soluble and cell surface tumor necrosis factor receptor that contributes to virus virulence," *Virology*, 292(2):285-98, 2002.
Rosel et al., "Conserved TAAATG sequence a the transcriptional and translational initiation sites of vaccinia virus late genes deduced by structural and functional analysis of the HindIII H genome fragment," *J Virology*, 60(2):436-449, 1986.
Saraiva and Alcami, "CrmE, a novel soluble tumor necrosis factor receptor encoded by poxviruses," *J Virol*, 75(1):226-233, 2001.
Scholl et al., "Recombinant vaccinia virus encoding human MUC1 and IL2 as immunotherapy in patients with breast cancer," *J Immunother*, 23:570-80, 2000.
Seet et al., "Molecular determinants for CC-chemokine recognition by a poxvirus CC-chemokine inhibitor," *Proc Natl Acad Sci USA*, 98(16):9008-9013, 2001.
Siemens et al., "Comparison of gene transfer and expression of viral vectors in an orthotopic murine bladder cancer model," *Journal of Urology*, 170(3):979-84, 2003.
Sinkovics and Horvath, "Newcastle disease virus (NDV): brief history of its oncolytic strains," *J Clin Viro*, 16:1-15, 2000.
Smith and Vanderplasschen, "Extracellular enveloped vaccinia virus," *Adv Exp Med Biol*, 440:395-414, 1998.
Smith et at, "Ectromelia, vaccinia and cowpox viruses encode secreted interleukin-18-binding proteins," *J. Gen. Virol.*, 81:1223-1230, 2000.
Smith et al., "Lethality-based selection of recombinant genes in mammalian cells: application to identifying tumor antigens," *Nat Med*, 967-72, 2001.
Smith et al., "Vaccinia virus immune evasion," *Immunol Rev*, 159:137-154, 1997.
Smith, "Vaccinia virus immune evasion," *Immunol Lett.*, 65(1-2):55-62, 1999.
Spehner et al. "Enveloped virus is the major virus form produced during productive infection with the modified vaccinia virus Ankara strain," *Virology*, 273(1):9-15, 2000.
Spriggs et al., "Vaccinia and Cowpox Viruses Encode a Novel Secreted Interleukin-l-Binding Protein," *Cell*, 71(1):145-152, 1992.
Sroller, "Effect of IFN-gamma receptor gene deletion on vaccinia virus virulence," *Arch. Virol.*, 146:239-249, 2001.
Symons et al., "The vaccinia virus Cl2L protein inhibits mouse IL-18 and promotes virus virulence in the murine intranasal model," *J. Gen. Virol.*, 83:2833-2844, 2002.
Symons et al., "Vaccinia virus encodes a soluble type I interferon receptor of novel structure and broad species specificity," *Cell*, 81:551-560, 1995.
Thorne and Kim, "Future directions of the field oncolytic virotherapy: a perspective on the use of vaccinia virus," *Expert Opinion Biol. Ther.*, 4:1307-1321, 2004.
Thorne et al.,"169. The Creation of Novel Oncolytic Vaccinia Virus Vectors for Efficient Systemic Delivery of Transgenes to Tumors," *Mol. Ther.*, 11:67, 2005.
Thorne et al., "Rational Strain Selection and Engineering Creates a Broad Spectrum Systemically Effective Oncolytic Poxvirus JX-963," *Article in Press*, 2007.
Thorne et al., "The Use pf Oncolytic Vaccinia Viruses in the Treatment of Cancer: A New Role for an Old Ally?," *Current Gene Therapy*, 5:429-443, 2005.
Timiryasova et al., "Antitumor effect of vaccinia virus in glioma model," *Oncol Res*, 11:133-144, 1999.
Todo et al., "In situ expression of soluble B7-1 in the context of oncolytic herpes simplex virus induces potent antitumor immunity," *Cancer Res*, 61:153-161, 2001.
Trevor et al., "Transduction of human dendritic cells with a recombinant modified vaccinia Ankara virus encoding MUC1 and IL-2," *Cancer Immunology Immunotherapy*, 50(8):397-407, 2001.

(56) References Cited

OTHER PUBLICATIONS

Tscharke et al., "Dermal infection with vaccinia virus reveals roles for virus proteins not seen using other inoculation routes," *J. Gen. Virol.*, 83:1977-1986, 2002.
Upton et al., "Encoding of a Homolog of the IFN-γ Receptor by Myxoma Virus," *Science*, 258:1369-1372, 1992.
Upton et al., "Myxoma Virus Expresses a Secreted Protein with Homology to the Tumor Necrosis Factor Receptor Gene Family That Contributes to Viral Virulence," *Virology*, 184(1):370-382, 1991.
Vanderplasschen et al., "Extracellular enveloped vaccinia virus is resistant to complement because of incorporation of host complement control proteins into its envelope," *Proc Natl Acad Sci USA*, 95(13):7544-7549, 1998.
Verardi et al., "Vaccinia virus vectors with a inactivated gamma interferon receptor homolog gen (B8R) are attenuated in vivo without a concomitant reduction in immunogenicity," *J Virol*, 75(1):11-18, 2001.
Vicari and Caux, "Chemokines in cancer," *Cytokine Growth Factor Rev*, 13:143-154, 2002.
Weijer et al., "Histopathology of tumor regression after intralesional injection of *Mycobacterium bovis*., 2. Comparative effects of vaccinia virus, oxazolone, and turpentine," *J Natl Cancer Inst*, 48:1697-707, 1972.
Wold et al., "Adenovirus proteins that subvert host defenses," *Trends Microbiol*, 2:437-443, 1994.
Xiang et al., "Blockade of interferon induction and action by the E3L double-stranded RNA binding proteins of vaccinia virus," *J Virol*, 76(10):5251-9, 2002.
Xu et al., "Myxoma virus expresses a TNF receptor homolog with two distinct functions," *Virus Genes*, 21(1-2):97-109, 2000.
Extended European Search Report issued in European Application No. 08167984.7, dated Mar. 6, 2009.
Legrand et al., "Vaccinia viruses with a serpin gene deletion and expressing IFN-γ, induce potent immune responses without detectable replication in vivo," PNAS, 102(8):2940-2945, 2005.
Noguiez-Hellin et al., "Plasmoviruses: Nonviral/viral vectors for gene therapy," *Proc. Natl. Acad. Sci. USA*, 93:4175-4180, 1996.
Office Action issued in Canadian Patent Application No. 2,494,844 mailed Jul. 22, 2010.
Office Action issued in European Application No. 08 167 984.7, mailed Sep. 10, 2009.
Office Action issued in Japanese Application No. 2004-528045, dated Jul. 6, 2009.
Office Action issued in U.S. Appl. No. 10/524,932, mailed Apr. 15, 2008.
Office Action issued in U.S. Appl. No. 10/524,932, mailed Jan. 3, 2008.
Office Action issued in U.S. Appl. No. 10/524,932, mailed Oct. 24, 2008.
Office Action issued in U.S. Appl. No. 11/838,757, mailed Apr. 29, 2009.
Office Action issued in U.S. Appl. No. 11/838,757, mailed Dec. 29, 2009.
Office Action issued in U.S. Appl. No. 11/838,757, mailed Sep. 1, 2009.
Office Action issued in U.S. Appl. No. 11/838,774, mailed Jul. 6, 2010.
Office Action issued in U.S. Appl. No. 11/838,774, mailed May 19, 2009.
Office Action issued in U.S. Appl. No. 11/838,774, mailed Nov. 19, 2009.
Sinkovics, "New Developments in the Virus Therapy of Cancer: A Historical Review," Intervirology, 36:193-214, 1993.
Office Communication, issued in European Patent Application No. 06 814 307.2, dated Mar. 8, 2011.
Office Communication, issued in Australian Patent Application No. 2006287441, dated May 6, 2011.
Office Communication, issued in Chinese Patent Application No. 201010158338.1, dated May 3, 2011. (English translation).
Office Communication, issued in Chinese Patent Application No. 200680041389.8, dated Jun. 10, 2011. (English translation).
Abou-Alfa GK, et al., "Phase II Study of Sorafenib in Patients with Advanced Hepatocellular Carcinoma," J. Clin. Oncol., vol. 24, No. 26, pp. 4293-4300 (2006).
Aigner F., et al., "Anal HPV infections," Wien Klin Wochenschr., vol. 230, No. 19-20, pp. 631-641 (2008) (Abstract).
Amato, R., et al., "Vaccination of Prostate Cancer Patients With Modified Vaccinia Ankara Delivering the Tumor Antigen 5T4 (TroVax): A Phase 2 Trial," Journal Immunother., vol. 31, No. 6, pp. 577-585 (Jul.-Aug. 2008).
Baranyi, L., et al., "Membrane-Bound Complement Regulatory Activity is Decreased on Vaccinia Virus-Infected Cells," Clin Exp Immunol., vol. 98, No. 1, pp. 134-139 (Oct. 1994).
Bell, J., et al., "Getting Oncolytic Virus Therapies Off the Ground," Cancer Cell, vol. 4, No. 1, pp. 7-11 (Jul. 2003).
Bischoff, J., et al., "An Adenovirus Mutant that Replicates Selectively in p53-deficient Human Tumor Cells," Science, vol. 274, pp. 373-376 (Oct. 18, 1996).
Bretibach, C. J., et al., "Targeted Inflammation During Oncolytic Virus Therapy Severely Compromises Tumor Blood Flow," Mol. Ther., vol. 15, No. 9, pp. 1686-1693 (2007).
Cheng, A. L., Efficacy and Safety of Sorafenib in Patients in the Asia-Pacific Region with Advanced Hepatocellular Carcinoma: A Phase III Randomised, Double-Blind, Placebo-Controlled Trial., vol. 10, No. 1, pp. 25-34 (2009).
Choi, H., et al., "CT Evaluation of the Response of Gastrointestinal Stromal Tumors after Imatinib Mesylate Treatment: A Quantitative Analysis Correlated with FDG PET Findings," American Journal of Roentgenology, vol. 183, pp. 1619-1628 (2004).
Coffey,M., et al., "Reovirus Therapy of Tumors With Activated Ras Pathway," Science, vol. 282, pp. 1332-1334 (1998).
Coiffier, B., et al., "Safety and Efficacy of Ofatumumab, A Fully Human Monoclonal Anti-CD20 Antibody, in Patients With Relapsed or Refractory B-cell Chronic Lymphocytic Leukemia: A Phase 1-2 Study," Blood, vol. 111, No. 3, pp. 1094-1100, (Feb. 2008).
Dechant, M., et al., "Complement-Dependent Tumor Cell Lysis Triggered by Combinations of Epidermal Growth Factor Receptor Antibodies," Cancer Res., vol. .8, No. 13, pp. 4998-5003 (Jul. 1, 2008).
Demetri, G., et al., "Efficacy and Safety of Sunitinib in Patients with Advanced astrointestinal Stromal Tumour After Failure of Imatinib: A Randomised Controlled Trial," The Lancet, vol. 368, pp. 1329-1338 (Oct. 14, 2006).
Di Gaetano, N., et al., "Complement Activation Determines the Therapeutic Activity of Rituximab In Vivo," J Immunol., vol. 171, No. 3, pp. 1581-1587 (Aug. 1, 2003).
Escudier, B., et al., "Sorafenib in Advanced Clear-Cell Renal-Cell Carcinoma," N. Engl. J. Med., vol. 356, No. 2, pp. 125-134 (Jan. 11, 2007).
Extended European Search Report issued in European Patent Application No. 10181820.1, dated Dec. 7, 2010.
Extended European Search Report issued in European Patent Application No. 10181845.8, dated Dec. 3, 2010.
Extended European Search Report issued in European Patent Application No. 10816293.4 dated Mar. 4, 2014.
Frohman, "PCR Protocols: A Guide to Methods and Applications," Academic Press, pp. 28-38 and pp. 228-236 (1990).
Golay, J., et al., "The Role of Complement in the Therapeutic Activity of Rituximab in a Murine B Lymphoma Model Homing in Lymph Nodes," Haematologica, vol. 91, No. 2, pp. 176-183 (Feb. 2006).
Guo, Z.S., et al., "The Enhanced Tumor Selectivity of an Oncolytic Vaccinia Lacking the Host Range and Antiapoptosis Genes SPI-1 and SPI-2," Cancer Res., vol. 65, No. 21, pp. 9991-9998, (Nov. 1, 2005).
Gulley, J., et al., "Pilot Study of Vaccination with Recombinant CEA-MUC-1-TRICOM Poxviral-Based Vaccines in Patients with Metastatic Carcinoma," Clin Cancer Res., vol. 14, No. 10, pp. 3060-3069 (May 2008).
Harjunpaa, A., et al., . Rituximab (anti-CD20) therapy of B-cell lymphomas: direct complement killing is superior to cellular effect or mechanisms. Scand J Immunol. Jun. 2000;51(6):634-41.
Heise, C., et al., "An Adenovirus E1A Mutant That Demonstrates Potent and Selective Antitumoral Efficacy," Nature Medicine, vol. 6, No. 10., pp. 1134-1139 (2000).

(56) References Cited

OTHER PUBLICATIONS

Hengstschlager, M., et al., Different Regulation of Thymidine Kinase During the Cell Cycle of Normal Versus DNA Tumor Virus-Transformed Cells., J. Biol. Chem., vol. 269, pp. 13836-13842 (1994).
Heo, J., et al., "Randomized Dose-Finding Clinical Trial of Oncolytic Immunotherapeutic Vaccina JX-594 in Liver Cancer," Nature Medicine, vol. 19, No. 3, pp. 329-336 (Mar. 2013 ).
Heo, J., et al., "Evaluating Antivascular Effects and Antitumoral Activity in Patients with Hepatocellular Carcinoma Treated with JX-594, a Targeted Multimechanistic Oncolytic Poxvirus, Prior to Sorafenib Therapy, ASCO Meeting Abstracts," Journal of Clinical Oncology, vol. 28, No. 15 Sup., p. e14564 (May 1, 2010).
Higano, C., et al., "Integrated data from 2 randomized, double-blind, placebo-controlled, phase 3 trials of active cellular immunotherapy with sipuleucel-T in advanced prostate cancer," Cancer, vol. 115, No. 16, pp. 3670-3679 (Aug. 15, 2009).
International Preliminary Report on Patentability of PCT/US12/20173 dated Jul. 10, 2013.
International Search Report of PCT/US12/20173 dated Apr. 13, 2012.
International Search Report of PCT/US12/25141 dated Jul. 27, 2009.
International Preliminary Report on Patentability of PCT/US2006/034945 dated Mar. 11, 2008.
International Preliminary Report on Patentability of PCT/US2008/057257 dated Sep. 15, 2009.
International Preliminary Report on Patentability of PCT/US2010/48829 dated Mar. 20, 2012.
International Search Report of PCT/US2003/025141 dated Jul. 27, 2009.
International Search Report of PCT/US2006/034945 dated May 23, 2007.
International Search Report of PCT/US2008/057257 dated Aug. 15, 2008.
International Search Report of PCT/US2010/48829 dated Dec. 16, 2010.
Kaufman, et al., "Local and Distant Immunity Induced by intralesional vaccination with an oncolytic herpes virus encoding GM-CSF in patients with stage IIIc and IV melanoma," Ann Surg Oncol., vol. 17, No. 3, pp. 718-730 (Mar. 2010).
Kerr, D., "Clinical Development of Gene Therapy for Colorectal Cancer," Nat. Rev. Cancer, vol. 3, No. 8, pp. 615-622 (Aug. 2003).
Kim, et al., Abstract No. 168: Antitumoral Efficacy of Multiple Injection of JX-594 (Thymidine Kinase (TK) Deleted, Human GM-CSF Inserted Wyeth Strain) Via Tail Vein in NNitrosomorpholine (NNM) Treated Rats), Molecular Therapy, vol. 11, No. 1, S67 (May 2005).
Kim, J., et al., "Systemic Armed Oncolytic and Iimmunologic Therapy for Cancer with JX-594, A Targeted Poxvirus Expressing GM-CSF," Mol. Ther., vol. 14, No. 3, pp. 361-370 (Sep. 14, 2006).
Kirn, D. H., et al., "Targeting of Interferon-Beta to Produce a Specific, Multi-Mechanistic Oncolytic Vaccinia Virus," PLoS Med., vol. 4, No. 12, e353 (Dec. 2007).
Lee, J., et al., "Oncolytic and Immunostimulatory Efficacy of a Targeted Oncolytic Poxvirus Expressing Human GM-CSF Following Intravenous Administration in a Rabbit Tumor Model," Cancer Gene Ther., vol. 17, No. 2, pp. 73-79 (Feb. 2010).
Le Tourneau, C., et al., "New Developments in Multitargeted Therapy for Patients with Solid Tumours," Cancer Treat Rev., vol. 34, pp. 37-48 (2008).
Li, Q.X., et al., "Oncolytic Virotherapy As a Personalized Cancer Vaccine," Int. J Cancer, vol. 123, No. 3, pp. 493-499 (Aug. 1, 2008).
Li, H., et al., "Induction of Strong Antitumor Immunity by an HSV-2-Based Oncolytic Virus in a Murine Mammary Tumor Model," J Gene Med., vol. 9, No. 3, pp. 161-169 (Mar. 2007).
Liu, et al., "The Targeted Oncolytic Poxvirus JX-594 Demonstrates Antitumoral, Antivascular, and Anti-HBV Activities in Patients with Hepatocellular Carcinoma," Molecular Therapy, vol. 16, No. 9, pp. 1637-1642 (2008).

Liu, Z., et al., "Cytokine Enhancement of In Vitro Antibody-Dependent Cellular Cytotoxicity Mediated by Chimeric Anti-GD3 Monoclonal Antibody KM871," Cancer Immun., vol. 2, No. 13, pp. (Oct. 2002).
Llovet, J., "Sorafenib in Advanced Hepatocellular Carcinoma (HCC)." N. Engl. J. Med., vol. 359, pp. 378-390 (2008).
Liu, T., et al., "Translation of Targeted Oncolytic Virotherapeutics From the Lab into the Clinic, and Back Again: A High-Value Iterative Loop," Mol. Ther., vol. 16, No. 6, pp. 1006-1008 (Jun. 2008).
McCormick, F., "Cancer Gene Therapy: Fringe or Cutting Edge?" Nature, vol. 1, pp. 130-141 (Nov. 2001).
Mineta, T., et al., "Treatment of Malignant Gliomas Using Ganciclovir-Hypersensitive, Ribonucleotide Reductase-Deficient Herpes Simplex Viral Mutant," Cancer Res., vol. 54, No. 15, pp. 3963-3966 (Aug. 1994).
Morris, J.C., et al., "Antibody-Based Therapy of Leukaemia," Expert Rev Mol Med., vol. 11, No. e29, 2009.
Moss, Fields Virology., Fifth Edition), Lippincott-Raven Publishers: Philadelphia, pp. 2905-2945 (2007).
Motzer, R. J., et al., "Sunitinib in Patients with Metastatic Renal Cell Carcinoma," JAMA, vol. 295, No. 21, pp. 2516-2524 (2006).
NCT 01171651 on Jul. 27, 2010, ClinicalTrials.gov Archive pp. 1-4 (Jul. 27, 2010).
Norman, K., et al., "Reovirus As a Novel Oncolytic Agent," J Clin. Invest., vol. 105, No. 8, pp. 1035-1038 (Apr. 2000).
Parato, K.A., et al., "Diplomatic Immunity: Turning a Foe Into an Ally," Curr Opin Mol Ther., vol. 11 No. 1, pp. 13-21 (Feb. 2009).
Park, B.H., et al., "Use of a Targeted Oncolytic Poxvirus, JX-594, in Patients with Refractory Primary or Metastatic Liver Cancer: A Phase I Trial." Lancet Oncology, vol. 9, pp. 533-542 (2008).
Payne, L., "Significance of Extracellular Enveloped Virus in the In Vitro and In Vivo Dissemination of Vaccinia," J Gen Virol., vol. 50, No. 1, pp. 89-100 (Sep. 1980).
Petrelli A., et al., "From Single- to Multi-Target Drugs in Cancer Therapy: When Aspecificity Becomes an Advantage," Current Medicial Chemistry, vol. 15, pp. 422-432 (2008).
Podar, K., et al., "The Small-Molecule VEGF Receptor Inhibitor Pazopanib (GW786034B) Targets Both Tumor and Endothelial Cells in Multiple Myeloma," Proc. Natl. Acad. Sci. U S A., vol. 103, No. 51, pp. 19478-19483 (Dec. 19, 2006).
Prestwich, R.J., et al., "Immune-mediated antitumor activity of reovirus is required for therapy and is independent of direct viral oncolysis and replication," Clin. Cancer Res., vol. 15, No. 13, pp. 4374-4381 (2009).
Qin, et al., "Cancer Gene Therapy Using Tumor Cells Infected with Recombinant Vaccinia Virus Expressing GM-CSF," Human Gene Therapy, vol. 5, pp. 1853-1860 (1996).
Racila, E., et al., "A polymorphism in the Complement Component C1qA Correlates with Prolonged Response Following Rituximab Therapy of Follicular Lymphoma," Clin Cancer Res., vol. 14, No. 20, pp. 6697-6703 (Oct. 15, 2008).
Reid, T., "Fighting Fire with Fire: Effects of Oncolytic Virotherapy on Underlyilng Viral Hepatitis in Hepatocellular Carcinoma," Molecular Therapy, vol. 16, No. 9, pp. 1521-5123 (Sep. 1, 2008).
Remington's Pharmaceutical Sciences, vol. 157, pp. 1035-1038 and 1570-1580 (1990).
Rosenberg, S., et al., "Cancer Immunotherapy: Moving Beyond Current Vaccines," Nature Medicine, vol. 10, No. 9, pp. 909-915 (Sep. 2004).
Sambrook, et al., Molecular Cloning: A Laboratory Manual, 2nd Edition, Cold Spring Harbor, Laboratory Press, Cold Spring Harbor, New York, pp. 4-12 (1989).
Sandhu, et al., Expert Review of Gastroenterology & Hepatology, vol. 2, No. 1, pp. 81-92 (Feb. 2008).
Senzer, N., et al., "Phase II Clinical Trial of a Granulocyte-macrophage Colony-Stimulating Factor-Encoding, Second-Generation Oncolytic Herpesvirus in Patients with Unresectable Metastatic Melanoma," J Clin Oncol, vol. 27, No. 34, pp. 5763-5771 (Dec. 1, 2009).
Stojdl, D., et al., "Exploiting Tumor-Specific Defects in the Interferon Pathway With a Previously Unknown Oncolytic Virus," Nat. Med., vol. 6, No. 7, pp. 821-825 (Jul. 2000).

(56) References Cited

OTHER PUBLICATIONS

Stojdl, D., et al., "VSV Strains with Defects in their Ability to Shutdown Innate Immunity are Potent Systemic Anti-Cancer Agents." Cancer Cell, vol. 4, No. 4, pp. 263-275 (Oct. 2003).
"The 14th Annual Meeting 2008 Japan Society of Gene Therapy," The Journal of Gene Medicine, vol. 11, No. 12, pp. 11383-1193 (Nov. 25, 2009).
"The 14th Annual Meeting 2008 Japan Society of Gene Therapy Program and Abstracts," retrieved from the internet on Feb. 14, 2014—URL:http://jsgt.jp/annual-eeting/08JSGT/14-program2008.pdf.
Thorne, S., et al., "Oncolytic Virotherapy: Approaches to Tumor Targeting and Enhancing Antitumor Effects," Semin. Oncol., vol. 6, pp. 537-548 (Dec. 2005).
Vanderplasschen and Smith, "A Novel Virus Binding Assay Using Confocal Microscopy: Demonstration that the Intracellular and Extracellular Vaccinia Virions Bind to Different Cellular Receptors," J. Virol., vol. 71, No. 5, pp. 4032-4041 (1997).
Vanderplasschen and Smith, "Intracellular and Extracellular Vaccinia Virions enter Cells by Different Mechanisms," J. Gen. Virol., vol. 79 (Part 4) pp. 877-887 (1998).
Walport, M., "Complement. First of two parts," N Engl J Med., vol. 344, No. 14, pp. 1058-1066 (Apr. 5, 2001).
Wang, H,. et al., "A Recombinant Adenovirus Type 35 Fiber Knob Protein Sensitizes Lymphoma Cells to Rituximab Therapy," Blood. vol. 115, No. 3, pp. 592-600 (Jan. 2010).
Weiner, L. M., et al., "Monoclonal Antibodies: Versatile Platforms for Cancer Immunotherapy," Nat Rev Immunol., vol. 10, No. 5, pp. 317-327 (May 2010).
Written Opinion of PCT/US2010/48829 dated Dec. 16, 2010.
Written Opinion of PCT/US06/034945 dated Mar. 23, 2007.
Written Opinion of PCT/12/20173 dated Apr. 13, 2012.
Zeimet, A., et al., "Why did p53 Gene Therapy Fail in Ovarian Cancer?" Lancet Oncol., vol. 4, pp. 415-422 (Jul. 2003).
Zent, C. S., et al., Direct and Complement Dependent Cytotoxicity in CLL Cells From Patients with High-Risk Early-Intermediate Stage Chronic Llymphocytic Leukemia (CLL) Treated With Alemtuzumab and Rituximab., Leuk Res., vol. 32, No. 12, pp. 1849-1856, (Dec. 2008).
U.S. Appl. No. 13/535,291—Final office action dated Apr. 23, 2014.
U.S. Appl. No. 13/535,291—Non-final office action dated Jan. 9, 2014.
U.S. Appl. No. 13/535,291—Non-final office action dated May 31, 2013.
U.S. Appl. No. 13/535,291—Final office action dated Sep. 13, 2013.
U.S. Appl. No. 11/838,774—Restriction Requirement dated Nov. 19, 2009.
U.S. Appl. No. 12/531,353—Non-final office action dated Jan. 27, 2012.
U.S. Appl. No. 12/531,353—Final office action dated Jul. 9, 2012.
U.S. Appl. No. 13/395,929—Restriction Requirement dated Apr. 4, 2013.
U.S. Appl. No. 13/395,929—Non-final office action dated May 10, 2013.
U.S. Appl. No. 13/395,929—Final office action dated Sep. 3, 2013.
U.S. Appl. No. 13/395,929—Notice of Allowance dated Jan. 31, 2014.
U.S. Appl. No. 11/838,757—Final office action dated Dec. 13, 2010.
U.S. Appl. No. 11/838,757—Non-final office action dated Jul. 26, 2011.
U.S. Appl. No. 11/838,757—Final office action dated Nov. 10, 2011.
U.S. Appl. No. 11/838,757—Advisory Action dated Apr. 25, 2012.
U.S. Appl. No. 11/838,757—Non-final office action dated May 29, 2012.
U.S. Appl. No. 11/838,757—Notice of Allowance dated Aug. 15, 2012.
Almendro, N., et al., "Cloning of the Human Platelet Endothelial Cell Adhesion Molecule-1 Promoter and Its Tissue-Specific Expression," Immunol., vol. 157, No. 12, pp. 5411-5421 (Dec. 15, 1996).
Amato, R., et al., "Targeted Anti-Cancer Therapies for Renal Cancer," Drugs, vol. 66, No. 17, pp. 2161-2171 (Dec. 2006).
Ananvoranich S., et al., "Duplication of a Region in the Multiple Cloning Site of a Plasmid Vector to Enhance Cloning-Mediated Addition of Restriction Sites to a DNA Fragment," Biotechniques, vol. 23, No. 5, pp. 814-816 (Nov. 1997).
Angel, P., et al., "Phorbol Ester-Inducible Genes Contain a Common Cis Element Recognized by a TPA-Modulated Trans-Acting Factor," Cell, vol. 49, pp. 729-739 (Jun. 19, 1987).
Angel, P., et al., "12-O-tetradecanoyl-phorbol-13-acetate Induction of the Human Collagenase Gene Is Mediated by an Inducible Enhancer Element Located in the 5'-flanking Region," Mol. Cell. Biol., vol. 7, pp. 2256-2266 (Jun. 1987).
Arap, W., et al., "Replacement of the p16/CDKN2 Gene Suppresses Human Glioma Cell Growth," Cancer Res., vol. 55, No. 6, pp. 1351-1354 (Mar. 15, 1995).
Arness, M., et al., "Myopericarditis Following Smallpox Vaccination," Am. J. Epidemiol., vol. 160, pp. 642-651 (Apr. 2004).
Atchinson, M., et al., "The Role of the k Enhancer and Its Binding Factor Nf-KB in the Developmental Regulation of K Gene Transcription," Cell, vol. 48, pp. 121-128 (Jan. 16, 1987).
Atchinson, P., "Tandem Kappa Immunoglobulin Promoters Are Equally Active in the Presence of the Kappa Enhancer: Implications for Models of Enhancer Function," Cell, vol. 46, pp. 253-262 (Jul. 18, 1986).
Bajorin, D., et al., "Comparison of Criteria for Assigning Germ Cell Tumor Patients to 'Good Risk' and 'Poor Risk' Studies," J. Clin. Oncol., vol. 6, No. 5, pp. 786-792 (May 1988).
Bakhshi, A., et al., "Cloning the Chromosomal Breakpoint of t(14;18) Human Lymphomas: Clustering around Jh on Chromosome 14 and near a Transcriptional Unit on 18," Cell, vol. 41, No. 3, pp. 899-906 (Jul. 1985).
Banerji, J., et al., "Expression of a β-Globin Gene Is Enhanced by Remote SV40 DNA Sequences," Cell, vol. 27, pp. 299-308 (Dec. 1981).
Banerji, J., et al., "A Lymphocyte-Specific Cellular Enhancer Is Located Downstream of the Joining Region in Immunoglobulin Heavy Chain Genes," Cell, vol. 33, No. 3, pp. 729-740 (Jul. 1983).
Bellus, D., "How do Specialty Polymers Modify the Chemical and Pharmaceutical Industries," Macromol. Sci. Pure Appl. Chem., vol. A31, No. 1, pp. 1355-1376 (Oct. 1994).
Berkhout, B., et al., "Tat trans-activates the human immunodeficiency virus through a nascent RNA target," Cell, vol. 59, pp. 273-282 (Oct. 20, 1989).
Blanar, M., et al., "A gamma-interferon-induced factor that binds the interferon response sequence of the MHC class I gene, H-2Kb," Embo J., vol. 8, pp. 1139-1144 (Apr. 1989).
Bodine, D., et al., "An enhancer element lies 3' to the human a gamma globin gene.," Embo J., vol. 6, pp. 2997-3004 (Oct. 1987).
Boshart, M., et al., "A very strong enhancer is located upstream of an immediate early gene of human cytomegalovirus," Cell, vol. 41, pp. 521-530 (Jun. 1985).
Bosze, Z., et al., "A transcriptional enhancer with specificity for erythroid cells is located in the long terminal repeat of the Friend murine leukemia virus," Embo J., vol. 5, No. 7, pp. 1615-1623 (Jul. 1986).
Braddock, M., et al., "HIV-1 TAT 'activates' presynthesized RNA in the nucleus," Cell. vol. 58, p. 269-279 (Jul. 28, 1989).
Braisted, A., et al., "Minimizing a binding domain from protein A," Proc. Natl. Acad. Sci. USA, vol. 93, No. 12, pp. 5688-5692 (Jun. 1996).
Bretibach, C. J., et al., "Intravenous Delivery of a Multi-Mechanistic Cancer-Targeted Oncolytic Poxvirus in Humans," vol. 477, pp. 99-102 (Sep. 2011).
Brizel, D., Radiotherapy and concurrent chemotherapy for the treatment of locally advanced head and neck squamous cell carcinoma: Semin. Radiat. Oncol., vol. 8, No. 4, pp. 237-246 (Oct. 1998).
Bulla, G., et al., "The hepatitis B virus enhancer modulates transcription of the hepatitis B virus surface antigen gene from an internal location" Journal of Virol., vol. 62, No. 4, pp. 1437-1441 (Apr. 1988).
Burton, D., et al., "Human Antibodies from Combinatorial Libraries," Advances in Immunology, vol. 57, pp. 191-280 (Nov. 1994).

(56) References Cited

OTHER PUBLICATIONS

Caldas, C., et al., "Detection of K-ras Mutations in the Stool of Patients with Pancreatic Adenocarcinoma and Pancreatic Ductal Hyperplasia," Cancer Research, vol. 54, pp. 3568-3573 (Jul. 1, 1994).
Caldas, C., et al., "Frequent somatic mutations and homozygous deletions of the p16 (MTS1) gene in pancreatic adenocarcinoma," Nat. Genet., vol. 8, No. 1, pp. 27-32 (Sep. 1994).
Campbell, B., et al., "Functional Analysis of the Individual Enhancer Core Sequences of Polyomavirus: Cell-Specific Uncoupling of DNA Replication from Transcription," Mol. Cell Biol., vol. 8, pp. 1993-2004 (May 1988).
Camper, S., et al., "Postnatal repression of the alpha-fetoprotein gene is enhancer independent," Genes Dev., vol. 3, pp. 537-546 (Feb. 15, 1989).
Campo, M., et al., "Transcriptional control signals in the genome of bovine papillomavirus type 1," Nature, vol. 303, pp. 77-80 (May 5-11, 1983).
Carbonelli, D., et al., "A plasmid vector for isolation of strong promoters in *Escherichia coli*," Fems Microbiol. Lett, vol. 177, No. 1, pp. 75-82 (Jun. 7, 1999).
Cebon, J., et al., "The dissociation of GM-CSF efficacy from toxicity according to route of administration: a pharmacodynamic study," Br. J. Haematol., vol. 80, No. 2, pp. 144-150 (Feb. 1992).
Celander, D., et al., "Glucocorticoid regulation of murine leukemia virus transcription elements is specified by determinants within the viral enhancer region," Virology, vol. 61, pp. 269-275 (Feb. 1987).
Celander, D., et al., "Regulatory elements within the murine leukemia virus enhancer regions mediate glucocorticoid responsivene," Virology, vol. 62, pp. 1314-1322 (Apr. 1988).
Chandler, V., et al., "DNA sequences bound specifically by glucocorticoid receptor in vitro render a heterologous promoter hormone responsive in vivo," Cell., vol. 33, pp. 489-499 (Jun. 1983).
Chandler, S., et al., "RNA splicing specificity determined by the coordinated action of RNA recognition motifs in SR proteins," Proc. Natl. Acad. Sci. USA, vol. 94, No. 8, pp. 3596-3601 (Apr. 1997).
Chang, S., et al., "Glucose-regulated protein (GRP94 and GRP78) genes share common regulatory domains and are coordinately regulated by common trans-acting factors," vol. Cell. Biol., vol. 9, No. 5, pp. 2153-2162 (May 1989).
Chatterjee, V., et al., "Negative regulation of the thyroid-stimulating hormone a gene by thyroid hormone: Receptor interaction adjacent to the TATA box," Proc. Natl. Acad. Sci. USA, vol. 86, pp. 9114-9118 (Dec. 1989).
Chen, C., et al., "High-efficiency transformation of mammalian cells by plasmid DNA," Mol. Cell. Biol., vol. No. 7, No. 8, pp. 2745-2752 (Aug. 1987).
Cheng, J., et al., "p16 Alterations and Deletion Mapping of 9p21-p22 in Malignant Mesothelioma." Cancer Res., vol. 54, No. 21, pp. 5547-5551 (Nov. 1, 1994).
Choi, K., et al., "An altered pattern of cross-resistance in multidrug-resistant human cells results from spontaneous mutations in the mdr1 (P-glycoprotein) gene," Cell, vol. 53, pp. 519-529 (May 1988).
Choi, H., et al., "Correlation of Computed Tomography and Positron Emission Tomography in Patients With Metastatic Gastrointestinal Stromal Tumor Treated at a Single Institution With Imatinib Mesylate: Proposal of New Computed Tomography Response Criteria," J. Clin. Oncol., vol. 25, No. 13, pp. 1753-1759 (May 1, 2007).
Cleary, M., et al., "Detection of a second t(14;18) breakpoint cluster region in human follicular lymphomas," J. Exp. Med., vol. 164, No. 1, pp. 315-320 (Jul. 1986).
Cleary, M., et al., "Nucleotide sequence of a t(14;18) chromosomal breakpoint in follicular lymphoma and demonstration of a breakpoint-cluster region near a transcriptionally active locus on chromosome 18," Proc. Natl. Acad. Sci. USA, vol. 21, pp. 7435-7443 (Nov. 1985).
Cohen, J., et al., "A Repetitive Sequence Element 3' of the Human c-Ha-ras1 Gene Has Enhancer Activity," J Cell Physiol. Supplement, vol. 133, Issue S5, pp. 75-81 (Dec. 1987).
Cooley, L., et al., "Insertional Mutagenesis of the *Drosophila* Genome with Single P Elements," Science, vol. 239, No. 4844, pp. 1121-1128 (Mar. 4, 1988).
Costa, R., et al., "The Cell-Specific Enhancer of the Mouse Transthyretin (Prealbumin) Gene Binds a Common Factor at One Site and a Liver-Specific Factor(s) at Two Other Sites, " Mol. Cell. Biol., vol. 8, pp. 81 (Jan. 1988).
Cripe, T., et al., "Transcriptional regulation of the human papillomavirus-16 E6-E7 promoter by a keratinocyte-dependent enhancer, and by viral E2 trans-activator and repressor gene products: implications for cervical carcinogenesis," Embo J. vol. 6, pp. 3745-3753 (Dec. 1987).
Culotta, V., et al., "Fine mapping of a mouse metallothionein gene metal response element," Mol. Cell Biol., vol. 9, pp. 1376-1380 (Mar. 1989).
Culver, K., et al., "In vivo gene transfer with retroviral vector-producer cells for treatment of experimental brain tumors," Science, vol. 156, No. 5603, pp. 1550-1552 (Jun. 12, 1992).
Cunningham, B., et al., "High-resolution epitope mapping of hGH-receptor interactions by alanine-scanning mutagenesis," Science, vol. 244, No. 4908, pp. 1081-1085 (Jun. 2, 1989).
Curran, W., "Radiation-Induced Toxicities: The Role of Radioprotectants," Seminars Radiat. Oncol., vol. 8, Supp. 4, pp. 2-4 (Oct. 1998).
Dandolo, L., et al., "Regulation of Polyoma Virus Transcription in Murine Embryonal Carcinoma Cells," J. Virology, vol. 47, pp. 55-64 (Jul. 1983).
Deschamps, J., et al., "Identification of a transcriptional enhancer element upstream from the proto-oncogene fos," Science, vol. 230, pp. 1174-1177 (Dec. 6, 1985).
DeVilliers, J., et al., "Polyoma virus DNA replication requires an enhancer," Nature, vol. 312, No. 5991, pp. 242-246 (Nov. 1984).
Dillman, R., "Perceptions of Herceptin®: A Monoclonal Antibody for the Treatment of Breast Cancer," Biother. Radiopharm., vol. 14, No. 1, pp. 5-10 (Jan. 29, 2009).
Edbrooke, M., et al., "Identification of cis-Acting Sequences Responsible for Phorbol Ester Induction of Human Serum Amyloid a Gene Expression via a Nuclear Factor KB-Like Transcription Factor," Mol. Cell Biol., vol. 9, pp. 1908 (May 1989).
Edlund, T., et al., "Cell-specific expression of the rat insulin gene: evidence for role of two distinct 5' flanking elements," Science, vol. 230, pp. 912-916 (Nov. 22, 1985).
El-Kareh, A., "Theoretical models for drug delivery to solid tumors," Crit. Rev. Biomed. Eng., vol. 25, No. 6, pp. 503-571 (Feb. 1997).
Erlandsson, R., "Molecular Genetics of Renal Cell Carcinoma," Cancer Genet. Cytogenet., vol. 104, No. 1, pp. 1-18 (Jul. 1998).
Fechheimer, M., et al., "Transfection of mammalian cells with plasmid DNA by scrape loading and sonication loading," Proc. Natl. Acad. Sci. USA, vol. 84, pp. 8463-8467 (Dec. 1987).
Feng, S., et al., "HIV-1 tat trans-activation requires the loop sequence within tar," Nature, vol. 334, pp. 165-167 (Jul. 14, 1988).
Firak, T., et al., "Minimal Transcriptional Enhancer of Simian Virus 40 Is a 74-Base-Pair Sequence That Has Interacting Domains," Mol. Cell. Biol., vol. 6, pp. 3667-3676 (Nov. 1986).
Foecking, M., et al., "Powerful and Versatile Enhancer-Promoter Unit for Mammalian Expression Vectors," Gene, vol. 45, No. 1, pp. 101-105 (Jun. 5, 1986).
Force, T., et al., "Cardiotoxicity of the new cancer therapeutics—mechanisms of, and approaches to, the problem," Drug Discovery Today, vol. 13, No. 17/18, pp. 778-784 (Sep. 2008).
Fraley, T., et al., "Entrapment of a bacterial plasmid in phospholipid vesicles: potential for gene transfer," Proc. Natl. Acad. Sci. USA, vol. 76, pp. 3348-3352 (Jul. 1979).
Fujita, T., et al., "Interferon-p Gene Regulation: Tandemly Repeated Sequences of a Synthetic 6 by Oligomer Function As a Virus-Inducible Enhancer," Cell, vol. 49, pp. 357-367 (May 8, 1987).
Gertig, D., et al., "Genes and environment in the etiology of colorectal cancer," Semin. Cancer Biol., vol. 8, No. 4, pp. 285-298 (Aug. 1998).
Gilles, S., et al., "A tissue-specific transcription enhancer element is located in the major intron of a rearranged immunoglobulin heavy chain gene," Cell, vol. 33, pp. 717-728 (Jul. 1983).

(56) References Cited

OTHER PUBLICATIONS

Gloss, B., et al., "The upstream regulatory region of the human papilloma virus-16 contains an E2 protein-independent enhancer which is specific for cervical carcinoma cells and regulated by glucocorticoid hormones," Embo. J., vol. 6, pp. 3735-3743 (Dec. 1, 1987).
Gnant, M., et al., "Regional Versus Systemic Delivery of Recombinant Vaccinia Virus as Suicide Gene Therapy for Murine Liver Metastases," Ann Surg., vol. 230, No. 3, pp. 352-360 (Sep. 1999).
Gnant, M., et al., "Tumor-Specific Gene Delivery Using Recombinant Vaccinia Virus in a Rabbit Model of Liver Metastases," J. Ntl. Cancer Inst., vol. 91, No. 20, pp. 1744-1750 (Oct. 20, 1999).
Godbout, R., et al., "Fine-Structure Mapping of the Three Mouse α-Fetoprotein Gene Enhancers," Mol. Cell Biol., vol. 8, pp. 1169-1178 (Mar. 1988).
Goodbourn, S., et al., "The human β-interferon gene enhancer is under negative control," Cell, vol. 45, pp. 601-610 (May 23, 1986).
Goodbourn, S., et al., "Overlapping positive and negative regulatory domains of the human,ß-interferon gene," Proc. Atl. Acad. Sci. USA, vol. 85, p. 1447-1451 (Mar. 1988).
Gopal, T., "Gene Transfer Method for Transient Gene Expression, Stable Transformation, and Cotransformation of Suspension Cell Cultures," Mol. Cell Biol,. Vol , pp. 1188-1190 (May 1985).
Graham, F. L., et al., "A new technique for the assay of infectivity of human adenovirus 5 DNA," Virology, vol. 52, No. 2, pp. 456-467 (Apr. 1973).
Greene, W., et al. "HIV-1, iITLV-1 and normal T-cell growth: transcriptional strategies and surprises," Immunology Today, vol. 10, pp. 272-278 (Aug. 1989).
Gross, A., et al., "BCL-2 family members and the mitochondria in apoptosis," Genes Dev, vol. 13, No. 15, pp. 1899-1911 (Aug. 1999).
Grosschedl, R., et al., "Cell-Type Specificity of Immunoglobulin Gene Expression is Regulated by at Least Three DNA Sequence Elements," Baltimore Cell, vol. 41, pp. 885-897 (Jul. 1985).
Haanen, J., et al., "Melanoma-specific tumor-infiltrating lymphocytes but not circulating melanoma-specific T cells may predict survival in resected advanced-stage melanoma patients," Cancer Immunol. Immunother., vol. 55, No. 4, pp. 451-458 (Apr. 2006).
Harland, R., et al., "Translation of mRNA injected into *Xenopus oocytes* is specifically inhibited by antisense RNA," J Cell Biol., vol. 101, No. 3, pp. 1094-1099 (Sep. 1985).
Haslinger, A., et al., "Upstream promoter element of the human metallothionein-IIA gene can act like an enhancer element," Natl. Acad. Sci. USA, vol. 82, pp. 8572-8576 (Dec. 1985).
Hauber, J., et al., "Mutational Analysis of the trans-Activation-Responsive Region of the Human Immunodeficiency Virus Type I Long Terminal Repeat," J. Virology, vol. 62, No. 3, pp. 673-679 (Mar. 1988).
Heise, C., et al., "Efficacy of a replication-competent adenovirus (ONYX-015) following intratumoral injection: intratumoral spread and distribution effects," Cancer Gene Ther., vol. 6, No. 6, pp. 499-504 (Jun. 1, 1999).
Hen, R., et al., "A mutated polyoma virus enhancer which is active in undifferentiated embryonal carcinoma cells is not repressed by adenovirus-2 E1 A products," Nature, vol. 32, pp. 249-251 (May 1986).
Hensel, G., et al., "PMA-responsive 5' flanking sequences of the human TNF gene," Llymphokine Res., vol. 8, No. 3, pp. 347-351 (Fall 1989).
Ho., Y., et al., "Reduced Fertility in Female Mice Lacking Copper-Zinc Superoxide Dismutase," J. Biol. Chem., vol. 27, No. 13, pp. 7765-7769 (Mar. 27, 1998).
Hussussian, C., et al., "Germline p16 mutations in familial melanoma," Nat. Genet., vol. 8, No. 1, pp. 15-21 (Sep. 1994).
Inouye , S., et al., "Up-promoter mutations in the Ipp gene of *Escherichia coli*," Nucleic Acids Res. vol. 13, pp. 3101-3109 (May 10, 1985).
Irie, R., et al., "Regression of cutaneous metastatic melanoma by intralesional injection with human monoclonal antibody to ganglioside GD2," Proc. Natl. Acad. Sci, USA, vol. 83, No. 22, pp. 8694-8698 (Nov. 1986).
Irie, et al., "Human monoclonal antibody to gang lioside GM2 for melanoma treatment," Lancet., vol. 1, No. 8641, pp. 786-787 (Apr. 1989).
Johnson M ., et al., "Apoptosis regulating genes in prostate cancer (review)," Oncol. Rep., vol. 5, No. 3, pp. 553-557 (May 1, 1998).
Ju, D., et al., "Interleukin-18 gene transfer increases antitumor effects of suicide gene therapy through efficient induction of antitumor immunity," Gene Ther., vol. 7, No. 19, pp. 1672-1679 (Jul. 2000).
Ju, W., et al., "Selective Neuronal Survival and Upregulation of PCNA in the Rat Inner Retina Following Transient Ischemia," J Neuropathol. Exp. Neurol., vol. 59, No. 3, pp. 241-250 (Mar. 2000).
Kaeppler, H., et al., "Silicon carbide fiber-mediated DNA delivery into plant cells," Plant Cell Reports, vol. 9, pp. 415-418 (Dec. 1990).
Kamb, A., et al., "Analysis of the p16 gene (CDKN2) as a candidate for the chromosome 9p melanoma susceptibility locus," Nat. Genet., vol. 8, No. 1, pp. 22-26 (Sep. 1994).
Kamb, A., et al., "A cell cycle regulator potentially involved in genesis of many tumor types," Science, vol. 264, No. 5157, pp. 436-440 (Apr. 15, 1994).
Kaneda, Y., et al., "Increased expression of DNA cointroduced with nuclear protein in adult rat liver," Science, vol. 243, pp. 375-378 (Jan. 1989).
Kato, J., et al., "Cyclic GMP Down-regulates Atrial Natriuretic Peptide Receptors on Cultured Vascular Endothelial Cells," J Biol Chem., vol. 266, No. 22, pp. 3361-3364 (Aug. 5, 1991).
Kerr, J., et al., "Apoptosis: A Basic Biological Phenomenon With Wideranging Implications in Tissue Kinetics," Br. J. Cancer, vol. 26, No. 4, pp. 239-257 (Apr. 1972).
Kolmel, H., "Cytology of neoplastic meningosis," J. Neurooncol., vol. 38, No. 2-3, pp. 121-125 (Jun. 1998).
Kraus, J., et al., "Alternative promoter usage and tissue specific expression of the mouse somatostatin receptor 2 gene," FEBS Lett., vol. 428, No. 3, pp. 165-170 (Apr. 21, 1998).
Kulesh, D., et al., "Smallpox and pan-Orthopox Virus Detection by Real-Time 3—Minor Groove Binder TaqMan Assays on the Roche LightCycler and the Cepheid Smart Cycler Platforms," J. Clin. Microbiol., vol. 42, No. 2, pp. 601-609 (Feb. 2004).
Kyte J., et al., "A simple method for displaying the hydropathic character of a protein," J. Mol. Biol., vol. 157, No. 1, pp. 105-132 (May 5, 1982).
Lareyre, J., et al., "A 5-Kilobase Pair Promoter Fragment of the Murine Epididymal Retinoic Acid-binding Protein Gene Drives the Tissue-specific, Cell-specific, and Androgen-regulated Expression of a Foreign Gene in the Epididymis of Transgenic Mice," J. Biol. Chem., vol. 274, No. 12, pp. 8282-8290 (Mar. 19, 1999).
Lee, J., et al., "The Highly Basic Ribosomal Protein L41 Interacts with the b Subunit of Protein Kinase CKII and Stimulates Phosphorylation of DNA Topoisomerase IIa by CKII," Biochem. Biophys. Res. Commun., vol. 238, No. 2, pp. 462-467 (Jul. 29, 1997).
Legrand, F., et al., "Vaccinia viruses with a serpin gene deletion and expressing IFN-γ induce potent immune responses without detectable replication in vivo," PNAS, vol. 102, No. 8, pp. 2940-2945, (Feb. 2005).
Levenson, V., et al., "Internal Ribosomal Entry Site-Containing Retroviral Vectors with Green Fluorescent Protein and Drug Resistance Markers ," Hum. Gene Ther., vol. 9, No. 8, pp. 1233-1236 (May 20, 1998).
Li, C., et al., Cytokine and Immuno-Gene Therapy for Solid Tumors, Cellular & Molecular Immunology, vol. 2, No. 2, pp. 81-91 (Apr. 2005).
Liebermann, D., "Normal development, oncogenesis and programmed cell death," Oncogene, vol. 17, No. 10, pp. 1189-1894 (Aug. 4, 1998).
Loparev, V., et al., "A third distinct tumor necrosis factor receptor of orthopoxviruses," Proc Natl Acad Sci USA, vol. 95, pp. 3789-3791, (Mar. 1998).
Macejak, D., et al., "Internal initiation of translation mediated by the 5' leader of a cellular mRNA," Nature, vol. 353, pp. 90-94 (Sep. 1991).

(56) References Cited

OTHER PUBLICATIONS

Magi-Galluzzi, C., et al., "Proliferation, apoptosis and cell cycle regulation in prostatic carcinogenesis," Anal. Quant. Cytol. Histol., vol. 20, No. 5, pp. 343-250 (Oct. 1998).

Mahvi, D., et al., "Phase I/IB study of immunization with autodgous tumor cells transfected with the GM-CSF gene by particle-mediated transfer in patients with melanoma or sarcoma," Human Gene Therapy, vol. 5, pp. 875-891 (May 1997).

Marshall, J., et al., "Phase I study in advanced cancer patients of a diversified prime-and-boost vaccination protocol using recombinant vaccinia virus and recombinant nonreplicating avipox virus to elicit anti-carcinoembryonic antigen immune responses," J Clin Oncol, vol. 18, No. 23, pp. 3964-3973 (Dec. 2000).

Mangray, S., et al., "Molecular Pathobiology of Pancreatic Adenocarcinoma," Front Biosci., vol. 3, pp. D1148-D116 (Nov. 15, 1998).

Marsters, S., et al., "Control of apoptosis signaling by Apo2 ligand," Recent Prog. Horm. Res., vol. 54, pp. 225-234 (Annual Publication—1999).

Mastrangelo, M., et al., "Cellular vaccine therapies for cancer," Cancer Treat Res., vol. 94, pp. 35-50 (Annual Publication—1998).

Mathew, E., et al., "The Extracellular Domain of Vaccinia Virus Protein B5R Affects Plaque Phenotype, Extracellular Enveloped Virus Release, and Intracellular Actin Tail Formation," J. Virol, vol. 72, No. 3, pp. 2429-2438 (Mar. 1998).

Mathew, et al., "A mutational analysis of the vaccinia virus B5R protein," J Gen Virol., vol. 82, pp. 1199-1213, (May 2001).

Mayer, R., et al., "CT Number Distribution and Its Association With Local Control and as a Marker of Lung Tumor Response to Radiation," Radiat. Oncol. Investig., vol. 6, No. 6, pp. 281-288 (Sep. 1998).

McCart, J, et al., "Systemic cancer therapy with a tumor-selective vaccinia virus mutant lacking thymidine kinase and vaccinia growth factor genes," Cancer Res, vol. 61, pp. 8751-8757 (Dec. 2001).

McIntosh, A., et al., "Vaccinia virus glycoprotein A34R is required for infectivity of extracellular enveloped virus," J. Virol., vol. 70, pp. 272-228 (Jan. 1996).

Mineta, T., et al., "Attenuated Multi-Mutated Herpes Simplex Virus-1 for the Treatment of Malignant Gliomas," Nat Med., vol. 1, No. 9, pp. 938-943 (Sep. 1995).

Mitchell, M., et al., "Active-specific immunotherapy for melanoma," J. Clin. Oncol, vol. 8, No. 5, pp. 856-869 (May 1990).

Mitchell, M., et al., "Active Specific Immunotherapy of Melanoma with Allogeneic Cell Lysates Rationale, Results, and Possible Mechanisms of Action," Ann. NY Acad. Sci., vol. 690, pp. 153-166 (Aug. 1993).

Mori, T., et al., "Frequent Somatic Mutation of the MTS1/CDK4I (Multiple Tumor SuppressorICyclin-dependent Kinase 4 Inhibitor) Gene in Esophageal Squamous Cell Carcinoma'," Cancer Res., vol. 54, No. 13, pp. 3396-3397 (Jul. 1994).

Morton, D., et al., "Technical details of intraoperative lymphatic mapping for early stage melanoma," Arch. Surg., vol. 127 pp. 392-399 (Apr. 1992).

Mossman, K., et al., "Myxoma virus M-T7, a secreted homolog of the interferon-gamma receptor, is a critical virulence factor for the development of myxomatosis in European rabbits," Virology, vol. 215, No. 1, pp. 17-30, (Jan. 1996).

Mougin, C., et al., "Biology of papillomavirus infections. II. Their role in cervical carcinogenesis," Ann. Bol. Clin., (Paris), vol. 56, No. 1, pp. 21-28 (Jan.-Feb. 1998).

Mullen, J., et al., "Viral Oncolysis," The Oncologist, vol. 7, No. 2, pp. 106-119 (Jan. 2002).

Mumby, M., et al., "Protein phosphatases and DNA tumor viruses: transformation through the back door?" Cell Regul., vol. 2, No. 8, pp. 589-598 (Aug. 1991).

Natoli, G., et al., "Apoptotic, Non-apoptotic, and Anti-apoptotic Pathways of Tumor Necrosis Factor Signalling," Biochem. Pharmacol., vol. 56, No. 8, pp. 915-920 (Oct. 15, 1998).

Ng, A., et al., "The vaccinia virus A41L protein is a soluble 30 kDa glycoprotein that affects virus virulence," J Gen Virol., vol. 82, pp. 2095-2105 (Sep. 2001).

Nicolau, C., et al., "Liposome-mediated DNA transfer in eukaryotic cells: Dependence of the transfer efficiency upon the type of liposomes used and the host cell cycle stage," Biochem. Biophys. Acta, vol. 721, pp. 185-190 (Oct. 11, 1982).

Noguiez-Hellin, P., et al., "Plasmoviruses: Nonviral/viral vectors for gene therapy," Proc. Natl. Acad. Sci. USA, vol. 93, pp. 4175-4180 (Apr. 1996).

Nomoto, S., et al., "Cloning and characterization of the alternative promoter regions of the human LIMK2 gene responsible for alternative transcripts with tissue-specific expression," Gene, vol. 236, No. 2, pp. 259-271 (Jun. 24, 1999).

Ochi, K, et al., "A Case of Small Pancreatic Cancer Diagnosed by Serial Follow-up Studies Promptly by a Positive K-ras Point Mutation in Pure Pancreatic Juice," Am. J. Gastroenterol., vol. 93, No. 8, pp. 1366-1368 (Mar. 6, 1998).

Ohara, K., "Radiotherapy: a significant treatment option in management of prostatic cancer," Gan to Kagaku Ryoho, vol. 25, No. 6, pp. 823-828 (May 1998).

Okamoto, A., et al., "Mutations and altered expression of p16INK4 in human cancer (p53 protein/tumor-suppressor gene/cyclin Di/retinoblastoma protein)," Proc. Natl. Acad. Sci. USA, vol. 9, No. 23, pp. 1104-1109 (Nov. 1994).

Omirulleh, S., et al., "Activity of a chimeric promoter with the doubled CaMV 35S enhancer element in protoplast-derived cells and transgenic plants in maize," Plant Mol. Biol., vol. 21, No. 3, pp. 415-428 (Feb. 1993).

Orlow, I., et al., "Chromosome 9 Allelic Losses and Microsatellite Alterations in Human Bladder Tumors," Cancer Res., vol. 54, No. 11, pp. 2848-2851 (Jun. 1, 1994).

Parato, K. et al., "Recent Progress in the Battle between Oncolytic Viruses and Tumours," Nat Rev Cancer, vol. 5, pp. 965-976 (Dec. 2005).

Payne, L., "Identification of the Vaccinia Hemagglutinin Polypeptide from a Cell System Yielding Large Amounts of Extracellular Enveloped Virus," Journal of Virology, vol. 31, No. 4, pp. 147-155 (Jul. 1979).

Pelletier J., et al., "Internal initiation of translation of eukaryotic mRNA directed by a sequence derived from poliovirus RNA," Nature, vol. 334, No. 6180, pp. 320-325 (Jul. 1988).

Perera, L., et al., "Comparative assessment of virulence of recombinant vaccinia viruses expressing IL-2 and IL-15 in immunodeficient mice," PNAS, vol. 98, No. 9. pp. 5146-5151 (Feb. 2001).

Pietras, R., et al., "Remission of human breast cancer xenografts on therapy with humanized monoclonal antibody to HER-2 receptor and DNA-reactive drugs," Oncogene, vol. 17, No. 17, pp. 2235-2249 (May 1998).

Puhlmann, M., et al., "Vaccinia as a vector for tumor-directed gene therapy: biodistribution of a thymidine kinase-deleted mutant," Cancer Gene Ther., vol. 7, No. 1., pp. 66-73 (Jan. 2000).

Randall, R., et al., "Interferons and Viruses: an Interplay Between Induction, Signalling, Antiviral Responses and Virus Countermeasures," Journal of General Virology, vol. 89, pp. 1-47 (Jan. 2008).

Ravindranath, M., et al., "Role of Gangliosides in Active Immunotherapy with Melanoma Vaccine," Intern. Rev. Immunol., vol. 7, pp. 303-329 (Apr. 26, 1991).

Reading, P., et al., "Vaccinia virus CrmE encodes a soluble and cell surface tumor necrosis factor receptor that contributes to virus virulence," Virology, vol. 292, No. 2, pp. 285-98 (Jan. 2002).

Reagan-Shaw, S., et al., "Dose Translation From Animal to Human Studies Revisited," FASEB Journal, vol. 22, pp. 659-661 (Mar. 2008) (E-published Oct. 2007).

Rippe, R., et al., "DNA-Mediated Gene Transfer into Adult Rat Hepatocytes in Primary Culture," Mol. Cell Biol., vol. 10, pp. 689-695 (Feb. 1990).

Rosel, J., et al., "Conserved TAAATG sequence a the transcriptional and translational initiation sites of vaccinia virus late genes deduced by structural and functional analysis of the HindIII H genome fragment," J Virology, vol. 60, No. 2, pp. 436-449 (Jul. 1986).

Rosenberg, S., et al., "Use of tumor-infiltrating lymphocytes and interleukin-2 in the immunotherapy of patients with metastatic melanoma. A preliminary report," N. Engl. J. Med., vol. 319., pp. 1676-1680 (Dec. 1988).

(56) References Cited

OTHER PUBLICATIONS

Rosenberg, S., et al., "Experience with the Use of High-Dose Interleukin-2 in the Treatment of 652 Cancer Patients," Ann. Surg., vol. 210, No. 4, pp. 474-548 (Apr. 17, 1989).

Schmitz, V., et al., "Gene therapy for liver diseases: recent strategies for treatment of viral hepatitis and liver malignancies," Gut, vol. 50, pp. 130-135 (Jan. 2002).

Seet, B., et al., "Molecular determinants for CC-chemokine recognition by a poxvirus CC-chemokine inhibitor," Proc Natl Acad Sci USA, vol. 98, No. 16, pp. 9008-9013, (Jul. 2001).

Serrano, M., et al., "A new regulatory motif in cell-cycle control causing specific inhibition of cyclin D/CDK4," Nature, vol. 366, pp. 704-707 (Dec. 1993).

Smith, G., et al., "Vaccinia virus immune evasion," Imnnunol Rev., vol. 159, pp. 137-154 (Oct. 1997).

Smith, G., et al., "Corticotropin releasing factor receptor 1-deficient mice display decreased anxiety, impaired stress response, and aberrant neuroendocrine development," Neuron., vol. 20, pp. 1093-1102 (Jun. 1998).

Smith, B., et al., "Prognostic Significance of Vascular Endothelial Growth Factor Protein Levels in Oral and Oropharyngeal Squamous Cell Carcinoma," Clinical Oncol., vol. 18, pp. 2046-2052 (May 2000).

Smith, G., "Vaccinia virus immune evasion," Imnnunol Lett., vol. 65, Issue 1-2, pp. 55-62 (Jan. 1999).

Smith, V., et al., "Ectromelia, vaccinia and cowpox viruses encode secreted interleukin-18-binding proteins," J. Gen. Virol., vol. 81, pp. 1223-1230 (May 2000).

Solyanik, G., et al., "Different growth patterns of a cancer cell population as a function of its starting growth characteristics: analysis by mathematical modelling," Cell. Prolif., vol. 28, No. 5, pp. 263-278 (Mar. 1995).

Sroller, V., et al., "Effect of IFN-gamma receptor gene deletion on vaccinia virus virulence," Arch. Virol., vol. 146, pp. 239-249 (Mar. 2001).

Stokke, T., et al., "Uncoupling of the order of the S and M phases: effects of staurosporine on human cell cycle kinases," Cell Prolif., vol. 30, No. 5, pp. 197-218 (Aug. 1997).

Symons, J., et al., "Vaccinia virus encodes a soluble type I interferon receptor of novel structure and broad species specificity," Cell, vol. 81, pp. 551-560 (May 19, 1995).

Thorne, S., et al., "The Use of Oncolytic Vaccinia Viruses in the Treatment of Cancer: A New Role for an Old Ally?," Current Gene Therapy, vol. 5, pp. 429-443 (Aug. 2005).

Tscharke, D., et al., "Dermal Infection with Vaccinia Virus Reveals Roles for Virus Proteins not seen using other Inoculation Routes," J. Gen. Virol., vol. 83, pp. 1977-1986 (Aug. 2002).

Tsujimoto, Y., et al., "Analysis of the structure, transcripts, and protein products of bcl-2, the gene involved in human follicular lymphoma," Proc. Natl. Acad. Sci., vol. 83, No. 14, pp. 5214-5218 (Jul. 1986).

Tsujimoto, Y., et al., "Involvement of the bcl-2 gene in human follicular lymphoma," Science, vol. 228, No. 4706, pp. 1440-1443 (Jun. 1985).

Tsujimoto, Y., et al., "Clustering of breakpoints on chromosome 11 in human B-cell neoplasms with the t(11;14) chromosome translocation," Nature, vol. 314, pp. 340-343 (May 1985).

Tsumaki, N., et al., "Modular Arrangement of Cartilage- and Neural Tissue-specific cis-Elements in the Mouse a2(XI) Collagen Promoter," J. Biol. Chem., vol. 273, No. 36, pp. 22861-22864 (Sep. 1998).

Upton, C., et al., "Myxoma Virus Expresses a Secreted Protein with Homology to the Tumor Necrosis Factor Receptor Gene Family That Contributes to Viral Virulence," Virology, vol. 184, No. 1, pp. 370-382 (Sep. 1991).

Vicari, A., et al., "Chemokines in cancer," Cytokine Growth Factor Rev., vol. 13, pp. 143-154 (Apr. 2002).

Vogelstein B., et al., "P53 Function and Dysfunction," Cell, vol. 70, No. 4, pp. 523-526 (Aug. 1992).

Wallach, D., et al., "Tumor Necrosis Factor Receptor and Fas Signaling Mechanisms," Annu. Rev. Immunol., vol. 17, pp. 331-367 (Apr. 1999).

Weijer, K., et al., "Feline Malignant Mammary Tumors. I. Morphology and Biology: Some Comparisons With Human and Canine Mammary Carcinomas," J Natl Cancer Inst, vol. 49, pp. 1697-1707 (Aug. 1972).

Wold, W., et al., "Adenovirus proteins that subvert host defenses," Trends Microbiol, vol. 2, No. 11, pp. 437-443, (Nov. 1994).

Wolffe, E., et al., "Deletion of the vaccinia virus B5R gene encoding a 42-kilodalton membrane glycoprotein inhibits extracellular virus envelope formation and dissemination," J. Virol., 67, pp. 4732-4741 (Aug. 1993).

Wong, T., et al., "Appearance of beta-lactamase activity in animal cells upon liposome-mediated gene transfer," Gene, vol. 10, pp. 87-94 (Jul. 1980).

Wu, H., et al., "Promoter-Dependent Tissue-Specific Expressive Nature of Imprinting Gene, Insulin-like Growth Factor II, in Human Tissues," Biochem. Biophys. Res. Commun., vol. 233, No. 1, pp. 221-226 (Feb. 1997).

Xu, et al., "Myxoma virus expresses a TNF receptor homolog with two distinct functions," Virus Genes, vol. 21, Nos. 1-2, pp. 97-109 (Aug. 2000).

Zhao-Emonet, J., et al., "Deletional and mutational analyses of the human CD4 gene promoter: characterization of a minimal tissue-specific promoter," Biochem. Biophys. Acta., vol. 1442, No. 2-3, pp. 109-119 (Jul. 28, 1998).

U.S. Appl. No. 13/535,291—Notice of Allowance dated Nov. 3, 2014.

U.S. Appl. No. 13/675,953—Notice of Allowance dated Nov. 13, 2014.

U.S. Appl. No. 13/675,953—Non-final office action dated Jul. 30, 2014.

U.S. Appl. No. 14/273,476—Final Office Action dated Nov. 21, 2014.

U.S. Appl. No. 14/273,476—Non-final office action dated Aug. 20, 2014.

\* cited by examiner

SYSTEMIC TREATMENT OF METASTATIC AND/OR SYSTEMICALLY-DISSEMINATED CANCERS USING GM-CSF-EXPRESSING POXVIRUSES

This application claims priority to U.S. Provisional Patent Application Ser. No. 60/714,679 filed Sep. 7, 2005, which is incorporated herein by reference in its entirety.

BACKGROUND OF THE INVENTION

I. Field of the Invention

The present invention relates generally to the fields of oncology and virology. More particularly, it concerns vaccinia viruses that express GM-CSF and their use in systemic administration to treat cancer.

II. Description of Related Art

Normal tissue homeostasis is a highly regulated process of cell proliferation and cell death. An imbalance of either cell proliferation or cell death can develop into a cancerous state (Solyanik et al., 1995; Stokke et al., 1997; Mumby and Walter, 1991; Natoli et al., 1998; Magi-Galluzzi et al., 1998). For example, cervical, kidney, lung, pancreatic, colorectal and brain cancer are just a few examples of the many cancers that can result (Erlandsson, 1998; Kolmel, 1998; Mangray and King, 1998; Gertig and Hunter, 1997; Mougin et al., 1998). In fact, the occurrence of cancer is so high that over 500,000 deaths per year are attributed to cancer in the United States alone.

The maintenance of cell proliferation and cell death is at least partially regulated by proto-oncogenes and tumor suppressors. A proto-oncogene or tumor suppressor can encode proteins that induce cellular proliferation (e.g., sis, erbB, src, ras and myc), proteins that inhibit cellular proliferation (e.g., Rb, p16, p19, p21, p53, NF1 and WT1) or proteins that regulate programmed cell death (e.g., bcl-2) (Ochi et al., 1998; Johnson and Hamdy, 1998; Liebermann et al., 1998). However, genetic rearrangements or mutations of these proto-oncogenes and tumor suppressors result in the conversion of a proto-oncogene into a potent cancer-causing oncogene or of a tumor suppressor into an inactive polypeptide. Often, a single point mutation is enough to achieve the transformation. For example, a point mutation in the p53 tumor suppressor protein results in the complete loss of wild-type p53 function (Vogelstein and Kinzler, 1992).

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. Surgery plays a central role in the diagnosis and treatment of cancer. Typically, a surgical approach is required for biopsy and to remove cancerous growth. However, if the cancer has metastasized and is widespread, surgery is unlikely to result in a cure and an alternate approach must be taken. Radiation therapy, chemotherapy, and immunotherapy are alternatives to surgical treatment of cancer (Mayer, 1998; Ohara, 1998; Ho et al., 1998). Radiation therapy involves a precise aiming of high energy radiation to destroy cancer cells and much like surgery, is mainly effective in the treatment of non-metastasized, localized cancer cells. Side effects of radiation therapy include skin irritation, difficulty swallowing, dry mouth, nausea, diarrhea, hair loss and loss of energy (Curran, 1998; Brizel, 1998).

Chemotherapy, the treatment of cancer with anti-cancer drugs, is another mode of cancer therapy. The effectiveness of a given anti-cancer drug therapy often is limited by the difficulty of achieving drug delivery throughout solid tumors (el-Kareh and Secomb, 1997). Chemotherapeutic strategies are based on tumor tissue growth, wherein the anti-cancer drug is targeted to the rapidly dividing cancer cells. Most chemotherapy approaches include the combination of more than one anti-cancer drug, which has proven to increase the response rate of a wide variety of cancers (U.S. Pat. Nos. 5,824,348; 5,633,016 and 5,798,339, incorporated herein by reference). A major side effect of chemotherapy drugs is that they also affect normal tissue cells, with the cells most likely to be affected being those that divide rapidly in some cases (e.g., bone marrow, gastrointestinal tract, reproductive system and hair follicles). Other toxic side effects of chemotherapy drugs can include sores in the mouth, difficulty swallowing, dry mouth, nausea, diarrhea, vomiting, fatigue, bleeding, hair loss and infection.

Immunotherapy, a rapidly evolving area in cancer research, is yet another option for the treatment of certain types of cancers. Theoretically, the immune system may be stimulated to identify tumor cells as being foreign and targets them for destruction. Unfortunately, the response typically is not sufficient to prevent most tumor growth. However, recently there has been a focus in the area of immunotherapy to develop methods that augment or supplement the natural defense mechanism of the immune system. Examples of immunotherapies currently under investigation or in use are immune adjuvants (e.g., *Mycobacterium bovis, Plasmodium falciparum*, dinitrochlorobenzene and aromatic compounds) (U.S. Pat. Nos. 5,801,005 and 5,739,169; Hui and Hashimoto, 1998; Christodoulides et al, 1998), cytokine therapy (e.g., interferons (IL-1, GM-CSF and TNF) (Bukowski et al., 1998; Davidson et al., 1998; Hellstrand et al., 1998), and gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Such methods, while showing some promise, have demonstrated limited success.

Replication-selective oncolytic viruses hold promise for the treatment of cancer (Kim et al., 2001). These viruses can cause tumor cell death through direct replication-dependent and/or viral gene expression-dependent oncolytic effects (Kim et al., 2001). In addition, viruses are able to enhance the induction of cell-mediated antitumoral immunity within the host (Todo et al., 2001; Sinkovics et al., 2000). These viruses also can be engineered to expressed therapeutic transgenes within the tumor to enhance antitumoral efficacy (Hermiston, 2000).

However, major limitations exist to this therapeutic approach. Although a degree of natural tumor-selectivity can be demonstrated for some virus species, new approaches are still needed to engineer and/or enhance tumor-selectivity for oncolytic viruses in order to maximize safety. This selectivity will become particularly important when intravenous administration is used, and when potentially toxic therapeutic genes are added to these viruses to enhance antitumoral potency; gene expression will need to be tightly limited in normal tissues. In addition, increased antitumoral potency through additional mechanisms such as induction of antitumoral immunity or targeting of the tumor-associated vasculature is highly desirable.

Therefore, more effective and less toxic therapies for the treatment of cancer are needed. The use of oncolytic viruses and immunotherapy present areas that can be developed, however, the limitations discussed above need to be overcome. Thus, the present invention addresses those limitations.

SUMMARY OF THE INVENTION

Thus, in accordance with the present invention there is provided a method of killing a cancer cell in a subject comprising administering to the subject an effective amount of a replicative vaccinia virus having an expression region with a promoter directing expression of a nucleic acid encoding granulocyte-macrophage colony stimulating factor (GM-CSF), wherein the administration is intravascular. It is specifically contemplated that the nucleic acid encodes human GM-CSF.

The vaccinia virus may be administered intravenously or intraarterially, for example, using intravenous drip or bolus, or using a pump. The vaccinia virus may be dispersed in a pharmaceutically acceptable formulation. The subject may be administered between about $10^5$, $10^6$ $10^7$, $10^8$ and about $10^9$, $10^{11}$, $10^{12}$, $10^{13}$ pfu of virus, or between about $10^7$ and about $10^{10}$ pfu of virus. The subject may be administered the vaccinia virus multiple times (1, 2, 3, 4, 5, 6, or more times), for example, wherein the second treatment occurs within 1, 2, 3, 4, 5, 6, 7 days or weeks of a first treatment, or wherein the second treatment occurs within 2 weeks of the first treatment. The same or a different dose may be administered. The cancer cell may be a metastasized cancer cell. The subject may have brain cancer, head & neck cancer, renal cancer, ovarian cancer, testicular cancer, uterine cancer, stomach cancer, lung cancer, colorectal cancer, breast cancer, prostate cancer, pancreatic cancer, hepatocellular cancer, leukemia, lymphoma, myeloma, or melanoma.

The vaccinia virus may have a deletion in its genome or a mutation in one or more genes. The thymidine kinase gene of the vaccinia virus may have been deleted. The vaccinia virus may have a mutation in a gene encoding (a) vaccinia virus growth factor; (b) a functional interferon-modulating polypeptide, wherein the interferon-modulating polypeptide directly binds interferon; (c) a complement control polypeptide, wherein the mutation results in the virus lacking at least one functional complement control polypeptide; (d) a TNF-modulating polypeptide, wherein the mutation results in the virus lacking at least one functional TNF-modulating polypeptide; (e) a serine protease inhibitor, wherein the mutation results in the virus lacking at least one functional serine protease inhibitor; (f) an IL-1β modulator polypeptide, wherein the mutation results in the virus lacking at least one functional IL-1β modulator polypeptide; (g) a functional A4 1 L, B7R, N1L or vCKBP chemokine binding polypeptide or C11R EGF-like polypeptide, wherein the mutation results in the virus lacking at least one function of A41L, B7R, N1L, vCKBP, or C11R; or (h) a polypeptide, wherein the mutation results in an increase in infectious EEV form of vaccinia virus. In addition, the vaccinia virus may comprise a mutation in a vaccinia virus growth factor. The vaccinia virus may be the Wyeth or Western Reserve (WR) strain. The promoter may be a vaccinia virus promoter, a synthetic promoter, a promoter that directs transcription during at least the early phase of infection, or a promoter that directs transcription during at least the late phase of infection.

In another embodiment, there is provided a method for treating cancer in a subject comprising administering to the subject an effective amount of a replicative vaccinia virus having an expression region with a promoter directing expression of a nucleic acid encoding granulocyte-macrophage colony stimulating factor (GM-CSF), wherein the administration is intravascular.

In yet another embodiment, there is provided a method for treating one or more metastases in a subject comprising administering to the subject an effective amount of a replicative vaccinia having an expression region with a promoter directing expression of a nucleic acid encoding granulocyte-macrophage colony stimulating factor (GM-CSF), wherein the administration is intravascular.

In other embodiments it is contemplated that methods involving a replication-competent vaccinia virus that is administered intravascularly may contain a nucleic acid encoding a protein or RNA other than GM-CSF. In particular embodiments, the nucleic acid encodes another cytokine. In certain embodiments, the nucleic acid encodes other immunostimulatory cytokines or chemokines, such as IL-12, IL-2 and others. In additional embodiments, the nucleic acid may encode thymidine deaminase or tumor necrosis factor (TNF), such as TNF-α. Moreover, it is contemplated that replicative vaccinia viruses may express more than one heterologous sequence. It may express, for example, GM-CSF protein and another protein or RNA molecule.

It is specifically contemplated that any embodiment discussed with respect to a particular method or composition may be implemented with respect to other methods and compositions of the invention.

The use of the word "a" or "an" when used in conjunction with the term "comprising" in the claims and/or the specification may mean "one," but it is also consistent with the meaning of "one or more," "at least one," and "one or more than one." Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Subsequent tumor volume in the liver was measured 7 weeks later by CT scan and (FIG. 2B) number of detectable tumor metastases in the lungs were counted following CT scan at weeks 6 and 7.

(FIG. 6A) Burst ratio of vaccinia strains in tumor to normal cells. Different vaccinia strains were used to infect both primary normal cells (NHBE) and a tumor cell line (A2780) at a Multiplicity of infection (MOI) of 1.0 Plaque Forming Unit (PFU)/cell. Virus collected 48 h later was titered by plaque assay and the ratio of virus produced (per cell) in tumor to normal cells is represented. (FIG. 6B) Cytopathic effect produced by viral infection. Western Reserve, Adenovirus serotype 5 and Adenovirus strain dl1520 (ONYX-015) (in some assays) were added to cell lines at ranges of MOIs (PFU/cell), and cell viability measured after 72 hours using MTS (Promega). The MOI of virus (PFU/cell) needed to reduce the cell viability to 50% of untreated control wells ($ED_{50}$) is plotted. (FIG. 6C) Systemic delivery of viral strains to tumors. 1×10⁹ PFU of vaccinia strain Western Reserve or Adenovirus serotype 5 were delivered intravenously to immunocompetent mice bearing subcutaneous CMT 64 or JC tumors. Mice were sacrificed after 48 or 72 hours and immunohistochemistry performed against viral coat proteins on paraffin embedded sections of tumor tissue. Graphs show scoring of positive cells in each tumour (*=none detectable). For each condition results are based on tumours from 3 mice, and for each tumour, ten randomly chosen fields of view were scored.

(FIG. 7A) Effects of overexpression of H-Ras on viral replication. NIH 3T3 cells, and NIH 3T3 cells expressing activated H-Ras, either proliferating or serum starved, were infected with different strains of vaccinia at an MOI of 1.0 PFU/cell. Viral strains were parental Western Reserve (WR), and WR containing deletions or insertions in either the Thymidine Kinase (TK) gene (vJS6), the viral growth factor (VGF) gene (vSC20), or containing deletions in both these genes (vvDD). Infectious virus was titered by plaque assay after 48 h. (FIG. 7B) Biodistribution of WR and vvDD following systemic delivery to tumor bearing mice. Athymic CD1 nu/nu mice bearing subcutaneous human HCT 116 tumors (arrowed) were treated with 1×10⁷ PFU of vaccinia strains via tail vein injection. Viral strains (WR and vvDD) expressed luciferase, and the subsequent biodistribution of viral gene expression was detected by bioluminescence imaging in an IVIS100 system (Xenogen Corp, Alameda) following addition of the substrate luciferin at the times indicated after treatment. (FIG. 7C) Viral gene expression, as quantified by light production, was plotted over time for the regions of interest covering the whole body (ventral image)(dashed line, open symbols), or from the tumor only (dorsal view)(solid line, filled symbols) for BALB/c mice bearing subcutaneous JC tumors (n=5 mice/group) and treated with 1×10⁷PFU of either virus by tail vein injection.

(FIG. 9A) Rabbits bearing VX2 tumors implanted into the liver were followed by CT imaging at times after tumor implantation. 1×10⁹ PFU of viruses vvDD and JX-963 were delivered by ear vein injection at 2, 3 and 4 weeks after tumor implantation (arrows), when tumors measured 5 cm³. The number of detectable lung metastases was also measured in these animals (representative CT images of primary liver tumors are shown at 8 weeks) (n=18 for control treated animals; n=6 for vvDD treated; n=6 for JX-963 treated). (FIG. 9B) CTL assay targeting VX2 tumor cells. CTL assay was performed by FACS analysis using pre-labeled VX2 cells mixed with 12.5×; 25× and 50× unlabelled peripheral blood lymphocytes from rabbits bearing VX2 tumors and treated with JX-963; from untreated animals with VX2 tumors; and from naive animals. Cell death was quantified by the ACTI assay (Cell Technology, Mountain View). (FIG. 9C) Four Rabbits treated as in (A) with JX-963 were re-treated with 1×10⁹ PFU of JX-963 at Day 42 after implantation (arrow), subsequent tumor volume was followed by CT scan.

(FIG. 10A) Different cell lines were infected with either Western Reserve or Adenovirus serotype 5 at an MOI of 1.0 PFU/cell. Amounts of virus produced (Infectious Units/cell) 48 h later were titered by plaque assay. (FIG. 10B) Mice treated as in FIG. 1C were sacrificed and tumor sections stained for viral coat proteins. Representative photographs show sections at 72 h and 10 days post-treatment.

(FIG. 13A) Single intravenous injections of 1×10⁹ PFU of viral strain vvDD or vaccinia Wyeth strain bearing a Thymidine Kinase deletion were delivered to immunocompetent mice bearing subcutaneous TIB 75 tumors (50-100 mm³). Tumor volume was measured by calipers, (n=8/group). (FIG. 13B) 1×10⁹ PFU of vvDD was delivered intratumorally (IT) or intraperitoneally (IP) to either SCID mice bearing subcutaneous HT29 tumors or C57B/6 mice bearing subcutaneous MC38 tumors and subsequent tumor volume compared to an uninfected control group (n=8/group).

DESCRIPTION OF ILLUSTRATIVE EMBODIMENTS

Figure 1:
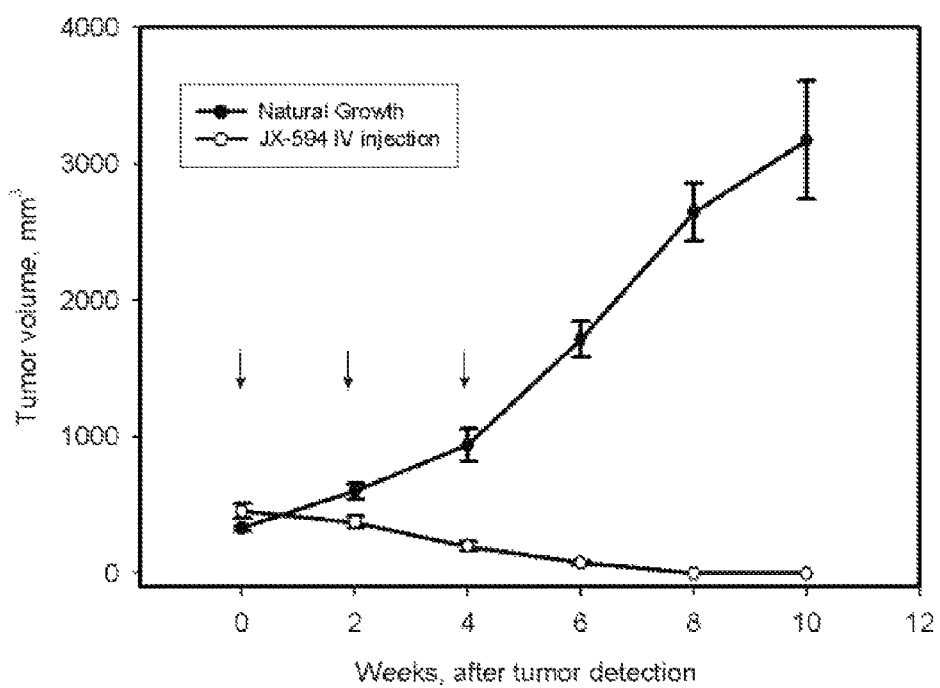
FIG. 1—JX-594 intravenous (IV) treatment of spontaneous rat hepatocellular carcinoma (HCC). Rats received the mutagen N-Nitrosomorpholine (NMM) in their drinking water (175 mg/L) for a period of 8 weeks and were then followed by ultrasound (US) until HCC tumors had formed and were 300-400 mm$^3$ (typically after 16-20 weeks). Animals then received 3 intravenous doses (one every two weeks, arrows) of either PBS (n=17) or 1×10$^8$ PFU of JX-594 virus (n=6). Subsequent tumor volumes were then calculated based on tumor measurements from US imaging.

GM-CSF-expressing poxviruses demonstrated efficacy and safety following intratumoral injection in animals and in patients with melanoma (Mastrangelo et al., 1999; 2000). Localized injection site and distant effects were seen, including tumor regressions and stabilizations (Mastrangelo et al., 1999). Efficacy was proposed to be due to induction of an immune response to the cancer cells in the mammal. U.S. Pat. Nos. 6,093,700 and 6,475,999 propose the use of poxviruses to deliver GM-CSF to tumors by intratumoral injection in humans in order to immunize in situ against melanoma, head and neck cancer, prostate cancer and bladder (Mastrangelo et al., 2002). These cancers were selected because of their superficial nature and access to direct intratumoral injection. These cancers are also reportedly sensitive to immunotherapy approaches that induce systemic tumor-specific, cytotoxic T-lymphocytes. GM-CSF was demonstrated to be a potent inducer of tumor-specific cytotoxic T-lymphocytes (CTLs) (Dranoff et al, 1993). Since viruses induce immune cell infiltration and proinflammatory cytokines, viruses may constitute an ideal method of delivering and expressing GM-CSF within a tumor mass.

The intratumoral route of injection has major limitations, however. This limits treatment to tumors that are accessible to safe intratumoral injection, usually superficial tumors, such as those listed above. In addition, efficacy against non-injected tumors requires induction of sufficiently potent tumor-specific, cytotoxic T-lymphocytes. These weaknesses limit the utility of this approach to cancers that are superficial and are able to induce sufficiently potent tumor-specific, cytotoxic T-lymphocytes systemically. Such tumors are rare. The only clear example of applicability to this approach is metastatic melanoma. Even in this tumor type however, distant responses were slow and were limited to superficial skin metastases. Organ-based or visceral tumors did not respond. Since these tumors are the cause of almost all cancer-related morbidity and deaths, systemic cytotoxic T-lymphocytes do not appear to be sufficient to induce lasting systemic, visceral responses or cures. Therefore, the vast majority of human tumors are not amenable to successful efficacy with this approach.

Intravascular administration (i.e., intravenous, intra-arterial) with delivery to metastatic tumors and immune tissues (e.g., reticuloendothelial cells) has numerous theoretical advantages. First, delivery of GM-CSF-expressing poxviruses to the majority of tumor sites, or all tumor sites, in the body of the mammal allows for systemic tumor destruction by both local intratumoral effects (due to poxvirus replication and GM-CSF effects locally within the infected tumors) and tumor-specific, cytotoxic T-lymphocytes induction and subsequent efficacy both at the infected tumor site and at a distance (in tumor sites that were not directly infected with the initial dosage). Delivery of virus to tumors through the bloodstream also allows for more uniform, widespread infection of cancer cells in the tumor. Therefore, the inventors now propose that multi-focal, disseminated, metastatic tumors can be effectively treated by intravascular poxviruses expressing GM-CSF. Many cancer types and/or stages that would not be amenable to the intratumoral approach would also be potentially treatable with the intravascular injection approach. Examples would include, but would not be limited to, lung, colorectal, breast, prostate, pancreatic, hepatocellular, leukemias, lymphomas, myelomas, and melanomas.

However, the safe and effective use of intravascular poxviruses expressing GM-CSF was viewed by the skilled artisan as being negatively impacted by potential problems. First, safety concerns were significant. After intravascular administration, numerous normal tissues would be exposed to poxvirus infection. Subsequent expression of a potent proinflammatory cytokine like GM-CSF would be predicted to potentially lead to significant inflammation in numerous organs such as liver, lung, kidney, heart, brain and others. In addition, systemic exposure to viremia can potentially induce sepsis and its associated complications (e.g., hypotension). Poxvirus infection in the brain of mice or humans, for example, can lead to clinically-significant, even fatal, encephalitis. GM-CSF expression could potentially significantly worsen this complication due to enhancement of inflammation.

Second, systemic induction of tumor-specific CTLs through GM-CSF expression was previously performed only through localized GM-CSF expression either through direct intratumoral injection (e.g., Vaccinia-GM-CSF, HSV-GM-CSF) or through ex vivo infection/transfection of autologous or allogeneic tumor cells to express GM-CSF (e.g., GVAX approach) followed by injection of GM-CSF cells into the skin.

Despite these potential drawbacks, the inventors now have demonstrated that two different GM-CSF-expressing poxviruses were well-tolerated intravenously and highly effective against disseminated tumors and metastases. In addition, a GM-CSF-expressing poxvirus had significantly better efficacy against both primary tumors and lung metastases than its non-GM-CSF-expressing control after intravenous administration. Also, this virus had significantly better efficacy against both primary tumors and lung metastases than a comparable virus (Wyeth vaccine strain) despite an additional deletion in the vgf gene not present in the other virus. Therefore, intravenous administration with a vaccinia expressing human GM-CSF resulted in significantly better efficacy over the same vaccinia without GM-CSF, and intravascular administration of a WR strain deletion mutant expressing human GM-CSF was significantly better than a standard vaccine strain expressing GM-CSF. These viruses were well-tolerated after intravenous administration to both tumor-bearing (rats and rabbits) and normal animals (rabbits). Treated animals did not lose weigh while tumor-bearing animals that did not receive treatment lost weight. Survival was increased following intravenous treatment. No significant organ toxicity was noted by blood testing or histopathology. The only reproducible histopathological findings were multiple sites of lymphoid hyperplasia that were noted following treatment (consistent with systemic immunostimulation). No significant toxicities were noted on histopathology. Therefore, these GM-CSF expressing poxviruses are well-tolerated at doses that were highly effective against systemic cancer.

I. Poxviruses

A. Vaccinia Virus

Vaccinia virus is a mystery to virology. It is not known whether vaccinia virus is the product of genetic recombination, if it is a species derived from cowpox virus or variola virus by prolonged serial passage, or if it is the living representative of a now extinct virus. Vaccinia virus was used for smallpox vaccination via inoculation into the superficial layers of the skin of the upper arm. However, with the eradication of smallpox, routine vaccination with vaccinia virus has ceased. Recent interest in vaccinia has focused on its possible usage as a vector for immunization against other viruses and gene therapy.

Vaccinia virus is a member of the family Poxviridae, the subfamily Chordopoxvirinae and the genus *Orthopoxvirus*. The virions contain RNA polymerase, early transcription factor, poly(A) polymerase, capping enzyme complex, RNA (nucleoside-2') methyltransferase, nucleoside triphosphate phosphohydrolase II, nick-joining enzyme, DNA topoisomerase and protein kinase. The genome is a double-stranded DNA of just over 180,000 base pairs characterized by a 10 kB inverted terminal repeat. The virus enters cells through pH-independent fusion with the plasma membrane or a low pH-dependent endosomal route.

B. Other Poxviruses

The genus *Orthopoxvirus* is relatively more homogeneous than other members of the Chordopoxvirinae subfamily and includes 11 distinct but closely related species, which includes vaccinia virus, variola virus (causative agent of smallpox), cowpox virus, buffalopox virus, monkeypox virus, mousepox virus and horsepox virus species as well as others (see Moss, 1996). Certain embodiments of the invention, as described herein, may be extended to other members of *Orthopoxvirus* genus as well as the *Parapoxvirus, Avipoxvirus, Capripoxvirus, Leporipoxvirus, Suipoxvirus, Molluscipoxvirus*, and *Yatapoxvirus* genus. A genus of poxvirus family is generally defined by serological means including neutralization and cross-reactivity in laboratory animals. Various members of the *Orthopoxvirus* genus, as well as other members of the Chordovirinae subfamily utilize immunomodulatory molecules, examples of which are provided herein, to counteract the immune responses of a host organism. Thus, the invention described herein is not limited to vaccinia virus, but may be applicable to a number of viruses.

II. Engineering of Poxviruses

Viruses are frequently inactivated, inhibited or cleared by immunomodulatory molecules such as interferons (-α, -β, -γ) and tumor necrosis factor-α (TNF) (Moss, 1996). Host tissues and inflammatory/immune cells frequently secrete these molecules in response to viral infection. These molecules can have direct antiviral effects and/or indirect effects through recruitment and/or activation of inflammatory cells and lymphocytes. Given the importance of these immunologic clearance mechanisms, viruses have evolved to express gene products that inhibit the induction and/or function of these cytokines/chemokines and interferons. For example, vaccinia virus (VV; and some other poxviruses) encodes the secreted protein vCKBP (B29R) that binds and inhibits the CC chemokines (e.g., RANTES, eotaxin, MIP-1-alpha) (Alcami et al., 1998). Some VV strains also express a secreted viral protein that binds and inactivates TNF (e.g., Lister A53R) (Alcami et al., 1999). Most poxvirus strains have genes encoding secreted proteins that bind and inhibit the function of interferons-α/β (e.g., B18R) or interferon-γ (B8R). vC12L is an IL-18-binding protein that prevents IL-18 from inducing IFN-γ and NK cell/cytotoxic T-cell activation.

Most poxvirus virulence research has been performed in mice. Many, but not all, of these proteins are active in mice (B18R, for example, is not). In situations in which these proteins are active against the mouse versions of the target cytokine, deletion of these genes leads to reduced virulence and increased safety with VV mutants with deletions of or functional mutations in these genes. In addition, the inflammatory/immune response to and viral clearance of these mutants is often increased compared to the parental virus strain that expresses the inhibitory protein. For example, deletion of the T1/35kDa family of poxvirus-secreted proteins (chemokine-binding/-inhibitory proteins) can lead to a marked increase in leukocyte infiltration into virus-infected tissues (Graham et al., 1997). Deletion of the vC12L gene in VV leads to reduced viral titers/toxicity following intranasal administration in mice; in addition, NK cell and cytotoxic T-lymphocyte activity is increased together with IFN-γ induction (Smith et al., 2000). Deletion of the Myxoma virus T7 gene (able to bind IFN-γ and a broad range of chemokines) results in reduced virulence and significantly increased tissue inflammation/infiltration in a toxicity model (Upton et al., 1992; Mossman et al., 1996). Deletion of the M-T2 gene from myxoma virus also resulted in reduced virulence in a rabbit model (Upton et al. 1991). Deletion of the B18R anti-interferon-α/-β gene product also leads to enhanced viral sensitivity to IFN-mediated clearance, reduced titers in normal tissues and reduced virulence (Symons et al., 1995; Colamonici et al., 1995; Alcami et al., 2000). In summary, these viral gene products function to decrease the antiviral immune response and inflammatory cell infiltration into virus-infected tissues. Loss of protein function through deletion/mutation leads to decreased virulence and/or increased proinflammatory properties of the virus within host tissues. See PCT/US2003/025 141, which is hereby incorporated by reference.

Cytokines and chemokines can have potent antitumoral effects (Vicari et al., 2002; Homey et al., 2002). These effects can be on tumor cells themselves directly (e.g., TNF) or they can be indirect through effects on non-cancerous cells. An example of the latter is TNF, which can have antitumoral effects by causing toxicity to tumor-associated blood vessels; this leads to a loss of blood flow to the tumor followed by tumor necrosis. In addition, chemokines can act to recruit (and in some cases activate) immune effector cells such as neutrophils, eosinophils, macrophages and/or lymphocytes. These immune effector cells can cause tumor destruction by a number of mechanisms. These mechanisms include the expression of antitumoral cytokines (e.g., TNF), expression of fas-ligand, expression of perforin and granzyme, recruitment of natural killer cells, etc. The inflammatory response can eventually lead to the induction of systemic tumor-specific immunity. Finally, many of these cytokines (e.g., TNF) or chemokines can act synergistically with chemotherapy or radiation therapy to destroy tumors.

Clinically effective systemic administration of recombinant versions of these immunostimulatory proteins is not feasible due to (1) induction of severe toxicity with systemic administration and (2) local expression within tumor tissue is needed to stimulate local infiltration and antitumoral effects. Approaches are needed to achieve high local concentrations of these molecules within tumor masses while minimizing levels in the systemic circulation. Viruses can be engineered to express cytokine or chemokine genes in an attempt to enhance their efficacy. Expression of these genes from replication-selective vectors has potential advantages over expression from non-replicating vectors. Expression from replicating viruses can result in higher local concentrations within tumor masses; in addition, replicating viruses can help to induce antitumoral immunity through tumor cell destruction/oncolysis and release of tumor antigens in a proinflammatory environment. However, there are several limitations to this approach. Serious safety concerns arise from the potential for release into the environment of a replication-competent virus (albeit tumor-selective) with a gene that can be toxic if expressed in high local concentrations. Viruses that express potent pro-inflammatory genes from their genome may therefore pose safety risks to the treated patient and to the general public. Even with tumor-targeting, replication-selective viruses expressing these genes, gene expression can occur in normal tissues resulting in toxicity. In addition, size limitations prevent expression of multiple and/or large genes from viruses such as adenovirus; these molecules will definitely act more efficaciously in combination. Finally, many of the oncolytic viruses in use express anti-inflammatory proteins and therefore these viruses will counteract the induction of a proinflammatory milieu within the infected tumor mass. The result will be to inhibit induction of antitumoral immunity, antivascular effects and chemotherapy-/radiotherapy-sensitization.

A. Vaccinia Virus Products

1. Interferon-Modulating Polypeptides

Interferon-α/-β blocks viral replication through several mechanisms. Interferon-γ has weaker direct viral inhibitory effects but is a potent inducer of cell-mediated immunity through several mechanisms. Viruses have evolved to express secreted gene products that are able to counteract the antiviral effects of interferons. For example, vaccinia virus (and other poxviruses) encodes the secreted proteins B8R and B 18R which bind interferon-γ and -α/-β, respectively (Smith et al., 1997; Symons et al, 1995; Alcami et al., 2000). An additional example of a vaccinia gene product that reduces interferon induction is the caspase-1 inhibitor B13R which inhibits activation of the interferon-γ-inducing factor IL-18. Interferon modulating polypeptides include, but are not limited to, B 18R, which may be termed B 19R in other viral strains, such as the Copenhagen strain of Vaccinia virus; B8R; B13R; vC12L; A53R; E3L and other viral polypeptides with similar activities or properties. IFN modulating polypeptides may be divided into the non-exclusive categories of those that preferentially modulate IFNα and/or β pathways (such as B18R, B8R, B13R, or vC12L) and those that modulate IFNγ pathways(for example B8R, B13R, or vC12L).

Cancer cells are frequently resistant to the effects of interferons. A number of mechanisms are involved. These include the fact that ras signal transduction pathway activation (e.g., by ras mutation, upstream growth factor receptor overexpression/mutation, etc.), a common feature of cancer cells, leads to PKR inhibition. In addition, lymphocytes are often inhibited in tumor masses by a variety of mechanisms including IL-10 production and fas-L expression by tumor cells. Since lymphocytes are a major source of interferon-γ production, lymphocyte inhibition leads to a decrease in interferon-γ production in tumors. Therefore, tumor masses tend to be sanctuaries from the effects of interferons. In addition, interferons themselves can have antitumoral effects. For example, IFN-γ can increase MHC class-I-associated antigen presentation; this will allow more efficient CTL-mediated killing of tumor cells. IFN-α/β, for example, can block angiogenesis within tumor masses and thereby block tumor growth.

2. Complement Control Polypeptides

A major mechanism for the clearance of viral pathogens is the killing of infected cells within the host or of virions within an organism by complement-dependent mechanisms. As the infected cell dies it is unable to continue to produce infectious virus. In addition, during apoptosis intracellular enzymes are released which degrade DNA. These enzymes can lead to viral DNA degradation and virus inactivation. Apoptosis can be induced by numerous mechanisms including the binding of activated complement and the complement membrane attack complex. Poxviruses such as vaccinia have evolved to express gene products that are able to counteract the complement-mediated clearance of virus and/or virus-infected cells. These genes thereby prevent apoptosis and inhibit viral clearance by complement-dependent mechanisms, thus allowing the viral infection to proceed and viral virulence to be increased. For example, vaccinia virus complement control proteins (VCP; e.g., C21L) have roles in the prevention of complement-mediated cell killing and/or virus inactivation (Isaacs et al., 1992). VCP also has anti-inflammatory effects since its expression decreases leukocyte infiltration into virally-infected tissues. Complement control polypeptides include, but are not limited to, VCP, also known as C3L or C21L.

Cancer cells frequently overexpress cellular anti-complement proteins; this allows cancer cells to survive complement attack ±tumor-specific antibodies (Caragine et al., 2002; Durrant et al., 2001; Andoh et al 2002). Therefore, agents that preferentially target tumor cells due to their inherent resistance to complement-mediated killing would have selectivity and potential efficacy in a wide range of human cancers (Durrant et al., 2001). In addition, one of the hallmarks of cancer cells is a loss of normal apoptotic mechanisms (Gross et al., 1999). Resistance to apoptosis promotes carcinogenesis as well as resistance to antitumoral agents including immunologic, chemotherapeutic and radiotherapeutic agents (Eliopoulos et al., 1995). Apoptosis inhibition can be mediated by a loss of pro-apoptotic molecule function (e.g., bax), an increase in the levels/function of anti-apoptotic molecules (e.g., bcl-2) and finally a loss of complement sensitivity.

3. TNF-Modulating Polypeptides One of the various mechanisms for the clearance of viral pathogens is the killing of infected cells within the host by the induction of apoptosis, as described above. Apoptosis can be induced by numerous mechanisms including the binding of TNF and lymphotoxin-alpha (LTd) to cellular TNF receptors, which triggers intracellular signaling cascades. Activation of the TNF receptors function in the regulation of immune and inflammatory responses, as well as inducing apoptotic cell death (Wallach et al., 1999)

Various strains of poxviruses, including some vaccinia virus strains, have evolved to express gene products that are able to counteract the TNF-mediated clearance of virus and/or virus-infected cells. The proteins encoded by these genes circumvent the proinflammatory and apoptosis inducing activities of TNF by binding and sequestering extracellular TNF, resulting in the inhibition of viral clearance. Because viruses are not cleared, the viral infection is allowed to proceed, and thus, viral virulence is increased. Various members of the poxvirus family express secreted viral TNF receptors (vTNFR). For example, several poxviruses encode vTNFRs, such as myxoma (T2 protein), cowpox and vaccinia virus strains, such as Lister, may encode one or more of the CrmB, CrmC (A53R), CrmD, CrmE, B28R proteins and/or equivalents thereof. These vTNFRs have roles in the prevention of TNF-mediated cell killing and/or virus inactivation (Saraiva and Alcami, 2001). TNF modulatory polypeptides include, but are not limited to, A53R, B28R (this protein is present, but may be inactive in the Copenhagen strain of vaccinia virus) and other polypeptides with similar activities or properties.

One of the hallmarks of cancer cells is aberrant gene expression, which may lead to a loss of sensitivity to a number of molecular mechanisms for growth modulation, such as sensitivity to the anti-cancer activities of TNF. Thus, viral immunomodulatory mechanisms may not be required for the propagation of a virus within the tumor microenvironment.

4. Serine Protease Inhibitors

A major mechanism for the clearance of viral pathogens is the induction of apoptosis in infected cells within the host. As the infected cell dies it is unable to continue to produce infectious virus. In addition, during apoptosis intracellular enzymes are released which degrade DNA. These enzymes can lead to viral DNA degradation and virus inactivation. Apoptosis can be induced by numerous mechanisms including the binding of cytokines (e.g., tumor necrosis factor), granzyme production by cytotoxic T-lymphocytes or fas-ligand binding; caspase activation is a critical part of the final common apoptosis pathway. Viruses have evolved to express gene products that are able to counteract the intracellular signaling cascade induced by such molecules including fas-ligand or tumor necrosis factor (TNF)/TNF-related molecules (e.g., E3 10.4/14.5, 14.7 genes of adenovirus (Wold et al., 1994); ELB-19kD of adenovirus (Boyd et al., 1994); crmA from cowpox virus; B13R from vaccinia virus) (Dobbelstein et al., 1996; Kettle et al., 1997). These gene products prevent apoptosis by apoptosis-inducing molecules and thus allow viral replication to proceed despite the presence of antiviral apoptosis-inducing cytokines, fas, granzyme or other stimulators of apoptosis.

VV SPI-2/B13R is highly homologous to cowpox CrmA; SPI-1 (VV) is weakly homologous to CrmA (Dobbelstein et al., 1996). These proteins are serpins (serine protease inhibitors) and both CrmA and SPI-2 have roles in the prevention of various forms of apoptosis. Inhibition of interleukin-1β-converting enzyme (ICE) and granzyme, for example, can prevent apoptosis of the infected cell. These gene products also have anti-inflammatory effects. They are able to inhibit the activation of IL-18 which in turn would decrease IL-18-mediated induction of IFN-γ. The immunostimulatory effects of IFN-γ on cell-mediated immunity are thereby inhibited (Kettle et al., 1997). SPIs include, but are not limited to, B13R, B22R, and other polypeptides with similar activities or properties.

One of the hallmarks of cancer cells is a loss of normal apoptotic mechanisms (Gross et al., 1999). Resistance to apoptosis promotes carcinogenesis as well as resistance to antitumoral agents including immunologic, chemotherapeutic and radiotherapeutic agents (Eliopoulos et al., 1995). Apoptosis inhibition can be mediated by a loss of pro-apoptotic molecule function (e.g., bax) or an increase in the levels/function of anti-apoptotic molecules (e.g., bcl-2).

5. IL-1β—Modulating Polypeptides

IL-1β is a biologically active factors that acts locally and also systemically. Only a few functional differences between IL-1β and IL-1α have been described. The numerous biological activities of IL-1β is exemplified by the many different acronyms under which IL-1 has been described. IL-1 does not show species specificity with the exception of human IL-1β that is inactive in porcine cells. Some of the biological activities of IL-1 are mediated indirectly by the induction of the synthesis of other mediators including ACTH (Corticotropin), PGE2 (prostaglandin E2), PF4 (platelet factor-4), CSF (colony stimulating factors ), IL-6, and IL-8. The synthesis of IL-1 may be induced by other cytokines including TNF-α, IFN-α, IFN-β and IFN-γ and also by bacterial endotoxins, viruses, mitogens, and antigens. The main biological activity of IL-1 is the stimulation of T-helper cells, which are induced to secrete IL-2 and to express IL-2 receptors. Virus-infected macrophages produce large amounts of an IL-1 inhibitor that may support opportunistic infections and transformation of cells in patients with T-cell maturation defects. IL-1 acts directly on B-cells, promoting their proliferation and the synthesis of immunoglobulins. IL-1 also functions as one of the priming factors that makes B-cells responsive to IL-5. IL-1 stimulates the proliferation and activation of NK-cells and fibroblasts, thymocytes, glioblastoma cells.

Blockade of the synthesis of IL-1β by the viral protein is regarded as a viral strategy allowing systemic antiviral reactions elicited by IL-1 to be suppressed or diminished. Binding proteins effectively blocking the functions of IL-1 with similar activity as B15R have been found also to be encoded by genes of the cowpox virus. Vaccinia virus also encodes another protein, designated B8R, which behaves like a receptor for cytokines (Alcami and Smith, 1992; Spriggs et al., 1992). IL-1 modulating polypeptides include, but are not limited to, B13R, B15R, and other polypeptides with similar activities or properties.

One of the hallmarks of cancer cells is aberrant gene expression, which may lead to a loss of sensitivity to a number of molecular mechanisms for growth modulation, such as sensitivity to the anti-cancer activities of IL-1. Thus, viral immunomodulatory mechanisms may not be required for the propagation of a virus within the tumor microenvironment.

6. EEV Form

Viral spread to metastatic tumor sites, and even spread within an infected solid tumor mass, is generally inefficient (Heise et al., 1999). Intravenous administration typically results in viral clearance or inactivation by antibodies (e.g., adenovirus) (Kay et al., 1997) and/or the complement system (e.g., HSV) (Ikeda et al., 1999). In addition to these immune-mediated mechanisms, the biodistribution of these viruses results in the vast majority of intravenous virus depositing within normal tissues rather than in tumor masses. Intravenous adenovirus, for example, primarily ends up within the liver and spleen; less than 0.1% of the input virus depositing within tumors, even in immunodeficient mice (Heise et al., 1999). Therefore, although some modest antitumoral efficacy can be demonstrated with extremely high relative doses in immunodeficient mouse tumor models, intravenous delivery is extremely inefficient and significantly limits efficacy.

Vaccinia virus has the ability to replicate within solid tumors and cause necrosis. In addition, thymidine kinase-deletion mutants can infect tumor masses and ovarian tissue and express marker genes preferentially in mouse tumor model systems (Gnant et al., 1999). However, since these studies generally determined tumor targeting based on marker gene expression after ≥5 days, it is unclear whether the virus preferentially deposits in, expresses genes in or replicates in tumor/ovary tissue (Puhlmann et al., 2000). Regardless of the mechanism, the antitumoral efficacy of this virus without additional transgenes was not statistically significant (Gnant et al., 1999). In contrast, intratumoral virus injection had significant antitumoral efficacy (McCart et al. 2000). Therefore, i.v. efficacy could be improved if i.v. delivery to the tumor were to be improved.

Vaccinia virus replicates in cells and produces both intracellular virus (IMV, intracellular mature virus; IEV, intracellular enveloped virus) and extracellular virus (EEV, extracellular enveloped virus; CEV, cell-associated extracellular virus) (Smith et al., 1998). IMV represents approximately 99% of virus yield following replication by wild-type vaccinia virus strains. This virus form is relatively stable in the environment, and therefore it is primarily responsible for spread between individuals; in contrast, this virus does not spread efficiently within the infected host due to inefficient release from cells and sensitivity to complement and/or antibody neutralization. In contrast, EEV is released into the extracellular milieu and typically represents only approximately 1% of the viral yield (Smith et al., 1998). EEV is responsible for viral spread within the infected host and is relatively easily degraded outside of the host. Importantly, EEV has developed several mechanisms to inhibit its neutralization within the bloodstream. First, EEV is relatively resistant to complement (Vanderplasschen et al., 1998); this feature is due to the incorporation of host cell inhibitors of complement into its outer membrane coat plus secretion of Vaccinia virus complement control protein (VCP) into local extracellular environment. Second, EEV is relatively resistant to neutralizing antibody effects compared to IMV (Smith et al., 1997). EEV is also released at earlier time points following infection (e.g., 4-6 hours) than is IMV (which is only released during/after cell death), and therefore spread of the EEV form is faster (Blasco et al., 1993).

Unfortunately, however, wild-type vaccinia strains make only very small amounts of EEV, relatively. In addition, treatment with vaccinia virus (i.e., the input dose of virus) has been limited to intracellular virus forms to date. Standard vaccinia virus (VV) manufacturing and purification procedures lead to EEV inactivation (Smith et al., 1998), and non-human cell lines are frequently used to manufacture the virus; EEV from non-human cells will not be protected from complement-mediated clearance (complement inhibitory proteins acquired from the cell by EEV have species restricted effects). Vaccinia virus efficacy has therefore been limited by the relative sensitivity of the IMV form to neutralization and by its inefficient spread within solid tumor masses; this spread is typically from cell to adjacent cell. IMV spread to distant tumor masses, either through the bloodstream or lymphatics, is also inefficient.

Therefore, the rare EEV form of vaccinia virus has naturally acquired features that make it superior to the vaccinia virus form used in patients to date (IMV); EEV is optimized for rapid and efficient spread through solid tumors locally and to regional or distant tumor sites. Since EEV is relatively resistant to complement effects, when it is grown in a cell type from the same species, this virus form will have enhanced stability and retain activity longer in the blood following intravascular administration than standard preparations of vaccinia virus (which contain exclusively IMV) (Smith et al., 1998). Since EEV is resistant to antibody-mediated neutralization, this virus form will retain activity longer in the blood following intravascular administration than standard preparations of vaccinia virus (which contain almost exclusively IMV) (Vanderplasschen et al., 1998). This feature will be particularly important for repeat administration once neutralizing antibody levels have increased; all approved anti-cancer therapies require repeat administration. Therefore, the EEV form of vaccinia, and other poxviruses, will result in superior delivery of therapeutic viruses and their genetic payload to tumors through the bloodstream. This will lead to enhanced systemic efficacy compared with standard poxvirus preparations. Finally, the risk of transmission to individuals in the general public should be reduced significantly since EEV is extremely unstable outside of the body. Polypeptides involved in the modulation of the EEV form of a virus include, but are not limited to, A34R, B5R, and various other proteins that influence the production of the EEV form of the poxviruses. A mutation at codon 151 of A34R from a lysine to a aspartic acid (K151D mutation) renders the A34R protein less able to tether the EEV form to the cell membrane. B5R is an EEV-membrane bound polypeptide that may bind complement. The total deletion of A43R may lead to increased EEV release, but markedly reduced infectivity of the viruses, while the K151D mutation increases EEV release while maintaining infectivity of the released viruses. B5R has sequence homology to VCP (anti-complement), but complement inhibition has not yet been proven.

Briefly, one method for identifying a fortified EEV form is as follows. EEV are diluted in ice-cold MEM and mixed (1:1 volume) with active or heat-inactivated (56° C., 30 min, control) serum diluted in ice-cold MEM (final dilution of serum 1/10, 1/20, or 1/30). After incubation or 75 minutes at 7° C., samples are cooled on ice and mAb 5B4/2F2 is added to fresh EEV samples to neutralize any contaminates (IMV and ruptured EEV). Virions are then bound to RK13 cells for one hour on ice, complement and unbound virions are washed away, and the number of plaques are counted two days later. The higher the plaque number the greater the resistance to complement. Vanderplasschen et al. (1998), herein incorporated by reference. Exemplary methods describing the isolation of EEV forms of Vaccinia virus can be found in Blasco et al. (1992) (incorporated herein by reference).

7. Other Polypeptides

Other viral immunomodulatory polypeptides may include polypeptides that bind other mediators of the immune response and/or modulate molecular pathways associated with the immune response. For example, chemokine binding polypeptides such as B29R (this protein is present, but may be inactive in the Copenhagen strain of Vaccinia virus), C23L, vCKBP, A41L and polypeptides with similar activities or properties. Other vaccinia virus proteins such as the vaccinia virus growth factor (e.g., C11L), which is a viral EGF-like growth factor, may also be the target for alteration in some embodiments of the invention. Other polypeptides that may be classified as viral immunomodulatory factors include, but are not limited to B7R, N1L, or other polypeptides that whose activities or properties increase the virulence of a poxvirus.

8. Vaccinia Virus-Induced Cell Fusion

In certain embodiments of the invention an alteration, deletion, or mutation of A56R or K2L encoding nucleic genes may lead to cell-cell fusion or syncitia formation induced by VV infection. Vaccinia virus-induced cell fusion will typically increase antitumoral efficacy of VV due to intratumoral viral spread. Intratumoral viral spreading by cell fusion will typically allow the virus to avoid neutralizing antibodies and immune responses. Killing and infection of adjacent uninfected cells (i.e., a "bystander" effect) may be more efficient in VV with mutations in one or both of these genes, which may result in improved local antitumoral effects.

B. Virus Propagation

Vaccinia virus may be propagated using the methods described by Earl and Moss in Ausbel et al., Current Protocols in Molecular Biology, pages 16.15.1 to 16.18.10, which is incorporated by reference herein.

III. Proteinaceous and Nucleic Acid Compositions

The present invention concerns poxviruses that are advantageous in the study and treatment of cancer cells and cancer in a patient. It concerns vaccinia viruses, optionally constructed with one or more mutations compared to wild-type such that the virus has desirable properties for use against cancer cells, while being less toxic or non-toxic to non-cancer cells. Such poxviruses are described in PCT/US2003/025141, which is incorporated herein by reference. The teachings described below provide various protocols, by way of example, of implementing methods and compositions of the invention. They provide background for generating mutated viruses through the use of recombinant DNA technology.

A. Proteinaceous Compositions

In certain embodiments, the present invention concerns generating vaccinia virus, optionally those that lack one or more functional polypeptides or proteins and/or generating poxviruses that have the ability to release more of a particular form of the virus, such as an infectious EEV form. In other embodiments, the present invention concerns poxviruses and their use in combination with proteinaceous composition as part of a pharmaceutically acceptable formulation.

As used herein, a "protein" or "polypeptide" refers to a molecule comprising at least one amino acid residue. In some embodiments, a wild-type version of a protein or polypeptide are employed, however, in many embodiments of the invention, a viral protein or polypeptide is absent or altered so as to render the virus more useful for the treatment of a cancer cells or cancer in a patient. The terms described above may be used interchangeably herein. A "modified protein" or "modified polypeptide" refers to a protein or polypeptide whose chemical structure is altered with respect to the wild-type protein or polypeptide. In some embodiments, a modified protein or polypeptide has at least one modified activity or function (recognizing that proteins or polypeptides may have multiple activities or functions). The modified activity or function may we reduced, diminished, eliminated, enhanced, improved, or altered in some other way (such as specificity) with respect to that activity or function in a wild-type protein or polypeptide. It is specifically contemplated that a modified protein or polypeptide may be altered with respect to one activity or function yet retain wild-type activity or function in other respects. Alternatively, a modified protein may be completely nonfunctional or its cognate nucleic acid sequence may have been altered so that the polypeptide is no longer expressed at all, is truncated, or expresses a different amino acid sequence as a result of a frameshift.

In certain embodiments the size of a mutated protein or polypeptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. It is contemplated that polypeptides may be mutated by truncation, rendering them shorter than their corresponding wild-type form.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's GenBank and GenPept databases (www.ncbi.nlm.nih.gov). The coding regions for these known genes may be amplified and/or expressed using the techniques disclosed herein or as would be know to those of ordinary skill in the art.

1. Functional Aspects

When the present application refers to the function or activity of viral proteins or polypeptides, it is meant to refer to the activity or function of that viral protein or polypeptide under physiological conditions, unless otherwise specified. For example, an interferon-modulating polypeptide refers to a polypeptide that affects at least one interferon and its activity, either directly or indirectly. The polypeptide may induce, enhance, raise, increase, diminish, weaken, reduce, inhibit, or mask the activity of an interferon, directly or indirectly. An example of directly affecting interferon involves, in some embodiments, an interferon-modulating polypeptide that specifically binds to the interferon. Determination of which molecules possess this activity may be achieved using assays familiar to those of skill in the art. For example, transfer of genes encoding products that modulate interferon, or variants thereof, into cells that are induced for interferon activity compared to cells with such transfer of genes may identify, by virtue of different levels of an interferon response, those molecules having a interferon-modulating function.

It is specifically contemplated that a modulator may be a molecule that affects the expression proteinaceous compositions involved in the targeted molecule's pathway, such as by binding an interferon-encoding transcript. Determination of which molecules are suitable modulators of interferon, IL-1β, TNF, or other molecules of therapeutic benefit may be achieved using assays familiar to those of skill in the art-some of which are disclosed herein-and may include, for example, the use of native and/or recombinant viral proteins.

2. Variants of Viral Polypeptides

Amino acid sequence variants of the polypeptides of the present invention can be substitutional, insertional or deletion variants. A mutation in a gene encoding a viral polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids of the polypeptide, as compared to wild-type. Various polypeptides encoded by Vaccinia Virus may be identified by reference to Rosel et al. (1986), Goebel et al. (1990) and GenBank Accession Number NC_001559, each of which is incorporated herein by reference.

Deletion variants lack one or more residues of the native or wild-type protein. Individual residues can be deleted or all or part of a domain (such as a catalytic or binding domain) can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of an immunoreactive epitope or simply one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

The term "functionally equivalent codon" is used herein to refer to codons that encode the same amino acid, such as the six codons for arginine or serine, and also refers to codons that encode biologically equivalent amino acids (see Table 1, below).

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

TABLE 1

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |

TABLE 1-continued

Codon Table

| Amino Acids | | | Codons |
|---|---|---|---|
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2) glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

IV. Nucleic Acid Molecules

A. Polynucleotides Encoding Native Proteins or Modified Proteins

The present invention concerns polynucleotides, isolatable from cells, that are capable of expressing all or part of a protein or polypeptide. In some embodiments of the invention, it concerns a viral genome that has been specifically mutated to generate a virus that lacks certain functional viral polypeptides. The polynucleotides may encode a peptide or polypeptide containing all or part of a viral amino acid sequence or they be engineered so they do not encode such a viral polypeptide or encode a viral polypeptide having at least one function or activity reduced, diminished, or absent. Recombinant proteins can be purified from expressing cells to yield active proteins. The genome, as well as the definition of the coding regions of vaccinia virus may be found in Rosel et al. (1986), Goebel et al. (1990) and/or GenBank Accession Number NC_00159, each of which is incorporated herein by reference.

As used herein, the term "DNA segment" refers to a DNA molecule that has been isolated free of total genomic DNA of a particular species. Therefore, a DNA segment encoding a polypeptide refers to a DNA segment that contains wild-type, polymorphic, or mutant polypeptide-coding sequences yet is isolated away from, or purified free from, total mammalian or human genomic DNA. Included within the term "DNA segment" are a polypeptide or polypeptides, DNA segments smaller than a polypeptide, and recombinant vectors, including, for example, plasmids, cosmids, phage, viruses, and the like.

As used in this application, the term "poxvirus polynucleotide" refers to a nucleic acid molecule encoding a poxvirus polypeptide that has been isolated free of total genomic nucleic acid. Similarly, a "vaccinia virus polynucleotide" refers to a nucleic acid molecule encoding a vaccinia virus polypeptide that has been isolated free of total genomic nucleic acid. A "poxvirus genome" or a "vaccinia virus genome" refers to a nucleic acid molecule that can be provided to a host cell to yield a viral particle, in the presence or absence of a helper virus. The genome may or may have not been recombinantly mutated as compared to wild-type virus.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular polypeptide from a given species may be represented by natural variants that have slightly different nucleic acid sequences but, nonetheless, encode the same protein (see Table 1 above).

Similarly, a polynucleotide comprising an isolated or purified wild-type or mutant polypeptide gene refers to a DNA segment including wild-type or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit (including any sequences required for proper transcription, post-translational modification, or localization). As will be understood by those in the art, this functional term includes genomic sequences, cDNA sequences, and smaller engineered gene segments that express, or may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs.

In particular embodiments, the invention concerns isolated DNA segments and recombinant vectors incorporating DNA sequences that encode a wild-type or mutant poxvirus polypeptide or peptide that includes within its amino acid sequence a contiguous amino acid sequence in accordance with, or essentially corresponding to a native polypeptide. Thus, an isolated DNA segment or vector containing a DNA segment may encode, for example, a TNF modulator or TNF-modulating polypeptide that can inhibit or reduce TNF activity. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated DNA segments and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length polypeptide from any source or encode a truncated version of the polypeptide, for example a truncated vaccinia virus polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to the a particular gene, such as the B18R gene. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100, 000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass biologically functional equivalent modified polypeptides and peptides, for example, a modified gelonin toxin. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

In certain other embodiments, the invention concerns isolated DNA segments and recombinant vectors that include within their sequence a contiguous nucleic acid sequence from that shown in sequences identified herein (and/or incorporated by reference). Such sequences, however, may be mutated to yield a protein product whose activity is altered with respect to wild-type.

It also will be understood that this invention is not limited to the particular nucleic acid and amino acid sequences of these identified sequences. Recombinant vectors and isolated DNA segments may therefore variously include the poxvirus-coding regions themselves, coding regions bearing selected alterations or modifications in the basic coding region, or they may encode larger polypeptides that nevertheless include poxvirus-coding regions or may encode biologically functional equivalent proteins or peptides that have variant amino acids sequences.

The DNA segments of the present invention encompass biologically functional equivalent poxvirus proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

B. Mutagenesis of Poxvirus Polynucleotides

In various embodiments, the poxvirus polynucleotide may be altered or mutagenized. Alterations or mutations may include insertions, deletions, point mutations, inversions, and the like and may result in the modulation, activation and/or inactivation of certain pathways or molecular mechanisms, as well as altering the function, location, or expression of a gene product, in particular rendering a gene product non-functional. Where employed, mutagenesis of a polynucleotide encoding all or part of a Poxvirus may be accomplished by a variety of standard, mutagenic procedures (Sambrook et al., 1989). Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations may be induced following exposure to chemical or physical mutagens. Such mutation-inducing agents include ionizing radiation, ultraviolet light and a diverse array of chemical such as alkylating agents and polycyclic aromatic hydrocarbons all of which are capable of interacting either directly or indirectly (generally following some metabolic biotransformations) with nucleic acids. The DNA damage induced by such agents may lead to modifications of base sequence when the affected DNA is replicated or repaired and thus to a mutation. Mutation also can be site-directed through the use of particular targeting methods.

1. Random Mutagenesis a. Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations. Insertion mutagenesis has been very successful in bacteria and Drosophila (Cooley et al., 1988) and recently has become a powerful tool in corn (Arabidopsis; (Marks et al., 1991; Koncz et al. 1990); and Antirrhinum (Sommer et al., 1990). Insertional mutagenesis may be accomplished using standard molecular biology techniques.

b. Chemical Mutagenesis

Chemical mutagenesis offers certain advantages, such as the ability to find a full range of mutations with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the 04 position of thymine induced by exposure to n-nitrosoureas results in TA to CG transitions.

c. Radiation Mutagenesis

Biological molecules are degraded by ionizing radiation. Adsorption of the incident energy leads to the formation of ions and free radicals, and breakage of some covalent bonds.

Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage, generally proportional to the dose rate.

In the present invention, the term "ionizing radiation" means radiation comprising particles or photons that have sufficient energy or can produce sufficient energy to produce ionization (gain or loss of electrons). An exemplary and preferred ionizing radiation is an x-radiation. The amount of ionizing radiation needed in a given cell or for a particular molecule generally depends upon the nature of that cell or molecule and the nature of the mutation target. Means for determining an effective amount of radiation are well known in the art.

d. In Vitro Scanning Mutagenesis

Random mutagenesis also may be introduced using error prone PCR. The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In vitro scanning saturation mutagenesis provides a rapid method for obtaining a large amount of structure-function information including (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

2. Site-Directed Mutagenesis

Structure-guided site-specific mutagenesis represents a powerful tool for the dissection and engineering of protein-ligand interactions (Wells, 1996; Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as $E.$ $coli$ polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as $E.$ $coli$ cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Zeng et al., 1996; Burton and Barbas, 1994; Yelton et al., 1995; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis. Other methods of site-directed mutagenesis are disclosed in U.S. Pat. Nos. 5,220,007; 5,284,760; 5,354,670; 5,366,878; 5,389,514; 5,635,377; and 5,789,166.

C. Vectors

The term "vector" is used to refer to a carrier nucleic acid molecule into which an exogenous nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference. In addition to encoding a modified polypeptide such as modified gelonin, a vector may encode non-modified polypeptide sequences such as a tag or targeting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

In accordance with the present invention, vaccinia virus is itself an expression vector. There are other viral and non-viral vectors that may also be used to engineer the vaccinia viruses of the present invention. In one embodiment, such vectors may be engineered to express GM-CSF.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. In certain embodiments of the invention, the promoter is a vaccinia virus promoter that is active during the replication cycle of vaccinia virus. In particular, the promoter may be the vaccinia virus late promoter—expression under control of late promoter ties expression to later stage in replication cycle, resulting in enhanced cancer-selectivity (because late gene expression should be minimal or non-existent in normal tissues). Gene expression could also be controlled under the synthetic early-late promoter to maximize the duration and the level of gene expression. Mastrangelo et al., 1999, which is hereby incorporated by reference.

Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. Particular promoters are those that can be active in the cytoplasm because the virus replicates in the cytoplasm.

Table 2 lists several elements/promoters that may be employed, in the context of certain embodiments of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchison et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |

TABLE 2-continued

Promoter and/or Enhancer

| Promoter/Enhancer | References |
|---|---|
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |

TABLE 3-continued

| Inducible Elements | | |
|---|---|---|
| Element | Inducer | References |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor TI (Wu et al., 1997), human platelet endothelial cell adhesion molecule-1 (Almendro et al., 1996), and the SM22α promoter.

Also contemplated as useful in the present invention are the dectin-1 and dectin-2 promoters. Additional viral promoters, cellular promoters/enhancers and inducible promoters/enhancers that could be used in combination with the present invention are listed in Tables 2 and 3. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest. Alternatively, a tissue-specific promoter for cancer gene therapy (Table 4) or the targeting of tumors (Table 5) may be employed with the nucleic acid molecules of the present invention.

TABLE 4

| Candidate Tissue-Specific Promoters for Cancer Gene Therapy | | |
|---|---|---|
| Tissue-specific promoter | Cancers in which promoter is active | Normal cells in which promoter is active |
| Carcinoembryonic antigen (CEA)* | Most colorectal carcinomas; 50% of lung carcinomas; 40–50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas cells | Type II pneumocytes; Clara |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g., Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 5
Candidate Promoters for Use with a Tissue-Specific Targeting of Tumors

| Promoter | Cancers in which Promoter is active | Normal cells in which Promoter is active |
| --- | --- | --- |
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

D. Nucleic Acid Detection

In addition to their use in directing the expression of poxvirus proteins, polypeptides and/or peptides, the nucleic acid sequences disclosed herein have a variety of other uses. For example, they have utility as probes or primers for embodiments involving nucleic acid hybridization. They may be used in diagnostic or screening methods of the present invention. Detection of nucleic acids encoding poxvirus or poxvirus polypeptide modulators are encompassed by the invention.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0. 1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al, 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (ds-DNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

E. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

5. Lipid Components and Moieties

In certain embodiments, the present invention concerns compositions comprising one or more lipids associated with a nucleic acid, an amino acid molecule, such as a peptide, or another small molecule compound. In any of the embodiments discussed herein, the molecule may be either a poxvirus polypeptide or a poxvirus polypeptide modulator, for example a nucleic acid encoding all or part of either a poxvirus polypeptide, or alternatively, an amino acid molecule encoding all or part of poxvirus polypeptide modulator. A lipid is a substance that is characteristically insoluble in water and extractable with an organic solvent. Compounds than those specifically described herein are understood by one of skill in the art as lipids, and are encompassed by the compositions and methods of the present invention. A lipid component and a non-lipid may be attached to one another, either covalently or non-covalently.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or amino acid molecule, such as a peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid/poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine(Gibco BRL)-poxvirus or Superfect (Qiagen)-poxvirus complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

V. GM-CSF

In a particular aspect of the invention, the vaccinia viruses will carry a gene encoding for GM-CSF. GM-CSF is granulocyte-macrophage colony-stimulating factor, a substance that helps make more white blood cells, especially granulocytes, macrophages, and cells that become platelets. It is a cytokine that belongs to the family of drugs called hematopoietic (blood-forming) agents, and is also known as sargramostim. GM-CSF was first cloned and sequence in 1985 by Cantrell et al. (1985). Human GM-CSF is a 144-amino acid glycoprotein encoded by a single open-reading frame with a predicted molecular mass of 16,293 daltons. It exhibits a 69% nucleotide homology and 54% amino acid homology to mouse GM-CSF and exists as a single-copy gene.

GM-CSF is produced by a number of different cell types (including activated T cells, B cells, macrophages, mast cells, endothelial cells and fibroblasts) in response to cytokine or immune and inflammatory stimuli. Besides granulocyte-macrophage progenitors, GM-CSF is also a growth factor for erythroid, megakaryocyte and eosinophil progenitors. On mature hematopoietic cells, GM-CSF is a survival factor for and activates the effector functions of granulocytes, monocytes/macrophages and eosinophils. GM-CSF has also been reported to have a functional role on non-hematopoietic cells. It can induce human endothelial cells to migrate and proliferate.

GM-CSF is species specific and human GM-CSF has no biological effects on mouse cells. GM-CSF exerts its biological effects through binding to specific cell surface receptors. The high affinity receptors required for human GM-CSF signal transduction have been shown to be heterodimers consisting of a GM-CSF-specific α chain and a common β chain that is shared by the high-affinity receptors for IL-3 and IL-5.

Although GM-CSF can stimulate the proliferation of a number of tumor cell lines, including osteogenic sarcoma, carcinoma and adenocarcinoma cell lines, clinical trials of GM-CSF (alone or with other immunotherapies) are in progress for people with melanoma, leukemia, lymphoma, neuroblastoma, Kaposi sarcoma, mesothelioma, lung cancer, breast cancer, prostate cancer, colorectal cancer, brain tumors, kidney cancer and cervical cancer. Common side effects of GM-CSF include flu-like symptoms (fever, headaches, muscle aches), rashes, facial flushing, and bone pain.

VI. Other Heterologous Genes

In some embodiments, the vaccinia virus used in methods of the invention contains a nucleic acid sequence that expresses a heterologous sequence that does not encode GM-CSF but encodes another heterologous sequence. In certain embodiments, the heterologous sequence encodes another cytokine. Alternatively or additionally, the vaccinia virus may contain a nucleic acid that encodes for IL-12, thymidine deaminase, TNF, and the like. In addition, any gene product discussed herein may be encoded by a nucleic acid contained within a vaccinia virus and used in methods of the invention.

VII. Pharmaceutical Formulations, Delivery, and Treatment Regimens

In an embodiment of the present invention, a method of treatment for a hyperproliferative disease, such as cancer, by the delivery of a vaccinia virus, is contemplated. Examples of cancer contemplated for treatment include lung cancer, head and neck cancer, breast cancer, pancreatic cancer, prostate cancer, renal cancer, uterine cancer, bone cancer, testicular cancer, cervical cancer, gastrointestinal cancer, lymphomas, pre-neoplastic lesions in the lung, colon cancer, melanoma, bladder cancer and any other cancers or tumors that may be treated.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

Cancer cells that may be treated by methods and compositions of the invention include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The present invention contemplates methods for inhibiting or preventing local invasiveness and/or metastasis of any type of primary cancer. For example, the primary cancer may be melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder. In certain embodiments of the present invention, the primary cancer is lung cancer. For example, the lung cancer may be non-small cell lung carcinoma.

Moreover, the present invention can be used to prevent cancer or to treat pre-cancers or premalignant cells, including metaplasias, dysplasias, and hyperplasias. It may also be used to inhibit undesirable but benign cells, such as squamous metaplasia, dysplasia, benign prostate hyperplasia cells, hyperplastic lesions, and the like. The progression to cancer or to a more severe form of cancer may be halted, disrupted, or delayed by methods of the invention involving GM-CSF polypeptides or other polypeptide(s) encoded by a vaccinia virus, as discussed herein.

A. Administration

To kill cells, inhibit cell growth, inhibit metastasis, decrease tumor or tissue size and otherwise reverse or reduce the malignant phenotype of tumor cells, using the methods and compositions of the present invention, one would generally contact a hyperproliferative cell with the therapeutic compound such as a polypeptide or an expression construct encoding a polypeptide. The routes of administration will vary, naturally, with the location and nature of the lesion, and include, e.g., intradermal, transdermal, parenteral, intravenous, intramuscular, intranasal, subcutaneous, regional, percutaneous, intratracheal, intraperitoneal, intraarterial, intravesical, intratumoral, inhalation, perfusion, lavage, direct injection, and oral administration and formulation.

The present invention specifically concerns intravascular administration of a vaccinia virus of the invention. The term "intravascular" is understood to refer to delivery into the vasculature of a patient, meaning into, within, or in a vessel or vessels of the patient. In certain embodiments, the administration is into a vessel considered to be a vein (intravenous), while in others administration is into a vessel considered to be an artery. Veins include, but are not limited to, the internal jugular vein, a peripheral vein, a coronary vein, a hepatic vein, the portal vein, great saphenous vein, the pulmonary vein, superior vena cava, inferior vena cava, a gastric vein, a splenic vein, inferior mesenteric vein, superior mesenteric vein, cephalic vein, and/or femoral vein. Arteries include, but are not limited to, coronary artery, pulmonary artery, brachial artery, internal carotid artery, aortic arch, femoral artery, peripheral artery, and/or ciliary artery. It is contemplated that delivery may be through or to an arteriole or capillary.

Injection into the tumor vasculature is specifically contemplated for discrete, solid, accessible tumors. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a poxvirus polypeptide or a poxvirus comprising a mutation that renders the poxvirus advantageous for treatment of cancer or cancer cells. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

B. Injectable Compositions and Formulations

The preferred method for the delivery of an expression construct or virus encoding all or part of a poxvirus genome to cancer or tumor cells in the present invention is via intratumoral injection. However, the pharmaceutical compositions disclosed herein may alternatively be administered parenterally, intravenously, intradermally, intramuscularly, transdermally or even intraperitoneally as described in U.S. Pat. Nos. 5,543,158; 5,641,515 and 5,399,363 (each specifically incorporated herein by reference in its entirety).

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

C. Combination Treatments

The compounds and methods of the present invention may be used in the context of hyperproliferative diseases/conditions including cancer and atherosclerosis. In order to increase the effectiveness of a treatment with the compositions of the present invention, such as attenuated vaccinia viruses, it may be desirable to combine these compositions with other agents effective in the treatment of those diseases and conditions. For example, the treatment of a cancer may be implemented with therapeutic compounds of the present invention and other anti-cancer therapies, such as anti-cancer agents or surgery.

Various combinations may be employed; for example, an attenuated poxvirus, such as vaccinia virus, is "A" and the secondary anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/A/B/A | B/B/A/A | |
| B/A/B/A | B/A/A/B | A/A/A/B | B/A/A/A | A/B/A/A | A/A/B/A | | |

Administration of the therapeutic expression constructs of the present invention to a patient will follow general protocols for the administration of that particular secondary therapy, taking into account the toxicity, if any, of the poxvirus treatment. It is expected that the treatment cycles would be repeated as necessary. It also is contemplated that various standard therapies, as well as surgical intervention, may be applied in combination with the described cancer or tumor cell therapy.

1. Anti-Cancer Therapy

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al, 1992). In the context of the present invention, it is contemplated that poxvirus therapy could be used similarly in conjunction with chemotherapeutic, radiotherapeutic, immunotherapeutic or other biological intervention, in addition to other pro-apoptotic or cell cycle regulating agents.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of certain poxvirus polypeptides would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL-4, IL-12, GM-CSF, IFNγ, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., *Mycobacterium bovis*, *Plasmodium falciparum*, dinitrochlorobenzene and aromatic compounds) (U.S. Pat. Nos. 5,801,005; 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the poxvirus-related therapies described herein.

Passive Immunotherapy. A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie and Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

Active Immunotherapy. In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anti-carbohydrate antibodies.

Adoptive Immunotherapy. In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

d. Genes

In yet another embodiment, the secondary treatment is a gene therapy in which a therapeutic polynucleotide is administered before, after, or at the same time as an attenuated poxvirus is administered. Delivery of a poxvirus in conjunction with a vector encoding one of the following gene products will have a combined anti-cancer effect on target tissues. Alternatively, the poxvirus may be engineered as a viral vector to include the therapeutic polynucleotide. A variety of proteins are encompassed within the invention, some of which are described below.

Inducers of Cellular Proliferation. The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that antisense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

Inhibitors of Cellular Proliferation. The tumor suppressor oncogenes function to inhibit excessive cellular proliferation. The inactivation of these genes destroys their inhibitory activity, resulting in unregulated proliferation. The tumor suppressors p53, p16 and C-CAM are described below.

In addition to p53, which has been described above, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p_{16}^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $_{16}^{B}$, p19, $p21^{WAF1}$, and $p_{27}^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1994; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, antithrombotic genes (e.g., COX-1, TFPI), PGS, Dp, E2F, ras, myc, neu, raf erb, fms, trk, ret, gsp, hst, abl, E1A, p300, genes involved in angiogenesis (e.g., VEGF, FGF, thrombospondin, BAI-1, GDAIF, or their receptors) and MCC.

Regulators of Programmed Cell Death. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., BCIXL, Bclw, Bcls, Mcl-1, Al, Bfl-1) or counteract Bcl-2 function and promote cell death (e.g., Bax, Bak, Bik, Bim, Bid, Bad, Harakiri).

D. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al., 1999).

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

TABLE 6

Oncogenes

| Gene | Source | Human Disease | Function |
|---|---|---|---|
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases | | | |
| ERBB/HER | Avian erythroblastosis virus; ALV promoter insertion; amplified human tumors | Amplified, deleted Squamous cell Cancer; glioblastoma | EGF/TGF-α/ Amphiregulin/ Hetacellulin receptor |
| ERBB-2/NEU/HER-2 | Transfected from rat Glioblastomas | Amplified breast, Ovarian, gastric cancers | Regulated by NDF/ Heregulin and EGF-Related factors |
| FMS | SM feline sarcoma virus | | CSF-1 receptor |
| KIT | HZ feline sarcoma virus | | MGF/Steel receptor Hematopoieis |
| TRK | Transfection from human colon cancer | | NGF (nerve growth Factor) receptor |
| MET | Transfection from human osteosarcoma | | Scatter factor/HGF Receptor |
| RET | Translocations and point mutations | Sporadic thyroid cancer; Familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like Transcription factor)/ PDGF receptor gene Fusion |
| TGF-β receptor | | Colon carcinoma Mismatch mutation target | |
| NONRECEPTOR TYROSINE KINASES | | | |
| ABI. | Abelson Mul.V | Chronic myelogenous Leukemia translocation with BCR | Interact with RB, RNA Polymerase, CRK, CBL |
| FPS/FES | Avian Fujinami SV; GA FeSV | | |
| LCK | Mul.V (murine leukemia virus) promoter insertion | | Src family; T cell Signaling; interacts CD4/CD8 T cells |

TABLE 6-continued

| Oncogenes | | | |
|---|---|---|---|
| Gene | Source | Human Disease | Function |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |
| MISCELLANEOUS CELL SURFACE | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and Drosophila homology | Nevoid basal cell cancer Syndrome (Gorline syndrome) | 12 transmembrane domain; signals through Gli homogue CI to antagonize Hedgehog pathway |
| TAN-1 Notch homologue | Translocation | T-ALI. | Signaling |
| MISCELLANEOUS SIGNALING | | | |
| BCL-2 | Translocation | B-cell lymphoma | Apoptosis |
| CBL | Mu Cas NS-1 V | | Tyrosine-Phosphorylated RING finger interact Abl |
| CRK | CT1010 ASV | | Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |
| GUANINE NUCLEOTIDE EXCHANGERS AND BINDING PROTEINS | | | |
| BCR | | Translocated with ABL in CML | Exchanger; protein Kinase |
| DBL | Transfection | | Exchanger |
| GSP | | | |
| NF-1 | Hereditary tumor Suppressor | Tumor suppressor Neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary Cancer/ovarian cancer | Localization unsettled |
| BRCA2 | Heritable suppressor | Mammary cancer | Function unknown |
| ERBA | Avian erythroblastosis Virus | | Thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | Transcription factor with c-JUN |
| GLI | Amplified glioma | Glioma | Zinc finger; cubitus Interruptus homologue is in hedgehog signaling pathway; inhibitory link PTC and hedgehog |

TABLE 6-continued

| | Oncogenes | | |
|---|---|---|---|
| Gene | Source | Human Disease | Function |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II Elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin Regulation; interact RB?; regulate Apoptosis? |
| N-MYC | Amplified | Neuroblastoma | |
| L-MYC | | Lung cancer | |
| REL | Avian Retriculoendotheliosis Virus | | NF-κB family Transcription factor |
| SKI | Avian SKV770 Retrovirus | | Transcription factor |
| VHL | Heritable suppressor | Von Hippel-Landau Syndrome | Negative regulator or elongin; transcriptional elongation complex |
| WT-1 | | Wilm's tumor | Transcription factor |
| | CELL CYCLE/DNA DAMAGE RESPONSE | | |
| ATM | Hereditary disorder | Ataxia-telangiectasia | Protein/lipid kinase Homology; DNA damage response upstream in P53 pathway |
| BCL-2 | Translocation | Follicular lymphoma | Apoptosis |
| FACC | Point mutation | Fanconi's anemia group C (predisposition Leukemia | |
| FHIT | Fragile site 3p14.2 | Lung carcinoma | Histidine triad-related Diadenosine 5', 3''''-$P^1.p^4$ tetraphosphate Asymmetric hydrolase |
| hMLI/MutL | | HNPCC | Mismatch repair; MutL Homologue |
| HMSH2/MutS | | HNPCC | Mismatch repair; MutS Homologue |
| HPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 Suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human Tumors, including hereditary Li-Fraumeni syndrome | Transcription factor; Checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; Osteosarcoma; breast Cancer; other sporadic Cancers | Interact cyclin/cdk; regulate E2F transcription factor |
| XPA | | Xeroderma Pigmentosum; skin Cancer predisposition | Excision repair; photo-product recognition; zinc finger |

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods

Viruses and cell lines. The panel of wild type poxvirus strains (Wyeth, Western Reserve (WR), USSR, Tian Tan, Tash Kent, Patwadangar, Lister, King, IHD-W, IHD-J and Evans) was kindly provided by Dr Geoff Smith, Imperial College, London. Human Adenovirus serotype 5 (Ad5) was obtained from ATCC. The Viral growth factor (VGF) deleted strain of WR (vSC20) was kindly provided by Dr Bernie Moss, NIH. The thymidine kinase deleted strain of WR (vJS6) and the TK-, VGF-double deleted strain of WR (vvDD) are described in Puhlmann et al. (2000) and McCart et al. (2001). WR strain expressing firefly luciferase was kindly provided by Dr Gary Luker, (Uni Michigan).

Vaccinia strain JX-963 was constructed by recombination of a version of the pSC65 plasmid containing the *E. coli* gpt and human GM-CSF genes (under the control of the p7.5 and pSE/L promoters respectively) into the thymidine kinase gene of the vSC20 (VGF deleted) strain of WR. Further selection of white plaques after propagation of the virus in X-Gal produced a virus with non-functioning lacZ (lacZ is expressed from within VGF in vSC20). Correct insertion into the TK gene and loss of lacZ function was verified by sequencing and GM-CSF production verified by ELISA.

The vvDD expressing luciferase was constructed by insertion of a version of the pSC65 plasmid with luciferase under control of the p7.5 promoter into vSC20. Bioluminescence was verified using an IVIS 50 system (Xenogen, Alameda).

The human tumor cell lines include A2780 (Ovarian, obtained from ECACC), A549 (lung, obtained from ECACC), HCT 116, HT-29 and SW620 (colon, obtained from ATCC), HT-1080 (fibrosarcoma, obtained from ATCC), LNCaP (prostate, obtained from ATCC), PANC-1 (pancreatic, obtained from ATCC), MCF-7 (breast, obtained from ATCC). Non-transformed cells include MRC-5 (lung fibroblast, obtained from ATCC), Beas-2B (bronchial epithelial, kindly provided by Tony Reid, UCSD) and the primary, normal cells NHBE (Normal human bronchial epithelial) and SAEC (Small airway bronchial epithelial), both obtained from Clonetics (Walkersville, Md.).

The mouse tumor cell lines include CMT 64 (C57/B6 lung, obtained from Cancer Research UK), JC (BALB/c mammary, obtained from ATCC), MC38 (C57/B6 colon, obtained from NIH) and TIB-75 (BNL 1ME A.7R.1)(BALB/c hepatic, obtained from ATCC). The cell lines NIH 3T3 and NIH 3T3 overexpressing H-Ras were kindly provided by Richard Marais (ICR, London). The rabbit tumor cell line VX2 has been described previously (Kidd, 1940; Tjemberg, 1962; Chen et al., 2004).

In vitro replication and cytopathic effect assays. Cell lines are seeded into 6-well plates at $5 \times 10^6$ cells/well and left overnight. Virus was then added at a multiplicity of infection (MOI) of 1.0 Plaque forming units (PFU)/cell and allowed to infect for 2 h. At the end of the infection the media was changed and plates incubated for 48 h, the cells were then scraped into the media and collected. Cells were lysed by three rounds of freezing and thawing followed by sonication before serial dilutions of the crude viral lysate was added to BSC-1 cells to titer the virus. Plaque assay was performed as described previously (Earl et al., 1998). Adenovirus was titered on A549 cells (Earl et al., 1998). Studies are typically run in triplicate.

In order to assess the cytopathic effect (CPE) of the virus, cells were seeded at 1000 cells/well in 96-well plates and allowed to attach overnight. Serial dilutions of the viruses to be tested were then added to the plates in triplicate (MOI range from 100 to 0.001) and the plates incubated for a further 72 h. After this time media was replaced with media without serum and MTS (Promega) added to the plates. After 2-4 h incubation the absorbance at 450 nm was read on an ELISA plate reader. Cytopathic effect was determined as reduction in viability of a test well relative to both untreated wells containing cells only (100% viable) and cell-free wells (0% viable). Results were represented as the MOI at which 50% of the cell layer was viable (effective concentration 50%, EC50).

Mouse syngeneic and xenograft tumor model studies. Immunocompetent mice are implanted subcutaneously with syngeneic tumor cells ($1 \times 10^6$ cells/mouse), such that JC and TIB-75 cells are implanted into BALB/c mice and MC38 and CMT 64 cells are implanted into C57/B6 mice. Certain human xenograft models involve $1 \times 10^7$ HT29 cells implanted subcutaneously into SCID mice (all mice are aged 8-10 weeks and sex matched). Once tumors reached 50-100 mm$^3$ animals are regrouped and treated as indicated. Tumor sizes were followed by caliper measurement.

Mice treated with luciferase expressing virus can be imaged using an IVIS 100 system (Xenogen, Alameda). Mice are injected intraperitoneally with luciferin (30 mg/kg) and anesthetized (2% isoflurane) prior to imaging.

Some mice are sacrificed at times indicated post-treatment and organs are recovered for viral biodistribution or immunohistochemical studies. For viral biodistribution, organs are snap frozen and ground before plaque assays are performed as described. For immunohistochemistry studies, organs are fixed in formalin before embedding in paraffin blocks for sectioning. Sections are stained with hematoxylin and eosin (H & E) and with viral coat proteins (polyclonal anti-vaccinia antibody or polyclonal antihexon antibody for adenovirus treated animals).

Rabbit model. The implantation of VX2 tumors into the livers of New Zealand White rabbits and the measurement of tumor progression and metastasis to the lungs by CT and ultrasound scans has been described previously (Paeng et al., 2003).

Cytotoxic T-lymphocyte (CTL) assay. This is performed by mixing labeled peripheral blood lymphocytes (PBLs) obtained from rabbits treated as indicated with VX2 tumor cells. After a 4 h period cell apoptosis was measured by propidium iodide staining and flow cytometry.

Neutralizing Antibody assay. Production of anti-vaccinia neutralizing antibody is measured in the plasma obtained from rabbits post-treatment. Dilutions of plasma are mixed with 1000 PFU of vaccinia overnight before addition to a 96-well plate containing A2780 cells. After 72 h cell viability is measured by MTS assay. Viral neutralization is measured as the dilution of plasma required to prevent viral inactivation.

Statistical analyses. Kaplan-Meier curves are compared using the Generalized Wilcoxin test. Tumor response rates and metastasis-free rates are typically compared with Fisher's exact test.

Example 2

Rat Tumor Model

Rats (Sprague-Dawley, Males) were exposed to carcinogen (N-Nitrosomorpholine, NNM) in their drinking water (175 mg/L) for a period of 8 weeks, during which time liver cirrhosis developed, followed by in situ development of tumors (hepatocellular carcinoma or cholangiocarcinoma) within the liver between weeks 16-20 on average (model previously described in Oh et al., 2002). Tumor detection and evaluation was performed by an experienced ultrasonographer using ultrasound imaging. Tumor sizes were approximately 0.75-1.5 cm. in diameter at baseline immediately prior to treatment initiation; tumor volumes were not significantly different at baseline between the control and treatment groups (estimated mean volumes were 400-500 mm$^3$). Control animals (n=17) received no treatment, whereas treated animals (n=6) received intravenous injections (via tail vein) with a poxvirus (Wyeth strain; thymidine kinase gene deletion present) expressing human GM-CSF from a synthetic early-late promoter (virus construct described in Mastrangelo et al., 1999). Virus was administered at a dose of $10^8$ plaque-forming units (titered as in Earl et al., 1998) in a total volume of 0.75 ml; (virus suspension mixed with 10 mM Tris up to the desired volume) intravenously by tail vein over 60 seconds. Treatment was repeated every two weeks for three total doses (day 1, 15 and 29).

Over ten weeks following the initiation of treatment, the control tumors increased in size significantly until reaching a mean of approximately 3000 mm$^3$ (S.E. 500) (FIG. 1). Control animals needed to be sacrificed for ethical reasons due to tumor progression at this time. All tumors had increased in size significantly. In contrast, five of the six treated tumors regressed completely (below the limit of detection by ultrasound). The mean tumor volume in the treated group was approximately 50 mm$^3$ (S.E., <10; p<0.01 vs. controls).

Example 3

Rabbit VX2 Tumor Model

Figure 2:
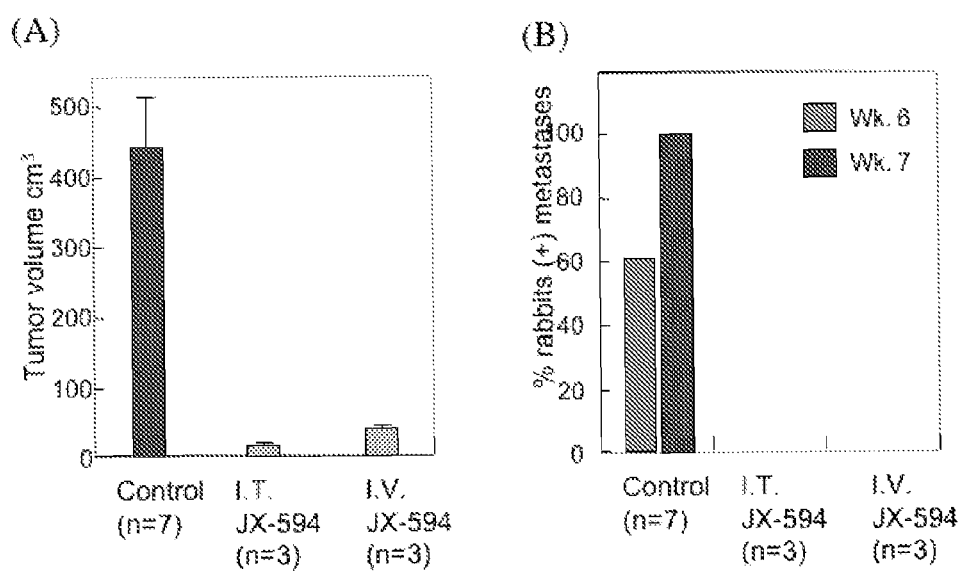
FIGS. 2A-2B—JX-594 Intravenous dose treatment of VX2 liver tumors in rabbits, efficacy against primary tumor and metastases. VX2 cells (from a dissociated 1 mm$^3$ tumor) were implanted into the liver of New Zealand white rabbits and tumor growth followed by ultrasound (US) and CT scan. Once tumors reached 2-4 cm$^3$ animals were treated with a single dose of PBS (n=7) or JX-594 (1×10$^9$ PFU), via intravenous or US guided IT injection (n=3/group).

A study was performed in a VX2 rabbit carcinoma model (as described in Paeng et al., 2003). Rabbit was selected as a species because human GM-CSF was previously demonstrated to have significant biological activity in rabbits (in contrast to mice). VX2 tumors were grown in muscle of New Zealand white rabbits and cells from a 1-2 mm$^3$ fragment of tumor were dissociated, resuspended in 0. 1 ml normal saline and were injected beneath the liver capsule (21 gauge needle; injection site covered with surgical patch with a purse-string tie) and allowed to grow for 14 days until primary tumors were established (mean diameter, 1.5-2.0 cm; est. volume 2-4 cm$^3$). VX2 cells were demonstrated to be infectable by vaccinia poxvirus ex vivo in a standard burst assay. Tumor sizes were monitored over time by CT scanning and by ultrasound. Over the following seven weeks, control (untreated) animals (n=18) developed tumor progression within the liver, with estimated mean tumor volumes reaching approximately 100 cm$^3$ (S.E. approximately 20). In addition, numerous tumor metastases progressed and became detectable within the lungs and livers over time (FIGS. 2A-B). By week 7, control animals all had detectable metastases, with a mean number of lung metastases of 17 (S.E. 2.3). The median survival of these control animals was 55 days (post-treatment initiation in treated animals), and all were dead within 80 days.

Treated animals (n=3) in the first experiment received a single intravenous injection (via tail vein) with a poxvirus (Wyeth strain; thymidine kinase gene deletion present) expressing human GM-CSF from a synthetic early-late promoter (virus construct described in Mastrangelo et al., 1999). Virus was administered at a dose of $10^9$ plaque-forming units (titered as in Earl et al., 1998) in a total volume of 7 ml; (virus suspension mixed with 10 mM Tris up to the desired volume) intravenously by ear vein over 60 seconds. By week seven, in contrast to controls, treated animals had no lung metastases detectable by CT scanning (FIGS. 2A-2B). Survival was significantly increased, also. By 110 days post-treatment initiation, the median survival had not been reached, and approximately 70% were still alive.

Figure 3:
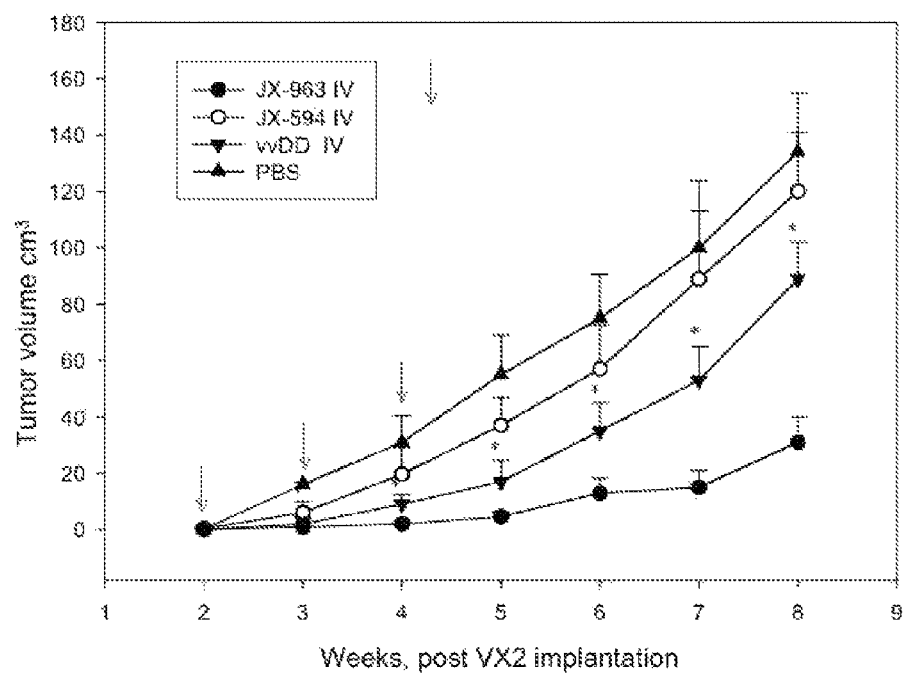
FIG. 3—JX-594 and JX-963 lower dose intravenous repeat treatments of VX2 liver tumors in rabbits. Tumor cells were implanted as described in (FIGS. 2A-2B). Animals were treated intravenously 3 times (every two weeks, arrows) after tumors reached 2-4 cm³ with 1×10⁸ PFU of JX-594, JX-963 or vvDD (n=6/group), or PBS (n=18). Subsequent primary tumor volume was followed by CT scan.
Figure 4:
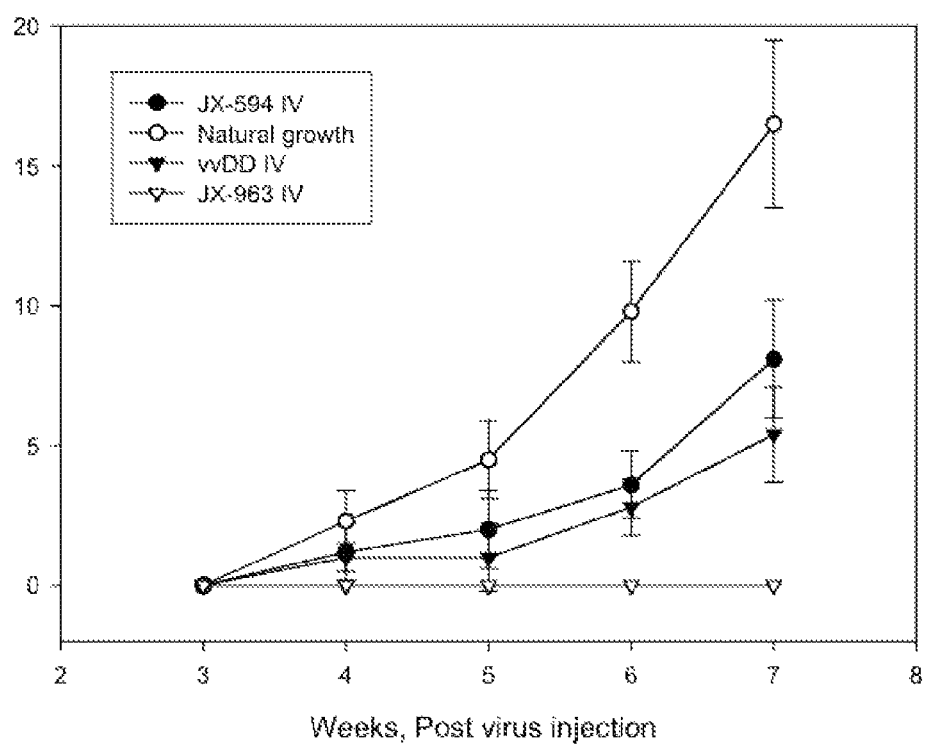
FIG. 4—Effects of JX-594, vvDD and JX-963 on lung metastases in rabbits bearing VX2 liver tumors. Animals (from studies described in FIG. 3) were examined for liver metastases by CT scan at weekly intervals after the beginning of therapy. The mean number of detectable metastases per animal in each group is shown.
Figure 5:
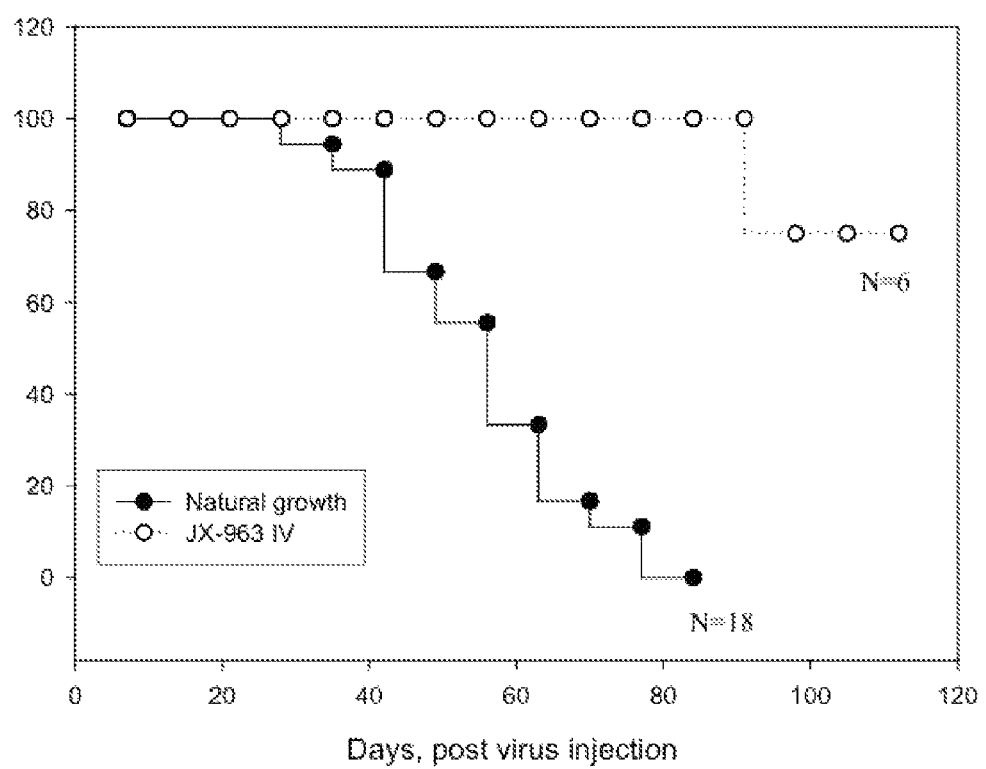
FIG. 5—Survival of rabbits bearing VX2 liver tumors after IV delivery of JX-963. Animals bearing liver tumors were treated with 3 doses of 1×10⁸ PFU of JX-963 as described in FIG. 3. A Kaplin-Meier survival curve of these animals and the control treated group are shown. As the JX-594 and vvDD groups did not show significant differences in survival, JX594 and vvDD groups were not included.

Treated animals (n=6 per group) in a second experiment received three weekly intravenous injections (via tail vein) with either (i) JX-594, a poxvirus (Wyeth strain; thymidine kinase gene deletion present) expressing human GM-CSF from a synthetic early-late promoter (virus construct described in Mastrangelo et al., 1999, which is hereby incorporated by reference); (ii) vvDD, a vaccinia WR strain with deletions in thymidine kinase and vaccinia growth factor genes (vvDD as described by McCart et al, 1999); (iii) or JX-963, vaccinia WR strain with deletions in thymidine kinase and vaccinia growth factor genes and expressing human GM-CSF from a synthetic early-late promoter. Virus was administered at a dose of $10^8$ plaque-forming units (titered as in Earl et al., 1998) in a total volume of 7 ml; (virus suspension mixed with 10 mM Tris up to the desired volume) intravenously by ear vein over 60 seconds. By week seven, in contrast to controls, JX-963 treated animals had no lung metastases detectable by CT scanning (p<0.01 vs. controls) (FIG. 4). JX-594-treated animals had a mean of 8 lung tumors (S.E. 2; p<0.05 vs controls). vvDD-treated animals had a mean of 5 lung tumors (S.E. 2; p<0.05 vs controls). Of note, JX-963 and vvDD also had significant efficacy against the primary tumor growth in the liver, in contrast to JX-594 at this dose (FIG. 3) and JX-963 dramatically increased the survival of these animals (FIG. 5).

The GM-CSF-expressing virus JX-963 had significantly better efficacy against both primary tumors and lung metastases than its non-GM-CSF-expressing control vvDD; 2) the GM-CSF-expressing virus JX-963 had significantly better efficacy against both primary tumors and lung metastases than its GM-CSF-expressing Wyeth strain control (despite an additional deletion in the vgf gene not present in JX-594). Therefore, intravenous administration with a vaccinia expressing human GM-CSF resulted in significantly better efficacy over the same vaccinia without GM-CSF, and intravascular administration of a WR strain deletion mutant expressing human GM-CSF was significantly better than a Wyeth strain (standard vaccine strain) deletion mutant expressing GM-CSF.

Example 4

Systemic Cancer Efficacy with JX-963

Targeted therapies hold great promise for the treatment of cancer, but novel agents are still needed as resistance frequently develops through mutation of the target molecules and/or tumor escape through pathway redundancies. Oncolytic viruses are viruses that have their replication restricted to malignant cell types, either inherently or through genetic engineering (Thorne et al., 2005)[1]. Selective intratumoral replication leads to virus multiplication, killing of the infected cancer cell by unique and apoptosis-independent mechanisms (oncolysis) and spread of the virus to other tumor cells. Virotherapeutics therefore have the potential to effectively treat refractory cancers and clinical proof-of-concept has been achieved with local or regional administration for several oncolytic viruses (Parato et al., 2005)[2]. However, for oncolytic viruses to have a major impact on patient survival, systemic efficacy and intravenous delivery will be needed.

Figure 10:
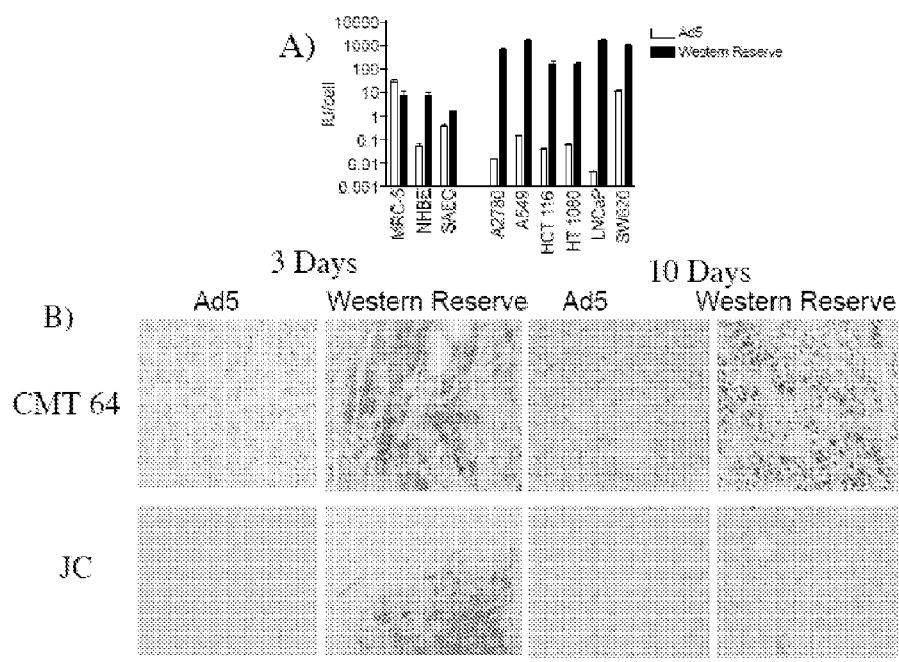
FIGS. 10A-10B—Viral production of cell lines infected with either WR or Ad5, and cytopathic effect produced by viral infection.

The inventor has therefore undertaken a stepwise design and development strategy to create a more effective systemic agent. First, the inventor identified poxviruses such as vaccinia as a virus species that has evolved for systemic dissemination and resistance to clearance by complement and antibodies (Smith et al., 1997; Buller and Palumbo, 1991). Vaccinia has well-defined mechanisms to allow for transport in the blood without inactivation and can spread rapidly within tissues, it also has a long history of human use during the smallpox eradication campaign. A panel of vaccinia viruses used during the vaccination program, and some related strains were screened for their ability to replicate in normal (NHBE) and tumor (A2780) cells. All vaccinia strains replicated to higher levels in the tumor cell line than in the normal cells (FIG. 6A), but the therapeutic index (tumor to normal cell replication ratio) varied between strains. Strains used extensively in the laboratory (such as Western Reserve (WR)) tended to display greater inherent tumor selectivity in vitro than their parental vaccine strains (Wyeth). This is the first time that wild type vaccinia strains have been shown to display inherent superior replication in tumor cell lines relative to normal cells. This is not true for all viruses however, as Adenovirus serotype 5 (Ad5) (the backbone for the majority of oncolytic viruses in the clinic) did not display such selectivity (FIG. 10A).

Figure 6:
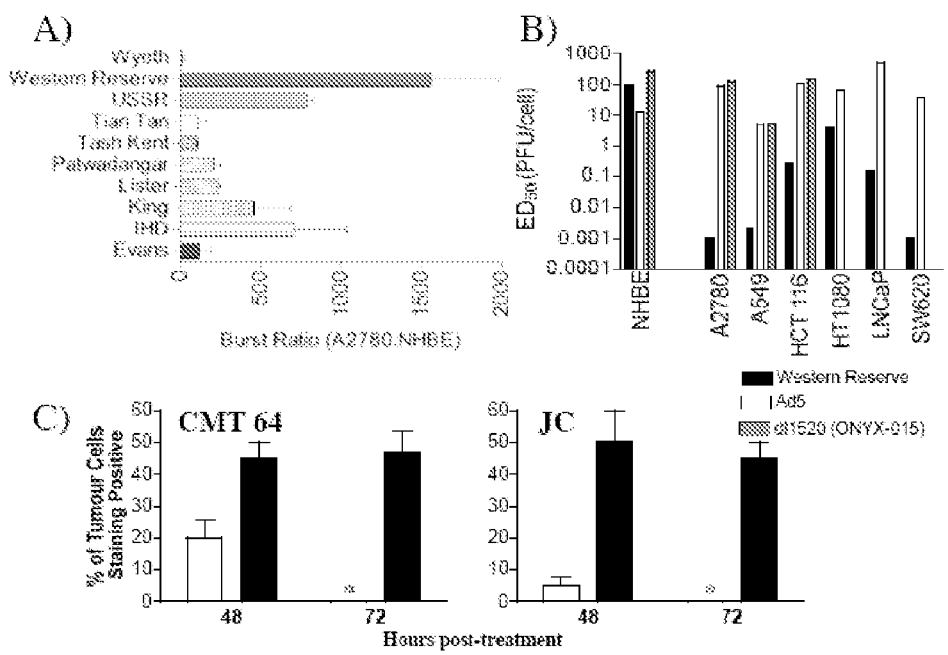
FIGS. 6A-6C—Burst ratio of vaccinia strains, cytopathic effect, and systemic delivery of viral strains to tumors.

Another desirable attribute for an oncolytic agent is rapid intratumoral spread (Wein et al., 2003). This can be achieved through a short replication cycle and early release of virus from infected cells. The ability of the WR strain of vaccinia to destroy tumor cells was therefore examined at early time points (72 h) after infection and compared to Ad5 and the oncolytic adenovirus strain dII520 (ONYX-015) (Heise et al., 1997) (FIG. 6B). WR displayed up to 5-logs of increased killing potential in tumor cells at this time relative to both Ad5 and dII520, as well as greater tumor selectivity than either adenoviral strain.

The major limitation of most oncolytic viruses tested to date is an inability to efficiently infect tumors following systemic delivery, as seen when $1 \times 10^9$ plaque forming units (PFU) of Ad5 were delivered intravenously to subcutaneous tumor models in mice (FIG. 6C and FIG. 10B); this equates to a dose of $3.5 \times 10^{12}$ PFU in a 70 kg human, higher than ever given to a patient. Little or no replicating virus was evident in tumors (as detected by immunohistochemical staining for viral coat proteins 48 and 72 h after viral delivery). Vaccinia strain WR however could effectively traffic to and infect the tumors in these same models, with up to 50% of the tumor cells staining positive within 48 h of treatment. Furthermore, vaccinia was able to persist in the tumor for at least 10 days (FIG. 10B), despite the fact an immune response would have been initiated by this time.

Figure 7:
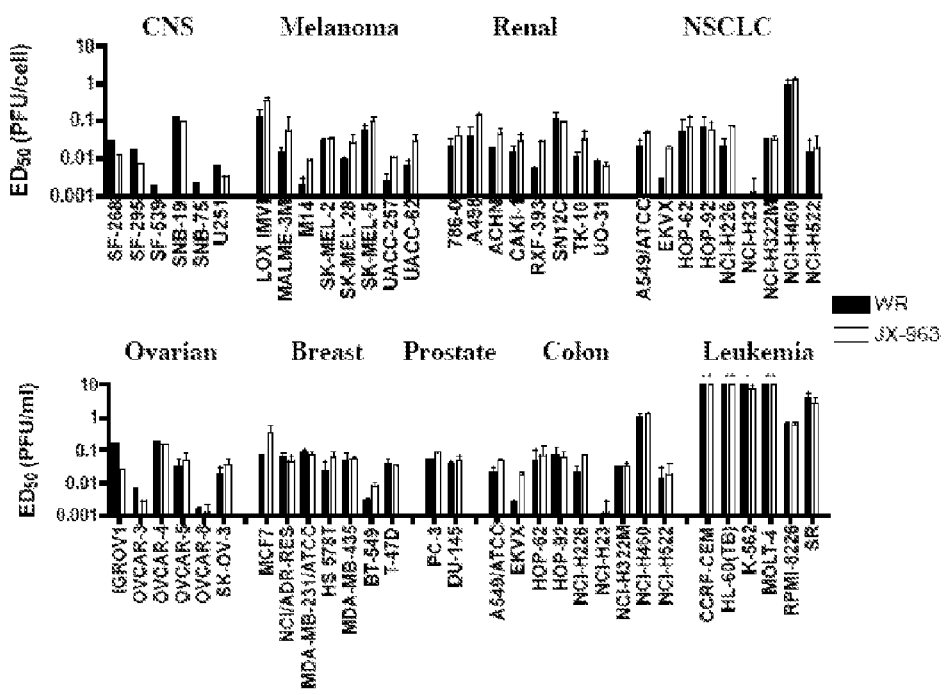
FIG. 7—Cytopathic effect of WR and vvDD on a panel of human tumor cell lines. $EC_{50}$ values were determined 72h following infection of tumor cell lines with WR or vvDD. The MOI of virus (PFU/cell) needed to reduce the cell viability to 50% of untreated control wells (ED50) is plotted FIGS. 8A-8C—Effects of overexpression of H-Ras on viral replication, biodistribution of WR and vvDD following systemic delivery to tumor bearing mice, and viral gene expression quantified by light production.
Figure 11:
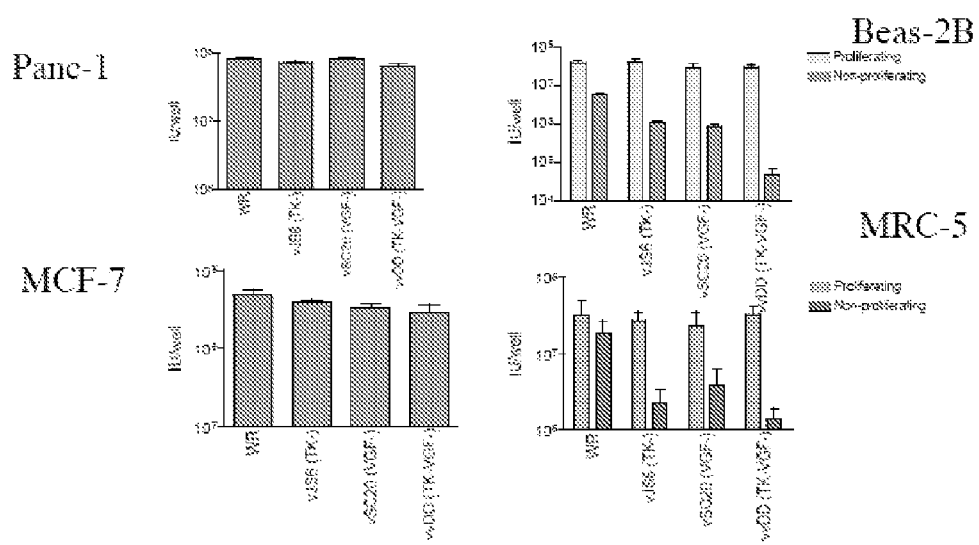
FIG. 11—Viral production of cell lines infected with either WR or Ad5. Human tumor cell lines (Panc-1 and MCF-7) or human immortalized but non-transformed cell lines (Beas-2B and MRC-5), either proliferating or grown to contact inhibition (N.B. tumor cells did not become contact inhibited), were treated with different strains of vaccinia at an MOI of 1.0 PFU/cell. Strains used were Western Reserve (WR) and WR containing deletions in either the Thymidine Kinase (TK) gene (vJS6), the viral growth factor (VGF) gene (vSC20), or containing deletions in both these genes (vvDD). Virus produced after 48 h was titered by plaque assay.

In order to maximize safety, particularly for intravenous administration in immunodeficient cancer patients, attenuating and tumor-targeting genetic deletions were introduced into the virus. The inventor has previously described preferential tumor-expression of viral genes with insertions into the vaccinia thymidine kinase (TK) gene and of TK and viral growth factor (VGF) double deletions (Puhlmann et al., 1999; McCart et al., 2001). Although the targeting mechanisms of these deletions were not previously demonstrated, the rationale was to restrict virus replication and oncolysis to cancer cells with elevated E2F levels (as E2F drives production of the cellular thymidine kinase gene product (Hengstschlager et al. 1994)) and activation of the epidermal growth factor (EGF) receptor pathway (as activation of this pathway by VGF is necessary for efficient viral replication (Andrade et al., 2004)). Here it is shown that the TK and VGF double deleted virus (vvDD) displayed an impressive ability to destroy a wide range of tumor cells of different origins (FIG. 7). It was also found that single deletions in either the vaccinia TK or the VGF genes attenuated the ability of vaccinia to replicate in non-proliferating, non-transformed human cell lines, while the double deleted virus (vvDD) was further attenuated (FIG. 11). None of these strains were attenuated in their ability to replicate in human tumor cells.

Figure 8:
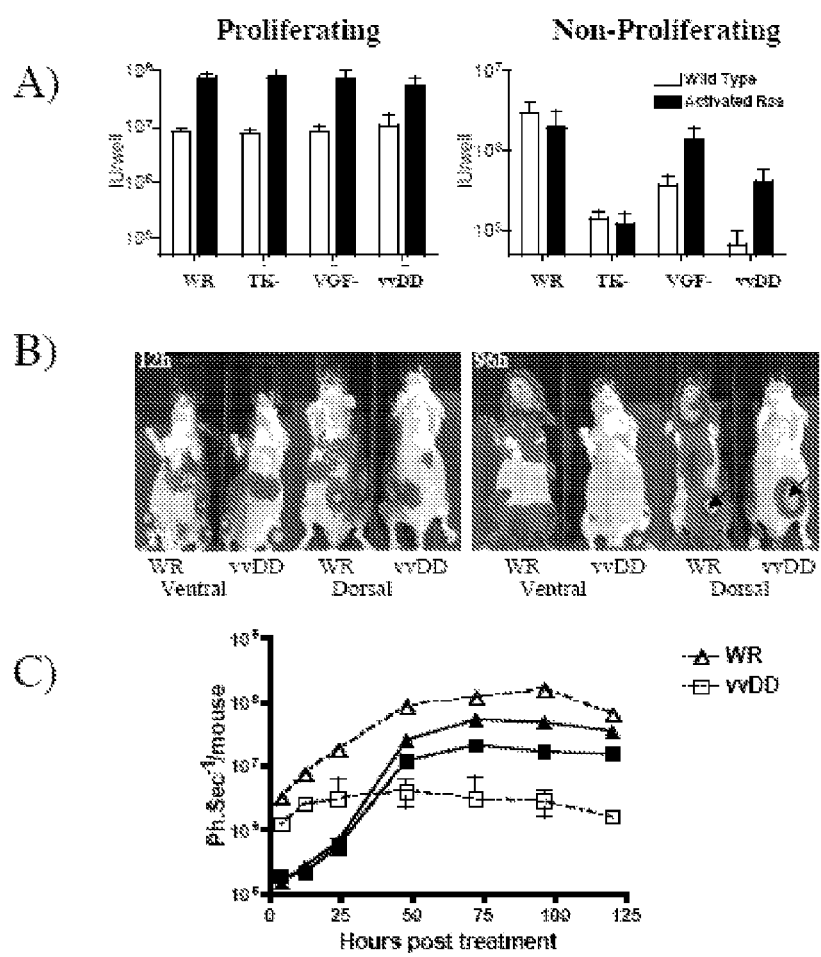

It was further found that the block in the ability of the VGF-deleted virus to replicate in non-proliferating, non-transformed cells could be overcome in cells expressing activated H-ras (FIG. 8A). It was found that H-ras activation led to increased replication of even WR (p=0.0094), and that VGF deletion did not inhibit viral replication in H-ras activated cells, whereas the TK deletion did (p=0.016). This indicates that the tumor selectivity introduced by the gene deletions in vvDD is more than a simple preference for proliferating cells, since slowly proliferating or even non-proliferating cells could be targeted if they contained mutations in the EGF-R/Ras/MAP Kinase signaling pathway.

Figure 12:
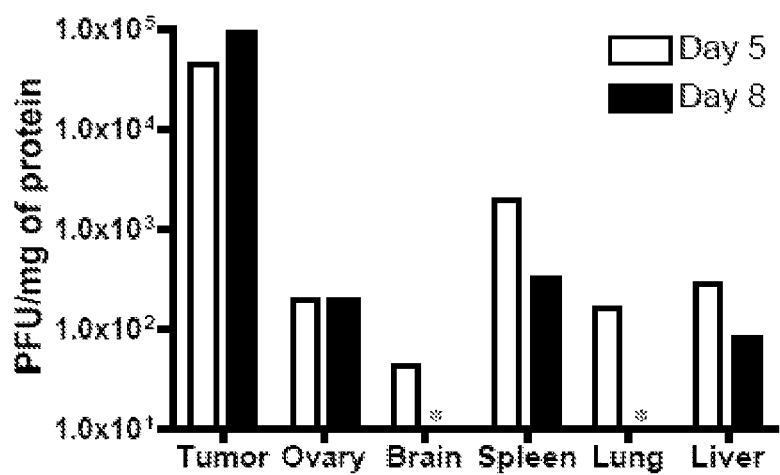
FIG. 12—Recovery of systemically delivered vvDD. Recovery of vvDD delivered systemically (intraperitoneal injection of 1×10⁹ PFU) to C57B/6 mice bearing subcutaneous MC38 tumors. Mice were sacrificed on days 5 or 8 after treatment (n=8/group) and different tissues recovered and viral infectious units (PFU/mg tissue) titered by plaque assay (*=below the limits of detection).

In order to determine whether the double deleted vaccinia (vvDD) might produce toxicity by targeting normal proliferating cells (such as gut epithelial, bone marrow or ovarian cells), in vivo viral gene expression was studied by non-invasive bioluminescence imaging (FIG. 8B) and viral biodistribution was examined post mortem (FIG. 12). Bioluminescence imaging following IV delivery of $1 \times 10^7$ PFU of WR or vvDD expressing luciferase showed that both viruses displayed similar initial infection and viral gene expression patterns (including spleen, lung, liver and tumor) (FIG. 8B). However, the bioluminescent signal from vvDD was rapidly cleared from most organs other than the tumor, even in immunodeficient mice, while WR continued to replicate in the target organs and spread to other tissues, including bone marrow, skin and brain (FIGS. 8B and 8C). Although vvDD did produce some points of infection outside of the tumor, these appeared transiently and late, indicating secondary spread without replication (data not shown). Recovery of infectious viral units from tissues of mice treated IV with $1 \times 10^9$ PFU of vvDD (a lethal dose for WR) revealed that by day 8 after treatment the tumor displayed increasing viral titer, with over 1,000-fold more viral copies per mg tissue than any other organ, while all normal tissues were below the limits of detection or showed falling viral titers (FIG. 12).

Figure 13:
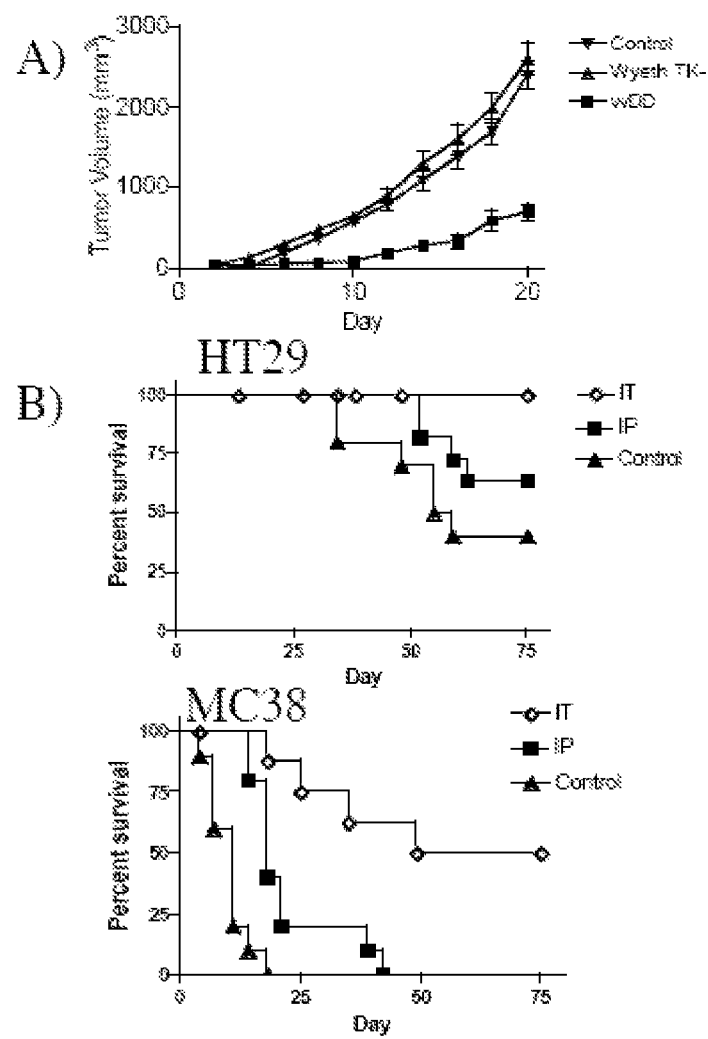
FIGS. 13A-13B—Efficacy of vvDD following delivery by different routes into tumor bearing mouse models.

The anti-tumor effects of vvDD were then analyzed in immunocompetent mouse models. vvDD had significantly greater anti-tumor effects than a Wyeth TK deleted vaccinia strain (the most common vaccinia strain in clinical trials, usually used as a vaccine) when both were delivered intravenously (FIG. 13). Further studies showed that $1 \times 10^9$ PFU of vvDD was capable of significant anti-tumor effects when delivered by either systemic or intratumoral injection to both immunodeficient mice carrying human tumor xenografts and immunocompetent mice bearing syngeneic tumors (FIG. 13).

Figure 9:
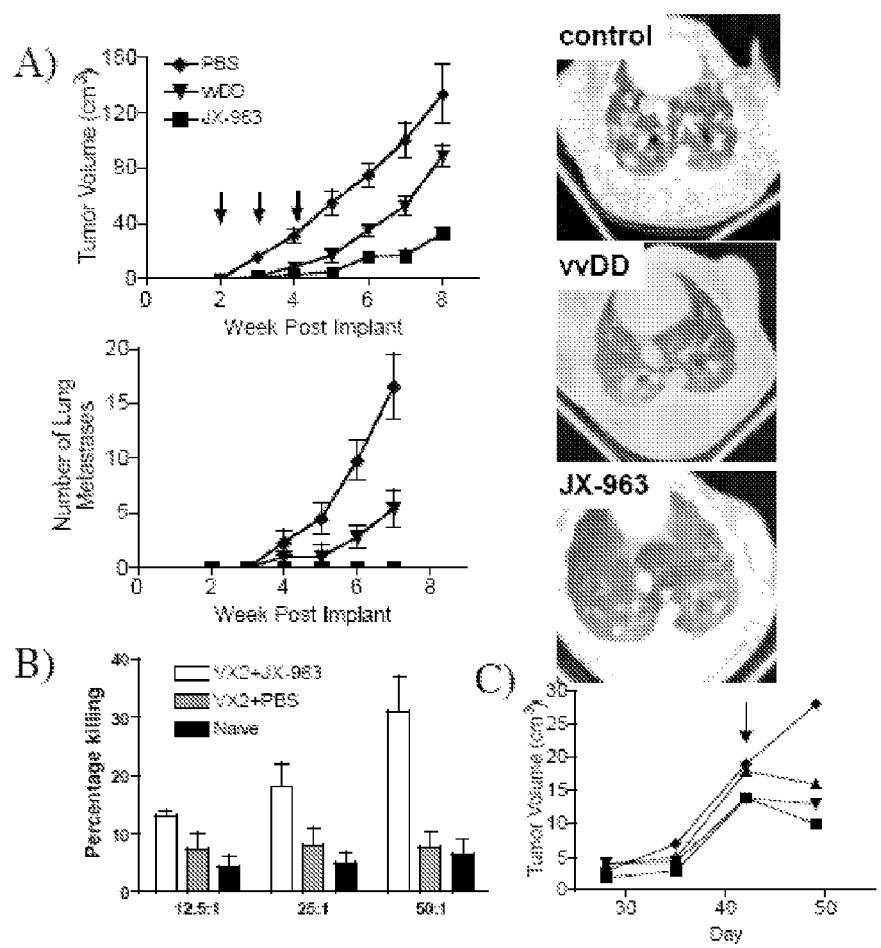
FIGS. 9A-9C—Rabbits bearing VX2 tumors implanted into the liver were followed by CT imaging at times after tumor implantation, CTL assay against VX2 tumor cells, and Rabbits re-treated with JX-963.

In order to increase the anti-tumor potential of vvDD, and to suppress the outgrowth of microscopic tumor deposits that are not vascularized at the time of IV dosing, the cytokine GM-CSF was inserted into the site of the TK gene (under the control of the synthetic E/L promoter); this virus was designated JX-963. Because human GM-CSF is not active in rodents but is active in rabbits (Cody et al., 2005), and in order to assess the activity against much larger primary tumors that reproducibly metastasize, JX-963 was used in a rabbit model with primary (VX2) liver tumors and lung metastases (Kim et al., 2006). As in the mouse models, $1\times10^9$ PFU of intravenous vvDD had significant anti-tumor effects (FIG. 9A). The vvDD virus was also capable of inhibiting the outgrowth of microscopic lung metastases. In order to assess additional efficacy due to concomitant GM-CSF expression, JX-963 was compared directly to vvDD. JX-963 produced greater efficacy against the primary tumor, and completely blocked outgrowth of lung metastases. GM-CSF was detected in the plasma of JX-963 treated mice by ELISA (data not shown). In addition to direct oncolytic effects, JX-963 was also found to cross-protect the animal against the tumor by raising a CTL response against the VX2 tumor cells (FIG. 9B).

Figure 14:
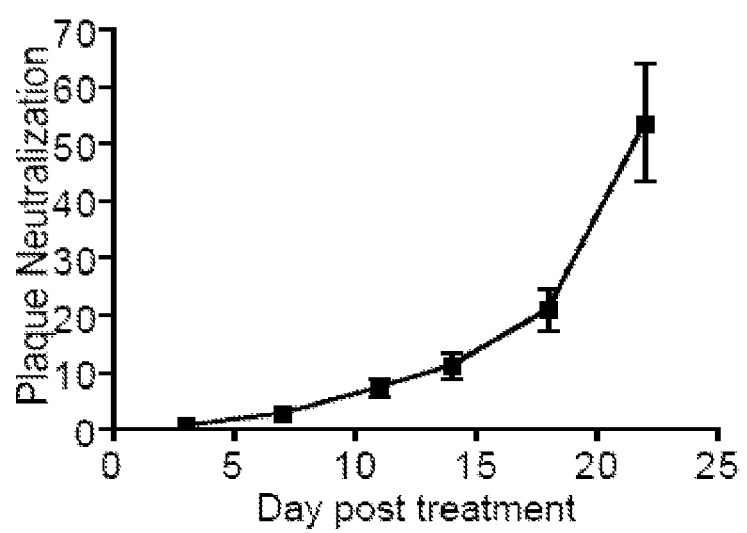
FIG. 14—Formation of neutralizing antibodies following treatment of VX2 tumor bearing rabbits with JX-963 (1×10⁸ PFU). Dilutions of plasma obtained from rabbits at indicated times were incubated with a known number of viral PFU, and dilutions required to retain 50% of the plaques are shown (n=3).

One concern in using vaccinia virus as an anti-tumor agent is that, even though systemic delivery to the tumor is initially possible in naive individuals, the immune response raised by prior exposure to the virus may inhibit the efficacy of subsequent treatment. A strong anti-viral antibody response was raised within 3 weeks of initial infection in the rabbits tested (FIG. 14). To study the feasibility of repeat dosing after neutralizing antibody formation, four rabbits that had initially responded to treatment but had tumor progression after four weeks off of therapy were re-treated. $1\times10^9$ PFU of JX-963 delivered intravenously at 6 weeks after the initial treatment resulted in a decrease in primary tumor size in 3 of 4 animals treated (FIG. 9C).

Therefore, by selecting vaccinia virus, that has evolved to spread through the hematopoietic system, and screening strains for tumor selective replication the inventor was able to find a virus capable of systemic tumor delivery with rapid oncolytic effects. In order to improve the safety of this virus several deletions capable of increasing its therapeutic index were introduced, their mechanism of action described and their biodistribution examined in vivo. Dramatic therapeutic effects against large primary tumors following systemic delivery were demonstrated. Finally, because it is unlikely all tumor cells will be infected, even following systemic viral delivery, GM-CSF was expressed from this viral backbone. The addition of GM-CSF was found to increase the effectiveness of this virus against primary tumors, prevent the outgrowth of micrometastases, and produced an anti-tumor CTL response. This indicates that this virus, JX-963, is capable of systemic delivery to tumors, where it rapidly and efficiently destroys tumor tissue, while sparing normal organs, and at the same time induces an immune response within the tumor that is capable of recognizing tumor antigens produced in situ. Repeat dosing was further shown to produce additional anti-tumor effects, either by direct oncolysis or by boosting the anti-tumor immune response. JX-963 therefore has the potential to effectively treat a variety of tumors.

\* \* \*

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference:

U.S. Pat. No. 4,554,101
U.S. Pat. No. 4,683,195
U.S. Pat. No. 4,683,202
U.S. Pat. No. 4,684,611
U.S. Pat. No. 4,800,159
U.S. Pat. No. 4,879,236
U.S. Pat. No. 4,883,750
U.S. Pat. No. 4,946,773
U.S. Pat. No. 4,952,500
U.S. Pat. No. 5,220,007
U.S. Pat. No. 5,279,721
U.S. Pat. No. 5,284,760
U.S. Pat. No. 5,302,523
U.S. Pat. No. 5,322,783
U.S. Pat. No. 5,354,670
U.S. Pat. No. 5,366,878
U.S. Pat. No. 5,384,253
U.S. Pat. No. 5,389,514
U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,633,016
U.S. Pat. No. 5,635,377
U.S. Pat. No. 5,641,515
U.S. Pat. No. 5,656,610
U.S. Pat. No. 5,702,932
U.S. Pat. No. 5,736,524
U.S. Pat. No. 5,739,169
U.S. Pat. No. 5,780,448
U.S. Pat. No. 5,789,166
U.S. Pat. No. 5,789,215
U.S. Pat. No. 5,798,208
U.S. Pat. No. 5,798,339
U.S. Pat. No. 5,801,005
U.S. Pat. No. 5,824,311
U.S. Pat. No. 5,824,348
U.S. Pat. No. 5,830,650
U.S. Pat. No. 5,830,880
U.S. Pat. No. 5,840,873
U.S. Pat. No. 5,843,640
U.S. Pat. No. 5,843,650
U.S. Pat. No. 5,843,651

U.S. Pat. No. 5,843,663
U.S. Pat. No. 5,846,225
U.S. Pat. No. 5,846,233
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,846,945
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,871,740
U.S. Pat. No. 5,871,986
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,925,565
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
Alcami and Smith, *Cell.*, 71(1):153-67, 1992.
Alcami et al., *Sem. Virol.*, 5:419-427, 1998.
Alcami et al., *Virology*, 74(23):11230-9, 2000.

Almendro et al., *J. Immunol*, 157(12):5411-5421, 1996.
Andoh et al., *Cancer Immunol. Immunother.*, 50(12):663-72, 2002.
Andrade et al., *Biochem J.*, 381, 437-46, 2004.
Angel et al., *Cell*, 49:729, 1987b.
Angel et al., *Mol. Cell. Biol.*, 7:2256, 1987.
Angel et al., *Mol. Cell. Biol.*, 7:2256, 1987a.
Arap et al., *Cancer Res.*, 55(6):1351-1354, 1995.
Atchison and Perry, *Cell*, 46:253, 1986.
Atchison and Perry, *Cell*, 48:121, 1987.
Austin-Ward and Villaseca, *Rev. Med. Chil.*, 126(7):838-45, 1998.
Ausubel et al., In: *Current Protocols in Molecular Biology*, John, Wiley & Sons, Inc, New York, 1994.
Bajorin et al., *J. Clin. Oncol.*, 6(5):786-92, 1988.
Bakhshi et al., *Cell.*, 41(3):899-906, 1985.
Banerji et al., *Cell.*, 27(2 Pt 1):299-308, 1981.
Banerji et al., *Cell.*, 33(3):729-740, 1983.
Barker and Berk, *Virology*, 156, 107-21, 1987.
Bellus, *J. Macromol. Sci. Pure Appl. Chem.*, A31(1): 1355-1376, 1994.
Berkhout et al., *Cell*, 59:273-282, 1989.
Blanar et al., *EMBO J.*, 8:1139, 1989.
Blasco and Moss, *J. Virology*, 66(7): 4170-4179, 1992.
Blasco et al., *J. Virology*, 67(6):3319-3325, 1993.
Bodine and Ley, *EMBO J.*, 6:2997, 1987.
Boshart et al., *Cell*, 41:521, 1985.
Bosze et al., *EMBO J.*, 5(7):1615-1623, 1986.
Boyd et al., *Cell.*, 79:341-351, 1994.
Braddock et al., *Cell*, 58:269, 1989.
Braisted and Wells, *Proc. Natl. Acad. Sci. USA*, 93(12):5688-5692, 1996.
Brizel, *Semin. Radiat. Oncol.*, 8(4):237-246, 1998.
Bukowski et al., *Clin. Cancer Res.*, 4(10):2337-47, 1998.
Bulla and Siddiqui, *J. Virol.*, 62:1437, 1986.
Buller and Palumbo, Microbiol Rev, 55, 80-122, 1991.
Buller et al., *J. Virol*, 62, 866-74, 1988.
Burton and Barbas, *Adv. Immunol.*, 57:191-280, 1994.
Caldas et al., *Nat. Genet.*, 8(1):27-32, 1994.
Campbell and Villarreal, *Mol. Cell. Biol*, 8:1993, 1988.
Campere and Tilghman, *Genes and Dev.*, 3:537, 1989.
Campo et al., *Nature*, 303:77, 1983.
Cantrell et al., *Proc. Nat'l Acad. Sci. USA* 82:6250-6254, 1985.
Caragine et al., *Cancer Res.*, 62(4):1110-5, 2002.
Carbonelli et al., *FEMS Microbiol. Lett.*, 177(1):75-82, 1999.
Celander and Haseltine, *J. Virology*, 61:269, 1987.
Celander et al., *J. Virology*, 62:1314, 1988.
Chandler et al., Cell, 33:489, 1983.
Chandler et al., *Proc. Natl. Acad. Sci. USA*, 94(8):3596-601, 1997.
Chang et al., *Mol. Cell. Biol*, 9:2153, 1989.
Chatterjee et al., *Proc Natl. Acad Sci. U.S.A.*, 86:9114, 1989.
Chen and Okayama, *Mol. Cell Biol.*, 7(8):2745-2752, 1987.
Chen et al., *Lab Anim*, 38, 79-84, 2004.
Cheng et al., *Cancer Res.*, 54(21):5547-5551, 1994.
Choi et al., *Cell*, 53:519, 1988.
Christodoulides et al., *Microbiology*, 144(Pt 1 1):3027-37, 1998.
Cleary and Sklar, *Proc. Natl. Acad. Sci. USA*, (21):7439-7443, 1985.
Cleary et al., *J. Exp. Med.*, 164(1):315-320, 1986.
Cocea, *Biotechniques*, 23(5):814-816, 1997.
Cody et al., *Vet Immunol Immunopathol*, 103:163-72, 2005. Cohen et al., *J. Cell. Physiol.*, 5:75, 1987.
Colamonici et al., *J. Biol Chem*, 270:15974-15978, 1995.
Cooley et al., *Science*, 239(4844):1121-1128, 1988.

Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Culver et al., *Science*, 256(5063): 1550-1552, 1992.
Cunningham and Wells, *Science*, 244(4908):1081-1085, 1989
Curran, *Semin. Radiat. Oncol.*, 8(4 Suppl 1):2-4, 1998.
Dandolo et al., *J. Virology*, 47:55-64, 1983.
Davidson et al., *J. Immunother.*, 21(5):389-98, 1998.
De Villiers et al., *Nature*, 312(5991):242-246, 1984.
Deschamps et al., *Science*, 230:1174-1177, 1985.
Dillman, *Cancer Biother. Radiopharm.*, 14(1):5-10, 1999.
Dobbelstein and Shenk, *J. Virology*, 70:6479-6485, 1996.
Dranoff et al., *Proc. Natl. Acad. Sci. USA*, 90:3539-3543, 1993.
Durrant and Spendlove, *Curr. Opin. Investig. Drugs*, 2(7): 959-66, 2001.
Earl et al., In: *Preparation of Cell Cultures and Vaccinia Virus Stocks*. Ausubel et al. (Eds.), Current Protocols In Molecular Biology, 16(16):1-16, John Wiley & Sons, 1998.
Edbrooke et al., *Mol. Cell. Biol.*, 9:1908, 1989.
Edlund et al., *Science*, 230:912-916, 1985.
Eliopoulos et al., *Oncogene*, 11(7):1217-28, 1995.
el-Kareh and Secomb, *Crit. Rev. Biomed. Eng.*, 25(6):503-571, 1997.
Erlandsson, *Cancer Genet. Cytogenet.*, 104(1):1-18, 1998.
European Appl. 320 308
European Appl. 329 822
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Frohman, In: *PCR Protocols: A Guide To Methods And Applications*, Academic Press, N.Y., 1990.
Fujita et al., *Cell*, 49:357, 1987.
GB Application 2 202 328
GenBank Accession Number NC_001559
Gertig et al., *Semin. Cancer Biol.*, 8(4): 285-98, 1998.
Gilles et al., *Cell*, 33:717, 1983.
Gloss et al., *EMBO J.*, 6:3735, 1987.
Gnant et al., *Cancer Res.*, 59(14):3396-403, 1999.
Godbout et al., *Mol. Cell. Biol.*, 8:1169, 1988.
Goebel et al., *Virology*, 179(1): 247-66 and 517-63, 1990.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Graham et al., *Virology*, 229(1): 12-24, 1997.
Greene et al., *Immunology Today*, 10:272, 1989
Gross et al., *Genes Dev.*, 13(15): 1899-911, 1999.
Grosschedl and Baltimore, *Cell*, 41:885, 1985.
Hanibuchi et al., *Int. J. Cancer*, 78(4):480-5, 1998.
Harland and Weintraub, *J. Cell Biol.*, 101:1094-1099, 1985.
Haslinger and Karin, *Proc. Natl. Acad. Sci. USA*, 82:8572, 1985.
Hauber and Cullen, *J. Virology*, 62:673, 1988.
Heise et al., *Cancer Gene Ther.*, 6(6):499-504, 1999.
Heise et al., *Nat Med*, 3, 639-45, 1997.
Hellstrand et al., *Acta Oncol.*, 37(4):347-353, 1998.
Hen et al., *Nature*, 321:249, 1986.
Hengstschlager et al, *J. Biol. Chem*, 269, 13836-42, 1994.
Hensel et al., *Lymphokine Res.*, 8:347, 1989.
Hermiston, *J. Clin. Invest.*, 105:1169-1172, 2000.
Herr and Clarke, *Cell.*, 45:461, 1986.
Hilton et al., *J. Biol. Chem.*, 271(9):4699-4708, 1996.
Hirochika et al., *J. Virolology*, 61:2599, 1987.
Hirsch et al., *Mol. Cell. Biol.*, 10:1959, 1990.
Ho et al., *Environ Health Perspect*, 106(5): 1219-1228, 1998.
Holbrook et al., *Virology*, 157:211, 1987.
Homey et al., *Nature. Rev. Immunol.*, 2:175-184, 2002.
Horlick and Benfield, *Mol. Cell. Biol.*, 9:2396, 1989.
Huang et al., *Cell.*, 27:245, 1981.
Hug et al., *Mol. Cell. Biol.*, 8:3065, 1988.
Hui and Hashimoto, *Infect. Immun.*, 66(11):5329-36, 1998.
Hussussian et al., *Nat. Genet.*, 8(1):15-21, 1994.
Hwang et al., *Mol. Cell. Biol.*, 10:585, 1990.
Ikeda et al., *Nat. Med.*, 5(8):881-7, 1999.
Imagawa et al., *Cell*, 51:251, 1987.
Imbra and Karin, *Nature*, 323:555, 1986.
Imler et al., *Mol. Cell. Biol*, 7:2558, 1987.
Imperiale and Nevins, *Mol. Cell. Biol.*, 4:875, 1984.
Innis et al., *Proc. Natl. Acad. Sci. USA*, 85(24):9436-9440, 1988.
Inouye and Inouye, *Nucleic Acids Res.*, 13:3101-3109, 1985.
Irie and Morton, *Proc. Natl. Acad. Sci. USA*, 83(22):8694-8698, 1986.
Irie et al., *Lancet.*, 1(8641):786-787, 1989.
Isaacs et al., *Proc. Natl. Acad. Sci. USA*, 89(2):628-32, 1992.
Jakobovits et al., *Mol. Cell Biol.*, 8:2555, 1988.
Jameel and Siddiqui, *Mol Cell. Biol.*, 6:710, 1986.
Jaynes et al., *Mol. Cell. Biol.*, 8:62, 1988.
Johnson and Hamdy, *Oncol. Rep.*, 5(3):553-7, 1998.
Johnson et al., *Mol. Cell. Biol.*, 9:3393, 1989.
Ju et al., *J. Neuropathol. Exp. Neurol.*, 59(3):241-50, 2000.
Kadesch and Berg, *Mol. Cell. Biol.*, 6:2593, 1986.
Kaeppler et al., *Plant Cell Reports*, 9: 415-418, 1990.
Kamb et al., *Nat. Genet.*, 8(1):23-2, 1994.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Kato et al, *J. Biol Chem.*, 266:3361-3364, 1991.
Kawamoto et al., *Mol. Cell. Biol.*, 8:267, 1988.
Kay et al., *Proc. Natl. Acad. Sci. USA*, 94(9):4686-91, 1997.
Kerr et al., *Br. J. Cancer*, 26(4):239-257, 1972.
Kettle et al., *J. Gen. Virology*, 78:677-685, 1997.
Kidd, *J. Exp Med*, 71, 813-37, 1940.
Kiledjian et al., *Mol. Cell. Biol.*, 8:145, 1988.
Kim et al., *Mol Ther*, 14, 361-70, 2006.
Kim et al., *Nat. Med.*, 7(7):781-787, 2001.
Klamut et al., *Mol. Cell. Biol.*, 10:193, 1990.
Koch et al., *Mol. Cell. Biol.*, 9:303, 1989.
Kolmel, *J. Neurooncol.*, 38(2-3):121-5, 1998.
Koncz et al, *EMBO J.*, 9(5):1337-1346, 1990.
Kraus et al., *FEBS Lett.*, 428(3):165-170, 1998.
Kriegler and Botchan, In: *Eukaryotic Viral Vectors*, Gluzman (ed), Cold Spring Harbor Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kwoh et al., *Proc. Nat. Acad. Sci. USA*, 86:1173, 1989.
Kyte and Doolittle, *J. Mol. Biol.*, 57(1):105-32, 1982.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lee et al., *DNA Cell. Biol.*, 16(11): 1267-75, 1997.
Lee et al., *Nature*, 294:228, 1981.
Lee et al, *Nucleic Acids Res.*, 12:4191-206, 1984.
Levenson et al., *Hum Gene Ther.* 20;9(8):1233-1236, 1998.

Levinson et al., *Nature*, 295:79, 1982.
Liebermann, *Oncogene*, 17(10):1189-94, 1998.
Lin et al., *Mol. Cell. Biol.*, 10:850, 1990.
Luker et al., *Virology*, 341, 284-300, 2005.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.* 3:1108, 1983.
Macejak and Sarnow, *Nature*, 353:90-94, 1991.
Magi-Galluzzi et al., *Anal. Quant. Cytol. Histol.*, 20(5):343-50, 1998.
Majors and Varmus, *Proc. Natl Acad. Sci. USA*, 80:5866, 1983.
Mangray and King, *Front Biosci.*, 3:D1 148-60, 1998.
Marks et al, *Symp. Soc. Exp. Biol.*, 45:77-87, 1991.
Marsters et al., *Recent Prog Horm Res*, 54:225-234, 1999.
Mastrangelo and Lattime, *Cancer Gene Ther.*, 9:1013-1021, 2002.
Mastrangelo et al, *Adv. Exp. Med. Biol.*, 465:391-400, 2000.
Mastrangelo et al., *Cancer Gene Ther.*, 6:409-422, 1999.
Mayer et al., *Radiat. Oncol. Investig.*, 6(6):281-288, 1998.
McCart et al., *Am. Soc. Gene Therapy*, 160, 1999.
McCart et al., *Cancer Res*, 61, 8751-57, 2001.
McCart et al., *Gene Ther.*, 7(14):1217-23, 2000.
McNeall et al., *Gene*, 76:81, 1989.
Miksicek et al., *Cell*, 46:203, 1986.
Mitchell et al, *Ann. NY Acad. Sci.*, 690:153-166, 1993.
Mitchell et al., *J. Clin. Oncol.*, 8(5):856-869, 1990.
Monks et al., *J. Natl Cancer Inst*, 83, 757-66, 1991.
Mordacq and Linzer, *Genes and Dev.*, 3:760, 1989.
Moreau et al., *Nucl. Acids Res.*, 9:6047, 1981.
Mori et al., *Cancer Res.*, 54(13):3396-3397, 1994.
Morton et al., *Arch. Surg.*, 127:392-399, 1992.
Moss, In: *Fields Virology*, Fields (ed.), Lippincott-Raven Publ, Phila., 3:3637,2672, 1996.
Mossman et al., *Virology*, 215(1):17-30, 1996.
Mougin et al., *Ann. Biol. Clin.*, (Paris) 56(1): 21-8, 1998.
Muesing et al., *Cell*, 48:691, 1987.
Mumby and Walter, *Cell Regul.*, 2(8):589-98, 1991.
Natoli et al., *Biochem. Pharmacol.*, 56(8):915-20, 1998.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987.
Nielsen et al., *Cancer Gene Therapy*, 4(6):S12, 1997.
Nielsen et al., *Clin. Cancer Res.*, 4(4):835-846, 1998.
Nobori et al., *Nature*, 368(6473):753-6, 1994.
Nomoto et al., *Gene*, 236(2):259-71, 1999.
Ochi et al., *Am. J. Gastroenterol.*, 93(8):1366-1368, 1998.
Oh et al., *Exp. Mol. Path.*, 73:67-73, 2002.
Ohara et al., *Proc. Natl. Acad. Sci. USA*, 86:5673-5677, 1989.
Ohara, *Gan To Kagaku Ryoho*, 25(6): 823-8, 1998.
Okamoto et al., *Proc. Natl. Acad. Sci. USA*, 1(23):11045-11049, 1994.
Omirulleh et al., *Plant Mol. Biol.*, 21(3):415-428, 1993.
Ondek et al., *EMBO J.*, 6:1017, 1987.
Orlow et al., *Cancer Res.*, 54(11):2848-2851, 1994.
Ornitz et al., *Mol. Cell. Biol.*, 7:3466, 1987.
Paeng et al., *J. Nucl. Med.*, 44:2033-2038, 2003.
Palmiter et al., *Nature*, 300:611, 1982.
Parato et al., *Nat Rev Cancer*, 5, 965-76, 2005.
PCT WO 88/10315
PCT WO 89/06700
PCT WO 90/07641
PCT WO 94/09699
PCT WO 95/06128
PCT/US03/025141
PCT/US87/00880
PCT/US89/01025
Pech et al., *Mol. Cell. Biol.*, 9:396, 1989.
Pelletier and Sonenberg, *Nature*, 334(6180):320-325, 1988.
Perez-Stable and Constantini, *Mol. Cell. Biol.*, 10:11 16, 1990.
Picard and Schafffier, *Nature*, 307:83, 1984.
Pietras et al., *Oncogene*, 17(17):2235-49, 1998.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10: 1076, 1990.
Potrykus et al, *Mol. Gen. Genet.*, 199:183-188, 1985.
Puhlmann et al., *Cancer Gene Ther.*, 7(1):66-73, 2000.
Puhlmann et al., *Hum Gene Ther.*, 10: 649-57, 1999.
Qin et al., *Proc. Natl. Acad. Sci. USA*, 95(24):14411-14416, 1998.
Queen and Baltimore, *Cell*, 35:741, 1983.
Quinn et al., *Mol. Cell. Biol.*, 9:4713, 1989.
Ravindranath and Morton, *Intern. Rev. Immunol.*, 7: 303-329, 1991.
Redondo et al., *Science*, 247:1225, 1990.
Reisman and Rotter, *Mol. Cell. Biol.*, 9:3571, 1989.
Remington's Pharmaceutical Sciences" 15th Edition, pages 1035-1038 and 1570-1580
Resendez Jr. et al., *Mol. Cell. Biol.*, 8:4579, 1988.
Ripe et al.,*Mol. Cell. Biol.*, 9:2224, 1989.
Rippe et al., *Mol. Cell. Biol.*, 10:689-695, 1990.
Rittling et al., *Nuc. Acids Res.*, 17:1619, 1989.
Rosel et al., *J. Virology*, 60(2):436-449, 1986.
Rosen et al., *Cell*, 41:813, 1988.
Rosenberg et al., *Ann. Surg.* 210(4):474-548, 1989.
Rosenberg et al., *N. Engl. J. Med.*, 319:1676, 1988.
Sakai et al., *Genes and Dev.*, 2:1144, 1988.
Sambrook et al., In *Molecular Cloning: A Laboratory Manual*, Second edition, Cold Spring Harbor Laboratory, Cold Spring Harbor, N.Y., 1989.
Saraiva and Alcami, *J. Virology*, 75(1):226-33, 2001.
Satake et al., *J. Virology*, 62:970, 1988.
Schaffier et al., *J. Mol. Biol.*, 201:81, 1988.
Searle et al., *Mol. Cell. Biol.*, 5:1480, 1985.
Seet et al., *Proc. Natl. Acad. Sci. USA*, 98(16):9008-13, 2001.
Serrano et al., *Nature*, 366:704-707, 1993.
Serrano et al., *Science*, 267(5195):249-252, 1995.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sinkovics and Horvath, *J. Clin. Viro.*, 16:1-15, 2000.
Sleigh and Lockett, *J. EMBO*, 4:3831, 1985.
Smith and Vanderplasschen, *Adv. Exp. Med. Biol.*, 440:395-414, 1998.
Smith et al., *Immunol. Rev.*, 159:137-154, 1997.
Solyanik et al., *Cell. Prolif.*, 28(5):263-78, 1995.
Sommer et al. *EMBO J.*, 9(3):605-613, 1990.
Spalholz et al., *Cell*, 42:183, 1985.
Spandau and Lee, *J. Virology*, 62:427, 1988.
Spandidos and Wilkie, *EMBO J.*, 2:1193, 1983.
Spriggs et al., *Cell*, 71(1):145-52, 1992.
Stephens and Hentschel, *Biochem. J.*, 248:1, 1987.
Stokke et al., *Cell. Prolif.*, 30(5):197-218, 1997.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Symons et al., *Cell*, 81:551-560, 1995.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.

Taylor and Kingston, *Mol. Cell. Biol.*, 10:176, 1990b.
Taylor et al., *J. Biol. Chem.*, 264:15160, 1989.
Thiesen et al., *J. Virology*, 62:614, 1988.
Thorne et al., *Semin Oncol*, 32, 537-48, 2005.
Tjemberg, *Acta Radiol*, suppl no. 214, 1962.
Todo et al., *Cancer Res.*, 61:153-161, 2001.
Treisman, *Cell*, 42:889, 1985.
Tronche et al., *Mol. Biol. Med.*, 7:173, 1990.
Trudel and Constantini, *Genes and Dev.* 6:954, 1987.
Tsujimoto and Croce, et al., *Proc. Natl. Acad. Sci. USA,.* 83(14):5214-5218, 1986.
Tsujimoto et al., *Science*, 228(4706):1440-1443, 1985.
Tsumaki et al., *J. Biol. Chem.*, 273(36):22861-4, 1998.
Tyndell et al., *Nuc. Acids. Res.*, 9:6231, 1981.
Upton et al., *Virology*, 184(1):370-82, 1991.
Vanderplasschen et al., *Proc. Natl. Acad. Sci. USA*, 95(13): 7544-9, 1998.
Vannice and Levinson, *J. Virology*, 62:1305, 1988.
Vasseur et al., *Proc Natl. Acad. Sci. USA.*, 77:1068, 1980.
Vicari and Caus, *Cytokine Growth Factor Rev.*, 13:143-154, 2002.
Vogelstein and Kinzler, *Cell*, 70(4):523-6, 1992.
Walker et al., *Proc. Natl. Acad. Sci. USA*, 89:392-396 1992.
Wallach et al., In: *The cytokine network and immune functions*, Theze (ed.), Oxford Univ. Press, Oxford, UK, 51-84, 1999.
Wang and Calame, *Cell*, 47:241, 1986.
Warren et al., *Biochemistry*, 35(27):8855-8862, 1996.
Weber et al., *Cell*, 36:983, 1984.
Wein et al., *Cancer Res*, 63, 1317-24, 2003.
Weinberger et al. *Mol. Cell. Biol.*, 8:988, 1984.
Weislow et al., *J. Natl Cancer Inst*, 81, 577-86, 1989.
Winoto and Baltimore, *Cell* 59:649, 1989.
Wold et al., *Trends Microbiol.*, 2:437-443, 1994.
Wong et al., *Gene*, 10:87-94, 1980.
Wu and Wu, *J. Biol. Chem.*, 262:4429-4432, 1987.
Yelton et al., *J. Immunol.*, 155(4):1994-2004, 1995.
Yutzey et al. *Mol. Cell. Biol.*, 9:1397, 1989.
Zeng et al, *Biochemistry*, 35(40):13157-13164, 1996.
Zhao-Emonet et al., *Biochim. Biophys. Acta*, 1442(2-3):109-119, 1998.

The invention claimed is:

1. A method of killing a cancer cell in a human subject comprising administering intravascularly to the subject $10^9$ to $10^{10}$ plaque forming units (Pfu) of a replicative Wyeth strain vaccinia virus JX-594.

2. The method of claim 1, wherein the vaccinia virus is administered intravenously.

3. The method of claim 1, wherein the vaccinia virus is administered intraarterially.

4. The method of claim 1, wherein the vaccinia virus is in a pharmaceutically acceptable formulation.

5. The method of claim 1, wherein the subject is administered the vaccinia virus multiple times.

6. The method of claim 5, wherein a second treatment occurs within 3 weeks of a first treatment.

7. The method of claim 6, wherein the second treatment occurs within 2 weeks of the first treatment.

8. The method of claim 5, wherein the same dose is administered.

9. The method of claim 1, wherein the administration occurs intravascularly by injection.

10. The method of claim 1, wherein the administration occurs intravascularly using intravenous drip or bolus.

11. The method of claim 1, wherein the administration occurs intravascularly using a pump.

12. The method of claim 1, wherein the cancer cell is a metastasized cancer cell.

13. The method of claim 1, wherein the subject has lung cancer, colorectal cancer, breast cancer, prostate cancer, pancreatic cancer, hepatocellular cancer, leukemia, lymphoma, myeloma or melanoma.

14. A method of treating one or more metastases in a human subject comprising administering intravascularly to the subject $10^9$ to $10^{10}$ plaque forming units (Pfu) of a replicative Wyeth strain vaccinia virus JX-594.

15. The method of claim 1, wherein expression of a nucleic acid encoding granulocyte-macrophage colony stimulating factor (GM-CSF) is directed by a synthetic vaccinia early/late promoter.

* * * * *